(12) United States Patent
Tretiakova et al.

(10) Patent No.: US 11,241,506 B2
(45) Date of Patent: Feb. 8, 2022

(54) COMPOSITION FOR TREATMENT OF CRIGLER-NAJJAR SYNDROME

(71) Applicant: The Trustees of the University of Pennsylvania, Philadelphia, PA (US)

(72) Inventors: Anna P. Tretiakova, Philadelphia, PA (US); Jenny Agnes Sidrane, Phoenixville, PA (US); James M. Wilson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 528 days.

(21) Appl. No.: 16/061,945

(22) PCT Filed: Dec. 14, 2016

(86) PCT No.: PCT/US2016/066657
§ 371 (c)(1),
(2) Date: Jun. 13, 2018

(87) PCT Pub. No.: WO2017/106345
PCT Pub. Date: Jun. 22, 2017

(65) Prior Publication Data
US 2018/0369418 A1    Dec. 27, 2018

Related U.S. Application Data

(60) Provisional application No. 62/266,969, filed on Dec. 14, 2015, provisional application No. 62/348,029, filed on Jun. 9, 2016.

(51) Int. Cl.
| | | |
|---|---|---|
| C12N 15/63 | (2006.01) | |
| A61K 48/00 | (2006.01) | |
| C12N 9/10 | (2006.01) | |
| A61P 1/16 | (2006.01) | |
| A61K 35/761 | (2015.01) | |
| C12N 15/62 | (2006.01) | |

(52) U.S. Cl.
CPC ........ *A61K 48/0058* (2013.01); *A61K 35/761* (2013.01); *A61K 48/0008* (2013.01); *A61P 1/16* (2018.01); *C12N 9/1051* (2013.01); *C12N 15/62* (2013.01); *C12Y 204/01017* (2013.01); *C12N 2750/14143* (2013.01); *C12N 2810/6027* (2013.01); *C12N 2830/008* (2013.01)

(58) Field of Classification Search
CPC ............. A61K 48/0058; A61K 35/761; A61K 48/0008; A61P 1/16; C12N 9/1051; C12N 15/62; C12N 2750/14143; C12N 2810/6027; C12N 2830/008; C12Y 204/01017
See application file for complete search history.

(56) References Cited

U.S. PATENT DOCUMENTS

| | | | |
|---|---|---|---|
| 5,139,941 | A | 8/1992 | Muzycka et al. |
| 5,478,745 | A | 12/1995 | Samulski et al. |
| 5,741,683 | A | 4/1998 | Zhou et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowitz et al. |
| 6,596,535 | B1 | 7/2003 | Carter |
| 6,660,514 | B1 | 12/2003 | Zolotukhin et al. |
| 6,951,753 | B2 | 10/2005 | Shenk et al. |
| 7,094,604 | B2 | 8/2006 | Snyder et al. |
| 7,125,717 | B2 | 10/2006 | Carter |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,456,683 | B2 | 11/2008 | Takano et al. |
| 7,588,772 | B2 | 9/2009 | Kay et al. |
| 7,790,449 | B2 | 9/2010 | Gao et al. |
| 7,906,111 | B2 | 3/2011 | Wilson et al. |
| 8,318,480 | B2 | 11/2012 | Gao et al. |
| 8,962,330 | B2 | 2/2015 | Gao et al. |
| 8,962,332 | B2 | 2/2015 | Gao et al. |
| 9,493,788 | B2 | 11/2016 | Gao et al. |

(Continued)

FOREIGN PATENT DOCUMENTS

| | | |
|---|---|---|
| EP | 1310571 | 5/2003 |
| WO | WO 1997/021825 | 6/1997 |

(Continued)

OTHER PUBLICATIONS

Score_result_Mingozzi_et_al (Year: 2017).*
Adam et al. Evolution of indications and results of liver transplantation in Europe. A report from the European Liver Transplant Registry (ELTR). Journal of Hepatology, Sep. 2012, 57(3): 675-88.
Al Shurafa et al., Living related liver transplantation for Crigler-Najjar syndrome in Saudi Arabia. Clin Transplant, Jun. 2002; 16: 222-6.
Arias et al. Chronic nonhemolytic unconjugated hyperbilirubinemia with glucuronyl transferase deficiency: clinical, biochemical, pharmacologic and genetic evidence for heterogeneity. The American Journal of Medicine, Sep. 1969; 47(3): 395-409.

(Continued)

*Primary Examiner* — Mindy G Brown
(74) *Attorney, Agent, or Firm* — Howson & Howson LLP

(57) ABSTRACT

The invention provides a polynucleotide sequence (e.g., a gene, e.g., DNA or RNA) encoding UGT1A1 (e.g., expressing human UGT1A1). The invention further provides a vector, such as an adeno-associated virus (AAV) vector (e.g., AAV8) having a vector genome including inverted terminal repeat sequences and a UGT1A1 coding sequence operably linked to one or more expression control sequences (e.g., expression control sequences including a liver-specific promoter). Also provided are compositions containing these AAV vectors and methods of treating Crigler-Nijjar syndrome type I, Crigler-Nijjar syndrome type II, and Gilbert syndrome.

22 Claims, 18 Drawing Sheets

Specification includes a Sequence Listing.

(56) References Cited

U.S. PATENT DOCUMENTS

| | | | |
|---|---|---|---|
| 9,587,250 | B2 | 3/2017 | Gao et al. |
| 9,677,089 | B2 | 6/2017 | Gao et al. |
| 10,266,846 | B2 | 4/2019 | Gao et al. |
| 10,471,132 | B2 * | 11/2019 | Mingozzi ............ A61K 48/0058 |
| 2007/0036760 | A1 | 2/2007 | Wilson |
| 2009/0197338 | A1 | 8/2009 | Vandenberghe |
| 2013/0045186 | A1 | 2/2013 | Gao et al. |
| 2017/0028036 | A1 * | 2/2017 | Mingozzi ............ A61K 48/0058 |
| 2019/0017068 | A1 | 1/2019 | Gao et al. |

FOREIGN PATENT DOCUMENTS

| | | | |
|---|---|---|---|
| WO | WO 2003/042397 | 5/2003 | |
| WO | WO 2003/052051 | 6/2003 | |
| WO | WO 2005/033321 | 4/2005 | |
| WO | WO 2006/110689 | 10/2006 | |
| WO | WO 2006/119137 | 11/2006 | |
| WO | WO 2007/120533 | 10/2007 | |
| WO | WO 2011/126808 | 3/2011 | |
| WO | WO 2011/106759 | 9/2011 | |
| WO | WO 2013/063383 | 5/2013 | |
| WO | WO 2013/151665 | 10/2013 | |
| WO | WO 2013/151666 | 10/2013 | |
| WO | WO 2014/124282 | 8/2014 | |
| WO | WO 2014/151341 | 9/2014 | |
| WO | WO 2015/013313 | 1/2015 | |
| WO | WO 2015/162302 | 10/2015 | |
| WO | WO-2015162302 A2 * | 10/2015 | ............. C12N 15/86 |
| WO | WO 2017/100674 | 6/2017 | |
| WO | WO 2017/100676 | 6/2017 | |
| WO | WO 2017/100704 | 6/2017 | |
| WO | WO 2017/160360 | 9/2017 | |

OTHER PUBLICATIONS

Audentes Therapeutics, Press Release: Audentes Therapeutics and the University of Pennsylvania Announce Collaboration to Develop AAV Gene Therapy for Severe Liver Disease, May 4, 2016.
Audentes Therapeutics, Press Release: Audentes Therapeutics Announces Dosing of First Patient in VALENS, a Phase 1/2 Clinical Trial of AT342 for the treatment of Crigler-Najjar Syndrome, Feb. 12, 2018.
Audentes Therapeutics, Press Release: Audentes Therapeutics Announces FDA Clearance of Investigational New Drug Application for AT342 to Treat Crigler-Najjar Syndrome, Feb. 1, 2017.
Audentes Therapeutics, Press Release: Audentes Therapeutics Announces MHRA Approval of Clinical Trial Authorisation Application for AT342 to Treat Crigler-Najjar Syndrome, Nov. 13, 2017.
Audentes Therapeutics, Press Release: Audentes Therapeutics Announces Presentation of Data at the 21st Annual Meeting of the American Society of Gene and Cell Therapy, Apr. 30, 2018.
Audentes Therapeutics, Press Release: Audentes Therapeutics Announces Presentation of Data at the American Society of Gene and Cell Therapy Annual Meeting, May 3, 2017.
Avexis, AVXS-100 clinical update including motor milestones. Presented at World Muscle Society, Oct. 8, 2016.
Bainbridge et al., Effect of gene therapy on visual function in Leber's congenital amaurosis. New England Journal of Medicine, May 22, 2008; 358(21): 2231-9.
Baryam et al., Neurophysiological follow-up of two siblings with Crigler-Najjar syndrome type I and review of literature. Turk J Pediatr. May-Jun. 2013; 55(3): 349-53.
Bell et al., Analysis of Tumors Arising in Male B6C3F1 Mice with and without AAV Vector Delivery to Liver, Molecular Therapy, Jul. 1, 2006; 14(1): 34-44.
Bennett et al., AAV2 gene therapy readministration in three adults with congenital blindness. Science translational medicine, Feb. 8, 2012; 4(120): 120ra115-120ra115.
Bhutani et al., Predictive ability of a predischarge hour-specific serum bilirubin for subsequent significant hyperbilirubinemia in healthy term and near-term newborns. Pediatrics. Jan. 1999; 103(1): 6-14.
Blaschke et al., Crigler-Najjar syndrome: an unusual course with development of neurologic damage at age eighteen. Pediatric research, May 1974; 8(5): 573-590.
Blumenschein et al., Familial nonhemolytic jaundice with late onset of neurological damage. Pediatrics, Nov. 1968, 42(5): 786-92.
Bockor et al. Repeated AAV-mediated gene transfer by serotype switching enables long-lasting therapeutic levels of hUgt1a1 enzyme in a mouse model of Crigler-Najjar syndrome type I. Gene Ther, Oct. 2017; 24(10): 649-60. Epub Aug. 14, 2017.
Bortolussi et al., Age dependent pattern of cerebellar susceptibility to bilirubin neurotoxicity in vivo in mice. Dis Model Mech, Sep. 2014; 7(9): 1057-1068. Epub Jul. 25, 2014.
Bortolussi et al., Life-long Correction of Hyperbilirubinemia with a Neonatal Liver-Specific AAV-Mediated Gene Transfer in a Lethal Mouse Model of Crigler-Najjar Syndrome. Human Gene Therapy, Sep. 1, 2014; 25(9): 844-55.
Bortolussi et al., Rescue of bilirubin-induced neonatal lethality in a mouse model of Crigler-Najjar syndrome type I by AAV9-mediated gene transfer. FASEB J, Mar. 2012; 26(3): 1052-63. Epub Nov. 17, 2011.
Boutin et al., Prevalence of serum IgG and neutralizing factors against adeno-associated virus (AAV) types 1, 2, 5, 6, 8, and 9 in the healthy population: implications for gene therapy using AAV vectors. Human Gene Therapy, Jun. 2010; 21(6): 704-12.
Brantly et al., Sustained transgene expression despite T lymphocyte responses in a clinical trial of rAAV1-AAT gene therapy. PNAS USA, Sep. 22, 2009; 106(38): 16363-8.
Buchlis et al., Factor IX expression in skeletal muscle of a severe hemophilia B patient 10 years after AAV-mediated gene transfer. Blood, Mar. 29, 2012; 119(13): 3038-41.
Bucuvalas and Ryckman. Long-term outcome after liver transplantation in children. Pediatric transplantation, Mar. 20, 2002; 6: 30-6.
Buning et al. Recent developments in adeno-associated virus vector technology. J. Gene Med., Jul. 2008; 10(7): 717-33.
Calcedo et al., Adeno-associated virus antibody profiles in newborns, children, and adolescents. Clin Vaccine Immunol, Sep. 2011; 18(9): 1586-8. Epub Jul. 20, 2011.
Calcedo et al., Worldwide Epidemiology of Neutralizing Antibodies to Adeno-Associated Viruses. Journal of Infectious Diseases, Feb. 1, 2009; 199(3): 381-90.
Caldedo et al., AAV Natural Infection Induces Broad Cross-Neutralizing Antibody Responses to Multiple AAV Serotypes in Chimpanzees. Hum. Gene Ther. Clin. Dev., Jun. 2016; 27(2): 79-82.
Cashore, Kernicterus and bilirubin encephalopathy. Seminars in Liver Disease, 1988; 8(2): 163-7.
Chandler et al., Recombinant adeno-associated viral integration and genotoxicity: insights from animal models. Hum Gene Ther, Apr. 2017; 28(4): 314-22.
Chandler et al., Vector design influences hepatic genotoxicity after adeno-associated virus gene therapy. J Clin Invest, Feb. 2015; 125(2): 870-80.
Chen et al., Amelioration of hyperbilirubinemia in Gunn rats after transplantation of human induced pluripotent stem cell-derived hepatocytes. Stem Cell Reports, Jul. 2015; 5(1): 22-30. Epub Jun. 11, 2015.
Chen et al., Biodistribution of AAV8 vectors expressing human low-density lipoprotein receptor in a mouse model of homozygous familial hypercholesterolemia. Human Gene Therapy Clinical Development, Dec. 2013, 24(4): 154-60.
Clarke et al., Genetic defects of the Udp-glucuronosyltransferase-1 (UGT1) gene that cause familial non-haemolytic unconjugated hyperbilirubinaemias. Clinica chimica acta, Oct. 9, 1997; 266(1): 63-74.
Clement et al., Large-scale adeno-associated viral vector production using a herpesvirus-based system enables manufacturing for clinical studies. Hum Gene Therapy, Aug. 2009; 20(8): 796-806.
CLINICALTRIALS.gov, NCT03223194—Gene Transfer Clinical Study in Crigler-Najjar Syndrome (VALENS), first posted Jul. 21, 2017.
Cohen et al., Effects of phenobarbital on bilirubin metabolism and its response to phototherapy in the jaundiced Gunn rat. Hepatology, Mar.-Apr. 1985; 5(2): 310-6.

(56) References Cited

OTHER PUBLICATIONS

Collaud et al., Efficacy of gene therapy for Crigler-Najjar: optimized adeno-associated viral vector provides persistent correction of hyperbilirubinemia in Gunn rats. Human Gene Therapy, Sep. 2014; 26(9): A14. Presented at 18th Annual Meeting of the American Society of Gene and Cell Therapy, May 9-11, 2015.
Crigler and Najjar, Congenital familial nonhemolytic jaundice with kernicterus. Pediatrics, Aug. 1952; 10(2): 169-80.
Davidoff et al., Sex significantly influences transduction of murine liver by recombinant adeno-associated viral vectors through an androgen-dependent pathway. Blood, Jul. 15, 2003; 102(2): 480-8.
Drucker WD. Glucuronic acid conjugation of tetrahydrocortisone and p-nitrophenol in the homozygous Gunn rat. Proc Soc Exp Biol Med, Oct. 1968; 129: 308-11.
Embury et al., Hepatitis virus protein X-phenylalanine hydroxylase fusion proteins identified in PKU mice treated with AAVWPRE vectors. Gene Ther Mol Biol, Jun. 2008; 12: 69-76.
Erlinger et al., Inherited Disorders of Bilirubin Transport and Conjugation: New Insights Into Molecular Mechanisms and Consequences. Gastroenterology, Jun. 2014; 146(7): 1625-38. Epub Apr. 1, 2014.
European Medicines Agency (EMA). Guideline on follow-up of patients administered gene therapy medicinal products, Oct. 22, 2009, Available at: http://www.ema.europa.eu/docs/en_GB/document_library/Scientific_guideline/2009/11/WC500013424.pdf.
Fagiuoli et al., Monogenic diseases that can be cured by liver transplantation. Journal of hepatology, Sep. 2013; 59(3): 595-612. Epub Apr. 8, 2013.
Fath et al., Multiparameter RNA and codon optimization: a standardized tool to assess and enhance autologous mammalian gene expression. PLoS One, Mar. 3, 2011; 6(3):e17596.
Ferreira et al., Immune Responses to AAV-Vectors, the Glybera Example from Bench to Bedside. Front. Immunol., Mar. 3, 2014; 5: 82.
Fisher et al., Transduction with recombinant adeno-associated virus for gene therapy is limited by leading-strand synthesis. J. Virol., Jan. 1996; 70(1): 520-32.
Fox et al., Treatment of the Crigler-Najjar syndrome type I with hepatocyte transplantation. N Engl J Med, May 14, 1998; 338(20):1422-6.
Gao et al., Biology of AAV serotype vectors in liver-directed gene transfer to nonhuman primates. Mol Ther, Jan. 2006; 13(1): 77-87. Epub Oct. 10, 2005.
Gao G et al., Adeno-Associated Viruses Undergo Substantial Evolution in Primates During Natural Infections. PNAS, May 13, 2003; 100(10): 6081-86. (Epub Apr. 25, 2003).
GenBank Accession NM 000463.2 for *Homo sapiens* UDP glucuronosyltransferase family 1 member A1 (UGT1A1), mRNA, updated Nov. 14, 2015.
Greig et al., AAV8 Gene Therapy for Crigler-Najjar Syndrome in Macaques Elicited Transgene T Cell Responses That Are Resident to the Liver. Mol Ther Methods Clin Dev, Dec. 5, 2018; 11: 191-201.
Greig et al., AAV8 Gene Therapy Rescues the Newborn Phenotype of a Mouse Model of Crigler-Najjar. Hum Gene Ther, Jul. 2018; 29(7): 763-70.
Greig et al., Abstract H-O-003: Determination of the efficacy of a gene therapy approach for the treatment of Crigler-Najjar in the UGT1 KO mouse model, 51st Annual Metting of the European Society for Paediatric Gastroenterology, Hepatology and Nutrition, Apr. 2018.
Greig et al., Abstract H-O-034: Toxicological evaluation of a gene therapy approach for the treatment of Crigler-Najjar in rhesus macaques, 51st Annual Metting of the European Society for Paediatric Gastroenterology, Hepatology and Nutrition, Apr. 2018.
Greig et al., Abstract: Evaluation of Efficacy and Safety in a Dose-Escalating Nonclinical Study of a Clinical Candidate Vector in a Mouse Model of Crigler-Najjar, from the American Society of Gene & Cell Therapy (ASGCT) 20th Annual Meeting, May 10-13, 2017.

Greig et al., Determining the Minimally Effective Dose of a Clinical Candidate AAV Vector in a Mouse Model of Crigler-Najjar Syndrome. Jul. 21, 2018; 10: 237-44.
Gridelli et al. Orthotopic liver transplantation for Crigler-Najjar type I syndrome. Transplantation proceedings, Feb.-Mar. 1997; 29(1-2): 440-1.
Grieger & Samulski, Adeno-associated virus as a gene therapy vector: Vector development, production and clinical applications. Adv. Biochem. Eng. Biotechnol., Aug. 2005; 99: 119-45.
Grimm et al., Titration of AAV-2 particles via a novel capsid ELISA: packaging of genomes can limit production of recombinant AAV-2. Gene Therapy, Jul. 1999; 6(7): 1322-30.
Gunn, Hereditary acholuric jaundice in the rat. Can Med Assoc J, Mar. 1944; 50(3): 230-7.
Gunn. Hereditary acholuric jaundice in a new mutant strain of rats. Journal of Heredity, Apr. 1938; 29(4): 137-9.
Hummel et al., Familial Hypercholesterolemia in a Rhesus Monkey Pedigree: Molecular Basis of Low Density Lipoprotein Receptor Deficiency. PNAS USA, Apr. 1990; 87(8): 3122-6.
Hurlbut et al., Preexisting immunity and low expression in primates highlight translational challenges for liver-directed AAV8-mediated gene therapy. Molecular Ther., Nov. 2010; 18(11): 1983-94. Epub Aug. 24, 2010.
Ip et al., An evidence-based review of important issues concerning neonatal hyperbilirubinemia. Pediatrics, Jul. 2004; 114(1): e130-e153.
Iyanagi et al., The 3-methylcholanthrene-inducible UDP-glucuronosyltransferase deficiency in the hyperbilirubinemic rat (Gunn rat) is caused by a −1 frameshift mutation. J Biol Chem, Dec. 15, 1989; 264(35): 21302-7.
Jansen, Diagnosis and management of Crigler-Najjar syndrome. European Journal of Pediatrics, Dec. 1999; 158: S089-94.
Kadakol et al. Genetic lesions of bilirubin uridine-diphosphoglucuronate glucuronosyltransferase (UGT1A1) causing Crigler-Najjar and Gilbert syndromes: correlation of genotype to phenotype. Human Mutation, Oct. 2000; 16(40): 297-306.
Kamhi et al., AUG sequences are required to sustain nonsense-codon-mediated suppression of splicing, Nucleic Acids Res., Jul. 19, 2006; 34(12): 3421-33.
Kaufman et al. Orthotopic liver transplantation for type I Crigler-Najjar syndrome. Hepatology, 6(6): 1259-62.
Kawashita et al. Hepatic repopulation with stably transduced conditionally immortalized hepatocytes in the Gunn rat. J Hepatol, Jul. 2008; 49(1): 99-106. Epub Apr. 9, 2008.
Kim et al. OPTN/SRTR 2013 annual data report: liver. American Journal of Transplantation, Jan. 27, 2015; 15(S2): 1-28.
Kotin, Large-scale recombinant adeno-associated virus production. Hum Mol Genet, Apr. 15, 2011; 20(R1): R2-6. Epub Apr. 29, 2011.
Labrune, Crigler-Najjar syndrome: Orphanet encyclopedia. Jan. 2004.
Li et al., Cellular immune response to cryptic epitopes during therapeutic gene transfer. PNAS USA, Jun. 30, 2009; 106(26): 10770-4. Epub Jun. 16, 2009.
Li et al., Neutralizing antibodies against adeno-associated virus examined prospectively in pediatric patients with hemophilia. Gene Therapy, Mar. 2012; 19(3): 288-94. Epub Jun. 23, 2011.
Lock et al., Absolute determination of single-stranded and self-complementary adeno-associated viral vector genome titers by droplet digital PCR. Hum Gene Ther Methods, Apr. 2015; 25(2): 115-25. Epub Feb. 14, 2014.
Loeb et al., Enhanced Expression of Transgenes from Adeno-Associated Virus Vectors with the Woodchuck Hepatitis Virus Posttranscriptional Regulatory Element: Implications for Gene Therapy. Human Gene Therapy, Sep. 20, 1999; 10(14): 2295-2305.
MacKenzie and Owens, Differences in UDP-glucuronosyltransferase activities in congenic inbred rats homozygous and heterozygous for the jaundice locus. Biochemical Pharmacology, Dec. 15, 1983; 32(24): 3777-81.
Maguire et al., Safety and efficacy of gene transfer for Leber's congenital amaurosis. The New England Journal of Medicine, May 22, 2008; 358(21): 2240-8.

(56) References Cited

OTHER PUBLICATIONS

Manno et al., Successful transduction of liver in hemophilia by AAV-Factor IX and limitations imposed by the host immune response. Nature Medicine, Mar. 2006, 12(3): 342-7.
McCarty et al., Self-complementary recombinant adeno-associated virus (scAAV) vectors promote efficient transduction independently of DNA synthesis. Gene Therapy, Aug. 2001; 8(16): 1248-54.
McDonagh and Maisels. Bilirubin unbound: déjà vu all over again? Pediatrics, Feb. 2006; 117(2): 523-5.
McLin et al., Blood Pressure Elevation in Long-Term Survivors of Pediatric Liver Transplantation. American Journal of Transplantation, Jan. 2012; 12(1): 183-90. Epub Oct. 12, 2011.
Melton and Akinbi. Neonatal jaundice: strategies to reduce bilirubin-induced complications. Postgraduate Medicine, Nov. 1999; 106(6): 167-78.
Memon et al. Inherited disorders of bilirubin clearance. Pediatric Research, Mar. 2016; 79(3): 378-86. Epub Nov. 23, 2015.
Mietzsch et al., OneBac: platform for scalable and high-titer production of adeno-associated virus serotype 1-12 vectors for gene therapy. Hum Gene Therapy; 25(3): 212-22. Epub Jan. 23, 2014.
Mingozzi and High, Immune responses to AAV vectors: overcoming barriers to successful gene therapy. Blood, Jul. 4, 2013; 122(1): 23-36. Epub Apr. 17, 2013.
Mingozzi and High, Therapeutic in vivo gene transfer for genetic disease using AAV: progress and challenges. Nature Reviews Genetics, May 2011; 12(5): 341-55.
Mingozzi et al., Improved hepatic gene transfer by using an adenoassociated virus serotype 5 vector. J Virol, Oct. 2002; 76(20): 10497-502.
Miyatake et al., Transcriptional Targeting of Herpes Simplex Virus for Cell-Specific Replication. J. Virol., Jul. 1997; 71(7): 5124-32.
Montenegro-Miranda et al., Adeno-associated viral vector serotype 5 poorly transduces liver in rat models. PLOS One, Dec. 27, 2013; 8(12): e82597.
Mukthinuthalapati et al., Incidence, risk factors and outcomes of de novo malignancies post liver transplantation. World Journal of Hepatology, Apr. 28, 2016; 8(12): 533-44. Published online Apr. 28, 2016.
Nakai et al. AAV serotype 2 vectors preferentially integrate into active genes in mice. Nat Genet, Jul. 2003; 34(3): 297-302.
Nathwani et al., Adenovirus-associated virus vector-mediated gene transfer in hemophilia B. New England Journal of Medicine, Dec. 22, 2011; 365(25): 2357-65. Epub Dec. 10, 2011.
Nathwani et al., Long-term safety and efficacy of factor IX gene therapy in hemophilia B. The New England Journal of Medicine, Nov. 20, 2014; 371(21): 1994-2004.
Nazer et al., Crigler-Najjar syndrome in Saudi Arabia. American Journal of Medical Genetics, Dec. 1998; 79:12-15.
NCBI Reference Sequence: YP_077180.1 for capsid protein [Adeno-associated virus-8 ], updated Aug. 23, 2012.
Ng et al., Health status of children alive 10 years after pediatric liver transplantation performed in the US and Canada: report of the studies of pediatric liver transplantation experience. The Journal of Pediatrics, May 2012; 160(5): 820-6.e3. Epub Dec. 20, 2011.
Nguyen et al., Disruption of the ugt1 locus in mice resembles human Crigler-Najjar type I disease. J Biol Chem, Mar. 21, 2008; 283(12): 7901-11. Epub Jan. 7, 2008.
Okayama and Berg. A cDNA cloning vector that permits expression of cDNA inserts in mammalian cells. Mol Cell Biol, Feb. 1983; 3(2): 280-9.
Pasi et al., Interim results of an open-label, phase 1/2 study of BMN 270, an AAV5-FVIII gene transfer in severe hemophilia A. Haemophilia, Jul. 28, 2016; 22(Suppl. 4): 151-2.
Pastore et al. Sustained reduction of hyperbilirubinemia in Gunn rats after adeno-associated virus-mediated gene transfer of bilirubin UDP-glucuronosyltransferase isozyme 1A1 to skeletal muscle. Hum Gene Ther, Oct. 2012; 23(10): 1082-9. Epub Aug. 27, 2012.
Pastore et al., Abstract 353. Ultrasound-Guided Hepatic Injections of HDAd Vector Are More Efficient and Safer Than Systemic Intravenous Injections for Liver-Directed Gene Therapy of Crigler-Najjar Syndrome Type I. Molecular Therapy, May 2013; 21(1): s136.
Pastore et al., Abstract: Development of AAV2/8-Mediated Gene Therapy Clinical Trial for Crigler-Najjar Syndrome Type I: Optimization of Liver-Specific Expression Cassette. Molecular Therapy, Jun. 2013; 21(Suppl. 1): S192-3. Presented at 16th Annual Meeting of the American Society of Gene and Cell Therapy, May 15-18, 2013.
Paterna et al., Influence of Promoter and WHV Post-Transcriptional Regulatory Element on AAV-Mediated Transgene Expression in the Rat Brain Gene Therapy, Aug. 2000; 7(15): 1304-11.
Perretti et al., Clinical utility of electrophysiological evaluation in Crigler-Najjar syndrome. Neuropediatrics, Aug. 2007; 38(4): 173-8.
Porter and Dennis, Hyperbilirubinemia in the Term Newborn. American Family Physician, Feb. 2002; 65(4): 599-606.
Prasad et al., Gene Therapy for Crigler-Najjar Syndrome with AT342, a Liver-Targeted AAV8-UGT1A1 Vector—Preliminary Safety and Efficacy Results from a Phase 1/2 Study (VALENS), from the American Society of Gene & Cell Therapy (ASGCT) 21st Annual Meeting, May 16-19, 2018.
Pratini and Neufeld. Intrathecal baclofen therapy after liver transplant in a patient with Crigler-Najjar syndrome. PM&R 6(2): 196-8. Epub Dec. 21, 2013.
Ronzitti et al. Abstract 547: Untranslated Region Optimization Increases Transgene mRNA and Protein Levels, Resulting in Enhanced Therapeutic Efficacy of AAV Vector Gene Transfer in Vivo for Crigler-Najjar Syndrome. Molecular Therapy, May 2015, 23(Suppl. 1): S219-20. Presented at 18th Annual Meeting of the American Society of Gene and Cell Therapy, May 13-16, 2015.
Rosati et al. Uterine Myoma in Pregnancy: Ultrasound Study. International Journal of Gynecology & Obstetrics, Feb. 1989; 28(2): 109-17.
Sampietro and Iolascon, Molecular pathology of Crigler-Najjar type I and II and Gilbert's syndromes. Haematologica, Feb. 1999; 84(2): 150-7.
Sandig et al., HBV-derived promoters direct liver-specific expression of an adenovirally transduced LDL receptor gene. Gene Ther., Nov. 1996; 3(11): 1002-9.
Schambach et al., Woodchuck hepatitis virus post-transcriptional regulatory element deleted from X protein and promoter sequences enhances retroviral vector titer and expression. Gene Therapy, Apr. 2006; 13(7): 641-5.
Schauer et al., Treatment of Crigler-Najjar type 1 disease: relevance of early liver transplantation. Journal of Pediatric Surgery, Aug. 2003; 38: 1227-31.
Seppen et al., Adeno-associated virus vector serotypes mediate sustained correction of bilirubin UDP glucuronosyltransferase deficiency in rats. Molecular Therapy, Jun. 1, 2006; 13(6): 1085-1092. Epub Apr. 3, 2006.
Servedio et al., Spectrum of UGT1A1 mutations in Crigler-Najjar (CN) syndrome patients: identification of twelve novel alleles and genotype-phenotype correlation. Human Mutation, Mar. 2005; 25(3): 325.
Sherlock and Dooley, Diseases of the liver and biliary system, Eleventh Edition: Chapter 17—Hepatitis B virus and hepatitis delta virus. Blackwell Science, 2002, pp. 285-303.
Skierka et al., UGT1A1 genetic analysis as a diagnostic aid for individuals with unconjugated hyperbilirubinemia. The Journal of Pediatrics, Jun. 2013; 162(6): 1146-52. e1142. Epub Jan. 4, 2013.
Sommer et al., Quantification of Adeno-Associated Virus Particles and Empty Capsids by Optical Density Measurement. Mol. Ther., Jan. 2003; 7(1):122-8.
Son et al., Excision of the first intron from the gonadotropin-releasing hormone (GnRH) transcript serves as a key regulatory step for GnRH biosynthesis. J Biol Chem. May 16, 2003; 278(20): 18037-44. Epub Mar. 13, 2003.
Spark Therapeutics, Spark Therapeutics and Pfizer present updated preliminary data from Hemophilia B Phase 1/2 trial suggesting consistent and sustained levels of Factor IX activity at annual ASH meeting. Spark Therapeutics Press Release. Dec. 2016.

(56) References Cited

OTHER PUBLICATIONS

Strauss et al., Management of hyperbilirubinemia and prevention of kernicterus in 20 patients with Crigler-Najjar disease. Eur J Pediatr, May 2006; 165(5): 306-19. Epub Jan. 25, 2006.
Sundaram et al., Obesity after pediatric liver transplantation: prevalence and risk factors. J Pediatr Gastroenterol Nutr, Dec. 2012; 55(6): 657-62.
Suresh and Lucey, Lack of deafness in Crigler-Najjar syndrome type 1: a patient survey. Pediatrics. Nov. 1997; 100(5): e9.
Takahashi et al., Long term correction of bilirubin-UDP-glucuronosyltransferase deficiency in Gunn rats by administration of a recombinant adenovirus during the neonatal period. J Biol Chem, Oct. 25, 1996; 271(43): 26536-42.
Thomas et al., Scalable recombinant adeno-associated virus production using recombinant herpes simplex virus type 1 coinfection of suspension-adapted mammalian cells. Hum Gene Ther, Aug. 2009; 20(8): 861-70.
Thompson et al., A comprehensive comparison of multiple sequence alignments. Nucl. Acids. Res., Jul. 1, 1999; 27(13): 2682-90.
Tukey and Strassburg, Human UDP-glucuronosyltransferases: metabolism, expression, and disease. Annual Review of Pharmacology and Toxicology, Apr. 2000; 40: 581-616.
U.S. Department of Health and Human Services, Food and Drug Administration, Guidance for Industry: Gene therapy clinical trials observing subjects for delayed adverse events. Nov. 2006.
U.S. Department of Health and Human Services, Food and Drug Administration, Guidance for Industry: Preclinical Assessment of Investigational Cellular and Gene Therapy Products, Nov. 2013.
USPI for prednisolone. Oct. 2013.
Van Der Veere et al., Current therapy for Crigler-Najjar syndrome type 1: report of a world registry. Hepatology, Aug. 1996; 24:311-15.
Van Dijk et al., Polyinosinic acid blocks adeno-associated virus macrophage endocytosis in vitro and enhances adeno-associated virus liver-directed gene therapy in vivo. Hum Gene Ther., Sep. 2013; 24(9): 807-13.
Virag et al., Producing Recombinant Adeno-Associated Virus in Foster Cells: Overcoming Production Limitations Using a Baculovirus—Insect Cell Expression Strategy. Hum Gene Therapy, Aug. 2009; 20(8): 807-17.
Wang et al. AAV8-mediated hepatic gene transfer in infant rhesus monkeys (*Macaca mulatta*). Mol Ther, Nov. 2011; 19(11): 2012-20. Epub Aug. 2, 2011.
Wang et al., Hepatic gene transfer in neonatal mice by adeno-associated virus serotype 8 vector. Hum Gene Ther, May 2012; 23(5): 533-9. Epub Feb. 8, 2012.
Wang et al., Immune Responses to AAV in Canine Muscle Monitored by Cellular Assays and Noninvasive Imaging. Molecular Therapy, Mar. 2010; 18(3); 617-24. Epub Dec. 29, 2009.
Wang et al., Impact of Pre-Existing Immunity on Gene Transfer to Nonhuman Primate Liver with Adeno-Associated Virus 8 Vectors. Hum Gene Ther, Nov. 2011; 22(11): 1389-401.
Wang et al., Sustained Expression of Therapeutic Level of Factor IX in Hemophilia B Dogs by AAV-Mediated Gene Therapy in Liver. Molecular Therapy, 2000; 1(2): 154-8.
Wang et al., The Pleiotropic Effects of Natural AAV Infections on Liver-directed Gene Transfer in Macaques, Mol Ther, Jan. 2010; 18(1): 126-34.
Wickremasinghe et al., Neonatal Phototherapy and Infantile Cancer. Pediatrics, Jun. 2016; 137(6): e20151353.
Wobus et al., Monoclonal antibodies against the adeno-associated virus type 2 (AAV-2) capsid: epitope mapping and identification of capsid domains involved in AAV-2-cell interaction and neutralization of AAV-2 infection. J. Virol., Oct. 2000; 74(19): 9281-93.
Wu et al., Optimization of Self-complementary AAV Vectors for Liver-directed Expression Results in Sustained Correction of Hemophilia B at Low Vector Dose. Molecular Therapy, Feb. 2008, 16(2): 280-9. Epub Dec. 4, 2007.
Yan et al., Human thyroxine binding globulin (TBG) promoter directs efficient and sustaining transgene expression in liver-specific pattern. Gene, Sep. 1, 2012; 506(2): 289-94.
Yang et al., A dual AAV system enables the Cas9-mediated correction of a metabolic liver disease in newborn mice. Nat Biotechnol, Mar. 2016; 34(3):334-8. Epub Feb. 1, 2016.
Ye et al., Herpes simplex virus clearance during purification of a recombinant adeno-associated virus serotype 1 vector. Hum Gene Ther Clin Dev, Dec. 2014; 25(4): 212-7.
Zhang et al., Adenovirus-adeno-associated virus hybrid for large-scale recombinant adeno-associated virus production. Human Gene Ther, Sep. 2009; 20(9): 922-9.
International Search Report and Written Opinion issued for International Application No. PCT/US2016/066657, dated May 9, 2017.
International Search Report and Written Opinion issued for International Application No. PCT/EP2015/059099, dated Nov. 11, 2015.
Giles AR et al., Deamidation of Amino Acids on the Surface of Adeno-Associated Virus Capsids Leads to Charge Heterogeneity and Altered Vector Function, Mol. Ther., Dec. 5, 2018; 26(12):2848-2862. Epub Oct. 18, 2018.
Examination Report issued in European Patent Application No. 16825943.0, dated Nov. 27, 2019.
Applicant's Response to Examination Report in European Patent Application No. 16825943.0, filed Jun. 4, 2020.

* cited by examiner

FIG. 10A (A)

| | |
|---|---|
| U201DP | gcccctgacgcgccagcctgtacatccgggacggagcctt ctacacc ctgaagacctaccct |
| U001 | gcccccgacgcgccagcctgtacatccgggacggagcctt ctacacc ctgaagacctacccc |
| U011TY | gctcccgacgctagcctgtacctgtacattcgggacggcgcgctttt acacc ctgaagacctacccc |
| UGT1A1v3 | gcccctgatgcgccagcctgtacatcagagatggcgcgctt ctacaac ctgaagacctaccct |
| UGT1A1co | gcccctgacgcgccagcctgtacatcagagatggcgcgcctt ctacacc ctgaaaacctaccccc |
| UGT1A1v2.1 | gccccgagacgcttcccctgtatattcgggacggagcgttctacactctcaagacctaccct |
| | *  ***  *  *  *****  *  *  ****  *  *  *  *  *  ***  *  *   *******  |

| | |
|---|---|
| U201DP | gtgcccttccagcgggaggacgtgaaggagagcttcgtgagcctgggacacaacgtgttc |
| U001 | gtgcccttccagcgggaggacgtgaaggagagcttcgtgagcctgggcacaacgtgttc |
| U011TY | gtgcccttcagcgggaggacgtgaaggagagcttcgtgagcttgtgagctgggccacaacgtgttc |
| UGT1A1v3 | gtgcccttccagcgggagcgcgaggacgtgaaagaaagcttcgtgcccctgggccacaacgtgttc |
| UGT1A1co | gtgcccttccagcgggagcgcgaggacgtgaaagaaagcttcgtgcccctgggccacaacgtgttc |
| UGT1A1v2.1 | gtcccctccaaagggaggaggacgtgaaggaaagcgtgaagagcttgtgctgggcataatgtgttc |
| | **  ******  **  ****  **  *  ***  *  **  *****  |

FIG. 10A (continued)

```
U201DP      ctgcaccagaaccctctgagccaggagttcgaggcctacatcaacgccagcggagagcac
U001        ctgcaccagaaccccctgagccaggagttcgaggcctacatcaacgccagcggggagcac
U011TY      ctgcaccagaaccccctgagccaggaatttgaagcttaacttaagcgaacac
UGT1A1v3    ctgcaccagaaccccctgagccaggaatttgaggcctacatcaacgccagcggcgagcac
UGT1A1co    ctgcaccagaaccctgagccaggagtttgaggcctacatcaacgccagcggcgagcac
UGT1A1v2.1  ctgcatcaaaaccactgagccaggagttgaggcgtacatcaacgcctcgggagagcat
            ***   ** **  **  *******  * ** *  **  **  ** ***     ***   .

U201DP      ggaatcgtggtgttcagcctggggaagcatggtgagcgagatccctgagaagaaggccatg
U001        gggatcgtggtgttcagcctggggagcatggtgagcgagatcccctgagaagaaggccatg
U011TY      ggcatggtgttgtttagcctggcagcagcatggtgagcgagatccccgagaagaaggccatg
UGT1A1v3    ggcatcgtggtgttcagcctgggcagcagcatggtgagcgagatccccgaaaatccccgagaagaaggcctatg
UGT1A1co    ggcatcgtggtgttcagcctgggcagcagcatggtcgagatccccgagaaaaggccatg
UGT1A1v2.1  ggaatcgtggtgttctccccctccggttccatggtccatggtccatggtagaaaggcaatg
            ** ** ** ** ** **  ****    *** **  * ***  *   *   * **** *.

U201DP      gccatcgccgacgccctgggaagatccctcagaccgtgtgcggcggtacaccggaacc
U001        gccatcgccgacgccctgggaaagatcccccagaccgtgtgcggcggtacaccggacc
U011TY      gctattgctgacgctctgggcaagatccccagaccgtgtctgcggtacaccggacc
UGT1A1v3    gctatcgccgacgccctgggcaagatcccccagaccgtgtgcggcggtacaccggacc
UGT1A1co    gctatcgccgacgccctgggcaagatcccccagaccgtgtgcggcggtacaccggacc
UGT1A1v2.1  gccatcgcagatgccctgggcaaaatcccgcagaccgtgtgcggcgtctgggcgtacacgggtact
            ** **  * *** *  **  ** ** **  ***** **   *    * * **    *
```

FIG. 10C (continued)

```
U201DP     gccaagcggatggagaccaagggagccggagtgaccctgaacgtgctggagatgaccagc
U001       gccaagcggatggagaccaagggagccggggtgaccctgaacgtgctggagatgaccagc
U011TY     gctaagcggatggagaccaaggaaaacaaggggccgggtgaccctgaacgtgctggaaatgaccagc
UGT1A1v3   gccaagcggatggagaccaaggaaaacaaggggcgctggcgtgaccctgaacgtgctggaaatgaccagc
UGT1A1co   gccaagcggatggagaccaaggaaaacaaggggcgctggcgtgaccctgaacgtgctggaaatgaccagc
UGT1A1v2.1 gcaaaagaatggaaaccaaggaaaacaaggggccggagtgacgctgaacgtgcttgaaatgacctcg
           *  *  *   *  **.*.**.**   ***       **  *** ***** **  * ** ****.*;

U201DP     gaggacctggagcagcgccctgaaggccgtgaaggccgtgatcaacgacaaggagaacatc
U001       gaggacctggagcagcgccctgaaggccgtgaaggccgtgatcaacgacaaggagaacatc
U011TY     gaagacctggagcagcgctctgaaggctgtgtgaaggccgtgattaacgacaaggagaaaacatt
UGT1A1v3   gaggacctggagcagcgccctgaaggccgtgaaggccgtgatcaacgacaaggagaaaacatc
UGT1A1co   gaggacctggagcagcgccctgaaggccgtgaaggccgtgatcaacgacaaggagaaaacatc
UGT1A1v2.1 gaagatctggagcagcgctctcaaagcggtgatcaacgtcctacaagaagaaacatc
           **  * ****** *  *  **   *    **  * **  ** ***; **** *** ****.

U201DP     atgcggctgagctgccagcctgcacaagggccctggagcctctggacctggccctgttc
U001       atgcggctgagcgagcagcctgcacaagggccctggagcctctggagcctggccctgttc
U011TY     atgcggctgagcgagcagcctgcacaagggcctggagccccgggaaccctggacctggctgttt
UGT1A1v3   atgcggctgtccagcctgcacaagggcctggagcccgggaccctggacctggccgtgttc
UGT1A1co   atgcggctgtccagcctgcacaagggcctggagcccgggaccctggacctggccgtgttc
UGT1A1v2.1 atgcggctgagctccctccacaagggcctggagcccgggaccagtgaccgctgcggtcttt
           ********    ***  *.  *;  ****** *  *   *     *   *     *  ** **
```

FIG. 10D (continued)

```
U201DP      tgggtggagttcgtgatgcggcacaaggagcccctcacctgcggcctgccgcccacgac
U001        tgggtggagttcgtgatgcggcacaaggagcccctcacctgcggcctgccgcccacgac
U011TY      tgggtggaattgtgatgcggcacaaggggggcacaaggggcgctcacctgcggccccacgac
UGT1A1v3    tgggtggaattcgtgatgcggcacaagggcgctcccacctctgaggcgctgctcacgac
UGT1A1co    tgggtggaattcgtgatgcggcacaagggcgctccccatctgaggcctgcagctcacgac
UGT1A1v2.1  tgggtggagttcgtgatgaggcacaagggcgccccccacctcagacccgcagctcacgac
            *******  * **  ******* ***** **    * *** ** ** **  *** ***

U201DP      ctgacctggtaccagtaccacacagcctggacgtgatcggattcctgcctggccgtggtctg
U001        ctgacctggtaccagtaccacacagcctggacgtgatcgatcctgctggccgtggtgctg
U011TY      ctgacctggtaccagtaccacacagcctggacgtgatcggtgatcggttcctggccgtggtgctg
UGT1A1v3    ctgacctggtatcagtaccacacagcctggacgtgattggcttctgctggcttgctggtgctg
UGT1A1co    ctgacctggtatcagtaccacacagcctggacgtgatcggcttcctgctggcagtggtgctg
UGT1A1v2.1  ctcacttggtaccagtaccattcgctgtcatcgctgatgtcatcggcttctcctggcggtcgtgctc
            ** ** **** *** ***      *  ** ** * **  ** ** *  **  *  ** **

U201DP      accgtggccttcatcacccttcaagtgctgcgcctacggagaagtgcctgggaaag
U001        accgtggccttcatcacccttcaagtgctgcgcctacggagaagtgcctgggaaag
U011TY      accgtggcctttattacccttaagtgtgtgcgcctacggcttacggaagtgcctgggcaag
UGT1A1v3    accgtggccttcatcacccttcaagtgctgcgcctacggctacggaagtctgcctgggcaag
UGT1A1co    accgtggccttcatcacccttcaagtgctgcgcctacggctacggaagtgcctgggcaag
UGT1A1v2.1  accgtggcgttcatcacccttcaagtgctgcgcgatatcgcgcctacggatatcgcaaatgcaaagtgcttgggaag
            ******  *   **  *  **  ***** **  * *** * ***  *** ** **
```

COMPOSITION FOR TREATMENT OF CRIGLER-NAJJAR SYNDROME

INCORPORATION-BY-REFERENCE OF MATERIAL SUBMITTED IN ELECTRONIC FORM

Applicant hereby incorporated by reference the Sequence Listing material filed in electronic form herewith. The file is labelled "UPN_16-7685PCT_ST25.txt".

BACKGROUND OF THE INVENTION

Crigler-Najjar (CN) syndrome is an autosomal recessive disorder of bilirubin metabolism that is caused by a variety of alterations in the coding sequence of the uridine diphosphate glucuronosyl transferase 1A1 (UGT1A1) gene. The total loss of UGT1A1 activity and the resulting severe jaundice and risk of neurological sequelae (kernicterus) are associated with CN type I. Although several drugs can slightly reduce jaundice, most current medical management relies on phototherapy for at least 12 hours per day. However, phototherapy rapidly becomes less effective following puberty, increasing the risk for kernicterus, and resulting in the need for liver transplantation to control the disease. Liver transplantation is not optimal, as it is risky for the patient and requires immune suppression. Additionally, since these patients sometimes require liver transplantation by the age of 10-13, multiple transplants may be required throughout the course of their lives.

Different animal models of the disease exist, including the natural occurring Gunn rat and a more recent knock-in mouse model of the diseases, which carries the same mutation present in the Gunn rat (Bortolussi et al., *FASEB J.*, 2012, 26:1052-1062). Gunn rats present high bilirubin levels in serum and they have cerebellar hypoplasia; CN mice have a much more severe phenotype and die soon after birth if not promptly treated with phototherapy or gene therapy (Bortolussi et al., *FASEB J.*, 2012, 26:1052-1062). Prior studies aimed at developing a gene-based therapy for CN showed that therapeutic efficacy could be achieved using adeno-associated virus (AAV) vectors delivered to the liver (Bortolussi et al, *FASEB J.*, 2012, 26:1052-1062; Seppen et al., *Molecular Therapy*, 2006, 13(6):1085-1092). Botolussi et al, cited above, describe a study in a lethal mouse model of CN syndrome and reports that as low as 5 to 8% of normal liver expression and activity levels of UGT1A1 were sufficient to significantly reduce bilirubin levels and maintain lifelong low plasma bilirubin concentration.

CN type II is characterized by unconjugated hyperbilirubinemia due to reduced and inducible activity of hepatic bilirubin glucuronosyltransferase. Similarly, Gilbert syndrome is characterized by unconjugated hyperbilirubinemia caused by the reduced activity of glucuronyl transferase.

Therapies for treatment of CN syndrome type I and II, as well as Gilbert syndrome, and/or for delaying the earliest age of the subject in the absence of or in addition to the failure of liver transplantation are needed in the field.

SUMMARY OF THE INVENTION

The invention features a polynucleotide (e.g., a DNA or RNA molecule) encoding UGT1A1 (e.g., a UGT1A1 coding sequence, e.g., a polynucleotide that expresses human UGT1A1).

In another aspect, a vector (e.g., an adeno-associated virus (AAV) vector (e.g., an AAV8 vector)) is provided. In some embodiments, the AAV vector comprises a vector genome having AAV inverted terminal repeat sequences (ITRs) and a UGT1A1 coding sequence (e.g., a nucleic acid sequence comprising a UGT1A1 coding sequence). The UGT1A coding sequence can be operably linked to one or more expression control sequences (e.g., one or more expression control sequences comprising a liver-specific promoter). In some embodiments, the AAV vector (e.g., the AAV8 vector) has a vector genome having a heterologous secretion signal substituted for a native secretion signal. The vector genome may have multiple enhancers.

In one aspect, a UGT1A1 coding sequence useful in composition and methods for treating diseases associated with loss of UGT1A1 function, including, e.g., Crigler Najjar (CN) Syndrome I, CN II, and Gilbert syndrome, are provided. The sequences are selected from: (a) SEQ ID NO: 12; (b) SEQ ID NO: 14; (c) SEQ ID NO: 13; (d) SEQ ID NO: 4; (b) SEQ ID NO: 3; (c) SEQ ID NO: 2; or (d) SEQ ID NO: 1; its complementary strand, corresponding RNA, or a sequence 99% identical thereto which expresses human UGT1A1.

In another aspect, the invention provides a vector having a vector genome comprising a UGT1A1 coding sequence as identified herein operably linked to expression control sequences which direct transcription and/or expression of human UGT1A1. In certain embodiments, the vector is an adeno-associated virus (AAV). In still other embodiments, the vector has an AAV8 capsid. In certain embodiments, the expression control sequences comprise a liver-specific promoter.

In still other embodiments, a composition comprising a vector as described herein is provided in a formulation buffer. In a further aspect, a composition is provided which comprises an AAV vector of any of the preceding embodiments in a formulation buffer (e.g., a formulation buffer including phosphate buffered saline and a surfactant). In some cases, the AAV vector carries a gene encoding a human UGT1A protein and a pharmaceutically acceptable excipient, carrier, buffer, or preservative.

In another aspect, any of the preceding AAV vectors (e.g., AAV8 vectors) and/or compositions may be for use in treating a patient or patients having Crigler-Najjar (CN) syndrome (e.g., CN syndrome type I or CN syndrome type II) or Gilbert syndrome. In some cases, the patient is co-treated with an immunosuppressive and/or a phototherapy.

In certain embodiments, use of UGT1A1 coding sequence in treating Crigler-Najjar syndrome type I or II, or Gilbert syndrome with a UGT1A1 coding sequence described herein. In a further aspect, a composition is provided which comprises an AAV carrying a gene encoding a human UGT1A protein and a pharmaceutically acceptable excipient, carrier, buffer or preservative.

In still another aspect, a composition is provided which contains a rAAV vector as described herein for treatment of Crigler-Najjar syndrome type I or II, or Gilbert syndrome. Also described are methods of treatment Crigler-Najjar syndrome type I or II, or Gilbert syndrome. In certain embodiments, patient is co-treated with an immunosuppressive and/or phototherapy.

BRIEF DESCRIPTION OF THE DRAWINGS

FIG. 6A shows hUGT1A1 RNA copies presented per 100 ng of RNA. FIG. 6B shows Corrected relative expression of hUGT1A1 RNA levels. Values plotted as mean±SEM (n=3 liver samples/animal).

Figure 10E:
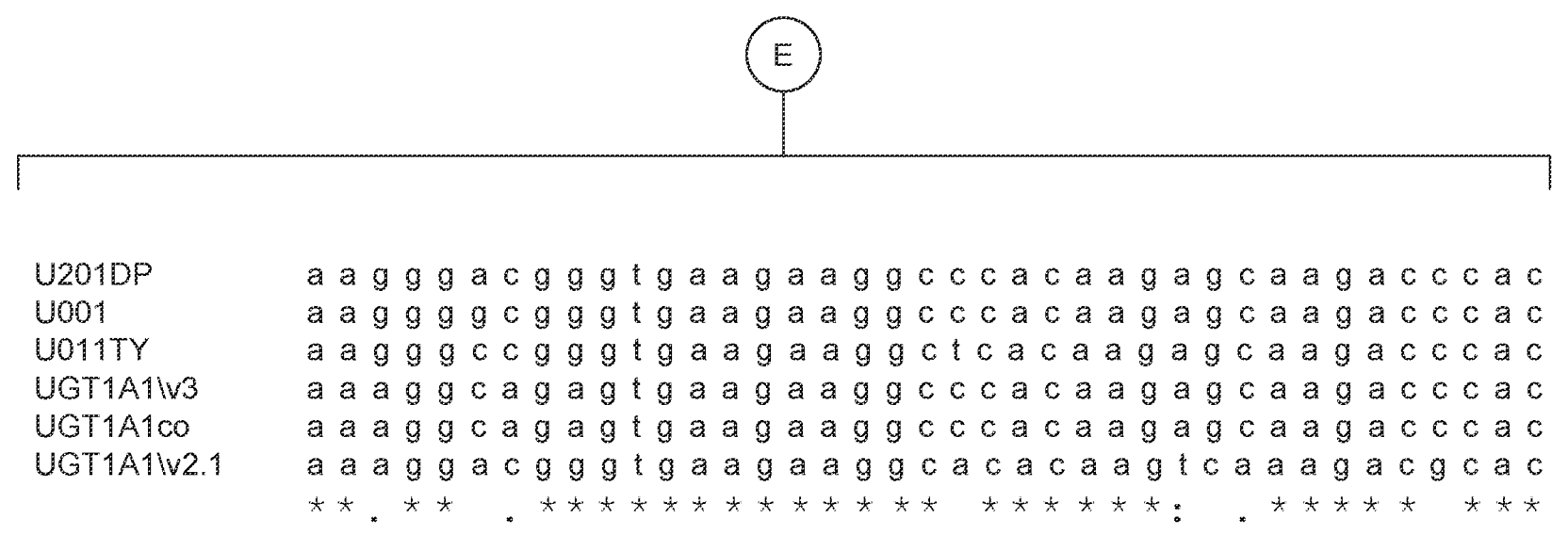

FIG. 10A-10E provide an alignment of the novel UTG1A1 coding sequences provided herein: U201DP [SEQ ID NO: 3], U001 [SEQ ID NO: 1], U011TY [SEQ ID NO: 2], and UGT1A1co [SEQ ID NO: 4], with two published UGT1A1 sequence, termed v2.1 [SEQ ID NO: 7] and v3 [SEQ ID NO: 8].

DETAILED DESCRIPTION OF THE INVENTION

Figure 1:
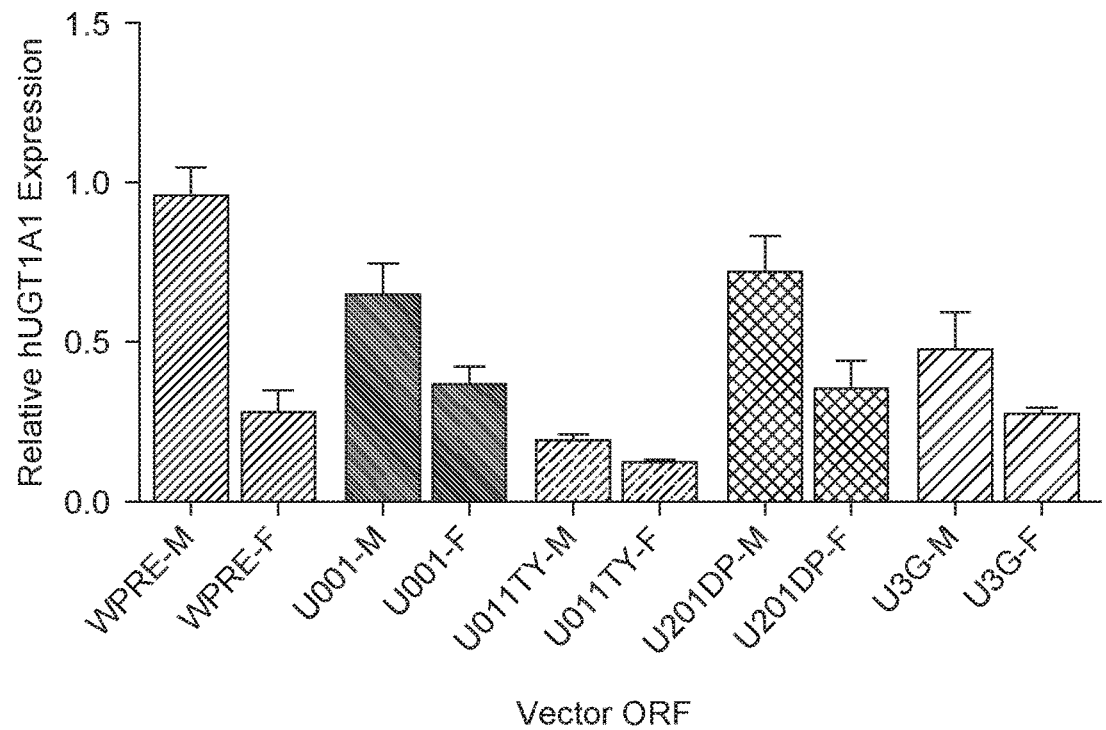
FIG. 1 is a quantification of Western blots for hUGT1A1 expression in liver homogenates from AAV-administered C57BL/6 mice. Male and female C57BL/6 mice were injected IV via the tail vein with $3 \times 10^{12}$ genome copies (GC)/kg of vectors expressing hUGT1A1 from a variety of vectors having different codons and different CpG less nucleotide sequences. At necropsy, livers were harvested and liver homogenates made. 1 µg of protein isolated from liver homogenate was run by Western blot with a human UGT1A1-specific antibody used for detection. Images of bands were quantified against the same amount of protein from a positive control sample. Values plotted as mean±SEM (n=5 mice/group). M, male; F, female; WPRE, denotes the first generation vector AAV8.TBG.hUGT1A1co.WPRE.BGH.
Figure 2:
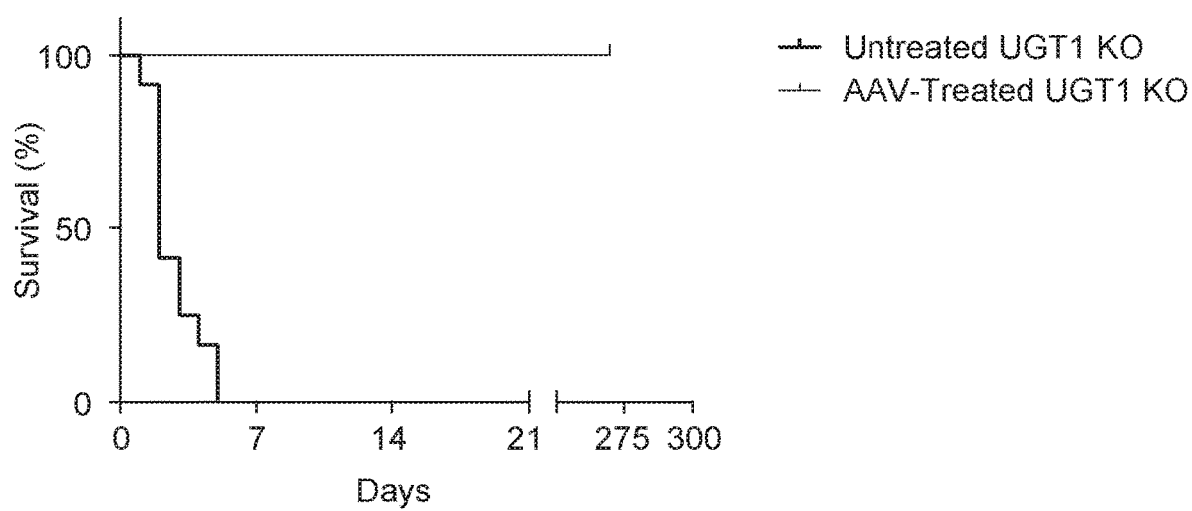
FIG. 2 is a survival chart showing untreated UGT1 knock-out (KO) mice (none of which survived to day 7) and AAV-treated UGT1 knock-out mice following IV injection of test article into UGT1 KO mice within 24 hours of birth. Untreated UGT1 KO mice were observed daily from the time of birth. Mice either found dead or euthanized for clinical signs were genotyped. Treated UGT1 KO mice were injected IV with $10^{11}$ GC/mouse of AAV8.TBG.hUGT1A1co.WPRE.BGH.

This invention relates to the use of a replication deficient adeno-associated virus (AAV) to deliver a UGT1A1 gene to liver cells of patients (human subjects) diagnosed with Crigler-Najjar (CN) syndrome I or II, or Gilbert syndrome. The recombinant AAV vector (rAAV) used for delivering the UGT1A1 gene ("rAAV.UGT1A1") should have a tropism for the liver (e.g., an rAAV bearing an AAV8 capsid). The transgene may be controlled by liver-specific expression control elements. Such rAAV.UGT1A1 vectors can be administered by intravenous (IV) infusion to achieve therapeutic levels of UGT1A1 protein expression in the liver. Therapeutically effective doses of the rAAV.UGT1A1 range from greater than 2.5×10¹⁰ to 2.5×10¹³ genome copies (GC)/kg body weight of the patient, In one embodiment, the rAAV suspension has a potency such that a dose of at least 2.5×10¹¹ GC/kg administered to a mouse model of CN provided a reversal of total bilirubin levels to baseline levels. In another embodiment, the rAAV suspension has a potency such that a dose of at least 2.5×10¹² GC/kg administered to a human subject in need thereof provided a therapeutically effective lowering of total bilirubin levels. Optionally, the subjects are administered immunosuppressive agents in conjunction with therapy.

The terms "treat," "treating," and "treatment" refer to reducing the progression of some or all symptoms, reducing the severity of some or all symptoms, or to prevent or delay the onset of some or all symptoms.

The goal of the treatment is to functionally replace the patient's defective UGT1A1 via rAAV-based liver-directed gene therapy to treat this disease and improve response to current treatments. The invention is based, in part, on the development of therapeutic compositions and methods that allow for the safe delivery of efficacious doses; and improved manufacturing methods to meet the purification production requirement for efficacious dosing in human subjects.

Efficacy of the therapy may be assessed after treatment, e.g., post-dosing, using total bilirubin levels and/or serum bilirubin levels as a surrogate biomarker for human UGT1A1 transgene expression in the patient. For example, a decrease in the total bilirubin levels or serum bilirubin levels after the gene therapy treatment would indicate the successful transduction of functional UGT1A1. Patients who are candidates for treatment include neonates, infants, children and adults (male or female≥18 years of age) diagnosed with CN Syndrome I or II. Prior to treatment, the patient may be assessed for neutralizing antibodies (NAb) to the AAV serotype used to deliver the UGT1A gene. Additionally, or alternatively, patients are monitored for elevated liver enzymes, which may be treated with transient immunosuppressant therapy (e.g., if at least about 2× baseline levels of aspartate transaminase (AST) or alanine transaminase (ALT) are observed).

As used herein, the term wild-type "UGT1A1" refers to the wild-type human UDP-glycosyltransferase 1 family 1, polypeptide A, (UGT1A1) cDNA shown in SEQ ID NO: 5 (accession number NM 000463.2, that is the reference sequence for the CDS of the mRNA for UGT1A1 human; OMIM reference 191740). The encoded enzyme is shown in SEQ ID NO: 6.

Provided herein are nucleic acid sequences encoding the UGT1A1 enzyme having sequences which are less than 95% identical to human wild-type sequence, SEQ ID NO:5. More particularly, sequences provided herein may be less than 90% identical, less than 85% identical, less than 80% identical, or as low as about 60% identical, or about 70% to 95% identical to the human wild-type sequence.

In one embodiment, the human UGT1A1 coding sequence is selected from U001 [SEQ ID NO: 1], U001mod [SEQ ID NO: 13], U011TY [SEQ ID NO: 2], U011TYmod [SEQ ID NO: 14], U201DP [SEQ ID NO: 3], U201DPmod [SEQ ID NO: 12], or the sequence of SEQ ID NO: 4. In certain embodiments, sequences having at least 99% identity to one of SEQ ID NO: 1-4, 12-14, these sequences may be used in a vector as described herein.

In certain embodiments, the engineered hUGT1A1 coding sequence selected for the vector genome is that of SEQ ID NO: 4. Suitably, this sequence has less than about 80% identity to wild-type human UGT1A1 gene [reproduced in SEQ ID NO:5], and less than about 95% identity or 90% identity, respectively to previously published engineered sequences. The sequence provided herein is particularly well suited for AAV8-mediated delivery and expression from the vector genome illustrated in the examples herein.

In certain embodiments, the UGT1A1 coding sequence is SEQ ID NO: 12. This sequence has about 99% identity to SEQ ID NO: 3. However, this sequence is less than about 85% identical to the wild-type human UGT1A1 gene [reproduced in SEQ ID NO:5], and less than about 95% identity, respectively to previously published engineered sequences. The sequence provided herein is particularly well suited for AAV8-mediated delivery and expression from the vector genome illustrated in the examples herein.

In certain embodiments, a vector genome as provided herein comprises AAV 5' ITR, two enhancers, a promoter, an intron, a linker sequence, the CN coding sequence, a polyA, and an AAV 3' ITR. In certain embodiments, the ITRs are from AAV2, which is a source different from the AAV capsid (e.g., AAV8). In certain embodiments, the two enhancers are two copies of the same enhancer, e.g., alpha mic/bik. In certain embodiments, the promoter is a liver-specific promoter (e.g., a TBG promoter). In certain embodiments, the vector genome further comprises a Kozak sequence. In certain embodiments, the polyA is a bovine growth hormone polyA. Illustrated vector genomes are provided herein as nt 1 to 3558 of SEQ ID NO: 9, nt 1 to 3153 of SEQ ID NO: 10, nt 1 to 3140 of SEQ ID NO: 15 [AAV.TBG.U201DPmod.BGH], nt 1 to 3140 of SEQ ID NO: 16 [AAV.TBG.U011TYmod.BGH], nt 1 to 3140 of SEQ ID NO: 17 [AAV.TBG.U001mod.BGH]. These sequence provided herein is particularly well suited for AAV-mediated delivery, and in particularly, AAV8-mediated delivery. For example, AAV8-based vector, AAV8.TBG.U201DPmod.BGH is illustrated as the second-generation vector in the examples (i.e., AAV8.TBG.hUGT1A1co in figures/figure legends of FIGS. 6-9;) and the AAV8-based vector having the vector genome of nt 1-3153 of SEQ ID NO: 10 is illustrated in the studies shown in FIGS. 1-5.

As used herein, the term "NAb titer" refers to a measurement of how much neutralizing antibody (e.g., anti-AAV NAb) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

The terms "percent (%) identity", "sequence identity", "percent sequence identity", or "percent identical" in the context of nucleic acid sequences refers to the bases in the two sequences which are the same when aligned for correspondence. The length of sequence identity comparison may be over the full-length of the genome, the full-length of a gene coding sequence, or a fragment of at least about 500 to 5000 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, a "functional fragment" refers to a portion of a referenced polynucleotide or a sequence having at least 95% (e.g., at least 99%) identity to the referenced sequence, which is sufficient to treat a UGT1A1-associated disease symptom in a human or a knockout mouse.

The expression cassette typically contains a promoter sequences as part of the expression control sequences. In one embodiment, a tissue-specific promoter is selected. As used herein, "a tissue-specific promoter" is a promoter which has activity in only a single type of tissue or a selected subset of cell types. This contrasts with constitutive promoters which direct expression in virtually all tissues and are largely, if not entirely, independent of environmental and developmental factors. Promoter activity can be evaluated by assessing transcription levels of the gene operably linked to the promoter as compared to at least one reference tissue (e.g., by detecting mRNA levels using PCR techniques) and/or by assessing expression levels of the gene product in the target tissue as compared to at least one reference tissue. Thus, one may be able to determine that a given promoter is tissue-specific by either its lack of activity in at least one reference tissue and/or by its activity in the selected tissue as compared to at least one reference tissue. A variety of assays are known in the art for assessing transcription and expression levels. Thus, for a "liver-specific promoter", activity levels above an assay baseline may be detected in liver, whereas if assessed in another reference tissue, no activity is detected. Specificity may vary among promoters. There may be tissue-specific promoters which exhibit no detectable transcription or expression in other tissues, whereas some may exhibit higher transcription and/or expression levels in the target tissue (e.g., at least 10% to 100%, at least 25% higher, at least 30% higher, at least 50% higher, at least 75% higher, at least 80% higher, at least 90% higher, and amounts therebetween), as compared to at least one reference tissue. In certain embodiments, muscle may be selected as reference tissue for comparison to a suspected "liver-specific promoter" (e.g., TBG). In certain embodiments of the invention, a liver-specific promoter is selected. See, e.g., The Liver Specific Gene Promoter Database, Cold Spring Harbor, http://rulai.schl.edu/LSPD or https://cbl.utdallas.edu/-LSPD/index. Liver specific promoters include, thyroxin binding globulin (TBG), alpha 1 anti-trypsin (A1AT); human albumin Miyatake et al., J. Virol., 71:5124 32 (1997), humAlb; and hepatitis B virus core promoter, Sandig et al., Gene Ther., 3:1002 9 (1996)]' TTR minimal enhancer/promoter, alpha-antitrypsin promoter, and LSP (845 nt) (requires intron-less scAAV), alcohol dehydrogenase 1, alcohol dehydrogenase 2, alcohol dehydrogenase 3, alcohol dehydrogenase 4, aldolase B, alpha fibrinogen, alpha-1-Microglobulin/bikunin (mic/bik) precursor, alpha-2-macroglobulin, alpha-2-urinary globulin, alpha-fetoprotein, angiotensinogen, antithrombin, antithrombin iii, apolipoprotein A-I, apolipoprotein A-II, apolipoprotein B, apolipoprotein C-III, apolipoprotein E, arginase, aromatic L-amino acid decarboxylase, beta fibrinogen, biliary glycoprotein. C-reactive protein, C4b-binding protein alpha-chain, carbamoylphosphate synthetase I, catechol-O-methyltransferase, complement component C6, cytochrome P450 2E1, erythropoietin, factor IX, factor VII, factor VIII, factor X, gamma fibrinogen, glucose-6-phosphatase, haptoglobin, hepatic lipase, insulin receptor, insulin-like growth factor binding protein I, insulin-like growth factor II, medium-chain acyl-CoA dehydrogenase, multidrug-resistance protein 2, protein C inhibitor, protein C, serum amyloid A, thyroxine-binding globulin, transferrin, and vitamin D binding protein. Alternatively, other promoters, such as viral promoters, constitutive promoters, regulatable promoters [see, e.g., WO 2011/126808 and WO 2013/04943], or a promoter responsive to physiologic cues may be used may be utilized in the vectors described herein.

In addition to a promoter, an expression cassette and/or a vector may contain other appropriate transcription initiation, termination, enhancer sequences, efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. Examples of suitable polyA sequences include, e.g., SV40, bovine growth hormone (bGH), and TK polyA. Examples of suitable enhancers include, e.g., the alpha fetoprotein enhancer, the TTR minimal promoter/enhancer, LSP (TH-binding globulin promoter/alpha1-microglobulin/bikunin enhancer), amongst others. In one embodiment, the expression cassette further contains a woodchuck hepatitis virus post-transcriptional regulatory element (WPRE). In other embodiments, the vectors contain no WPRE element. In still other embodiments, the vector has been modified to reduce CpG-sites.

In one embodiment, the expression cassette comprises an intron, e.g., an intron placed between the promoter and the coding sequence. An intron may be introduced to increase mRNA stability, 5' capping, and the production of the protein. In a particular embodiment, the nucleic acid construct comprises a chimeric Promega intron. Other introns may include, e.g., human beta globin b2 (or HBB2) intron, a coagulation factor IX (FIX) intron, a SV40 intron or a chicken beta-globin intron.

These control sequences are "operably linked" to the UGT1A1 gene sequences. As used herein, the term "operably linked" refers to both expression control sequences that are contiguous with the gene of interest and expression control sequences that act in trans or at a distance to control the gene of interest.

The expression cassette may be engineered onto a plasmid which is used for production of a viral vector. The minimal sequences required to package the expression cassette into an AAV viral particle are the AAV 5' and 3' inverted terminal repeats (ITRs), which may be of the same AAV origin as the capsid, or which of a different AAV origin (e.g., to produce an AAV pseudotype). In one embodiment, the ITR sequences from AAV2, or the deleted version thereof (ΔITR), are used for convenience and to accelerate regulatory approval. Alternatively, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the UTG1A1 coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

The abbreviation "sc" refers to self-complementary. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

The rAAV.hUGT1A1 vector should have a tropism for the liver (e.g., an rAAV bearing an AAV8 capsid). The vector can be formulated in a buffer/carrier suitable for infusion in human subjects. The buffer/carrier may include a component that prevents the rAAV, from sticking to the packaging or infusion tubing but does not interfere with the rAAV binding activity in vivo.

An AAV viral vector is an AAV nuclease-resistant particle having an AAV protein capsid into which are packaged nucleic acid sequences for delivery to target cells. An AAV capsid is composed of about 60 capsid protein subunits, VP1, VP2, and VP3, that are arranged in an icosahedral symmetry in a ratio of approximately 1:1:10 to 1:1:20, depending upon the selected AAV. AAV serotypes may be selected as sources for capsids of AAV viral vectors (DNase resistant viral particles) including, e.g., AAV1, AAV2, AAV3, AAV3B, AAV4, AAV5, AAV6, AAV6.2, AAV7, AAV8, AAV9, rh10, AAVrh64R1, AAVrh64R2, or rh8 (See, e.g., U.S. Publication Nos. 2007/0036760 and 2009-0197338, and EP 1310571). See also, International Publication No. WO 2003/042397 (AAV7 and other simian AAV), U.S. Pat. Nos. 7,790,449 and 7,282,199 (AAV8), International Publication No. WO 2005/033321, U.S. Pat. No. 7,906,111 (AAV9), and International Publication Nos. WO 2006/110689 and WO 2003/042397 (rh10). Other examples may include one or more variant VP capsid proteins (VP) such as those described in International Publication No. WO 2015/013313, e.g., the RHM4-1, RHM15-1, RHM15-2, RHM15-3/RHM15-5, RHM15-4 and RHM15-6 capsid variants, which are described as presenting a high liver tropism, and the documents cited therein. International Publication No. WO 2015/013313 refers to a "modified capsid" as a chimeric capsid or capsid comprising one or more variant VP capsid proteins derived from one or more wild-type AAV VP capsid proteins. In a particular embodiment, the AAV vector is a chimeric vector, i.e., its capsid comprises VP capsid proteins derived from at least two different AAV serotypes, or comprises at least one chimeric VP protein combining VP protein regions or domains derived from at least two AAV serotypes. The aforementioned documents also describe other AAV which may be selected for generating AAV, each of which are incorporated by reference. In some embodiments, an AAV cap for use in the viral vector can be generated by mutagenesis (e.g., by insertions, deletions, or substitutions) of one of the aforementioned AAV Caps or its encoding nucleic acid. In some embodiments, the AAV capsid is chimeric, comprising domains from two or three or four or more of the aforementioned AAV capsid proteins. In some embodiments, the AAV capsid is a mosaic of VP1, VP2, and VP3 monomers from two or three different AAVs or recombinant AAVs. In some embodiments, a rAAV composition comprises more than one of the aforementioned caps.

As used herein, "AAV8 capsid" refers to the AAV8 capsid having the encoded amino acid sequence of GenBank accession: YP_077180, which is incorporated by reference herein, and reproduced in SEQ ID NO: 11. Some variation from this encoded sequence is encompassed by the present invention, which may include sequences having about 99% identity to the referenced amino acid sequence in GenBank accession: YP_077180 (U.S. Pat. Nos. 7,282,199, 7,790,449, 8,319,480, 8,962,330, 8,962,332; e.g., less than about 1% variation from the referenced sequence). In another embodiment, the AAV8 capsid may have the VP1 sequence of the AAV8 variant described in International Publication No. WO 2014/124282, which is incorporated by reference herein. Methods of generating the capsid, coding sequences therefore, and methods for production of rAAV viral vectors have been described. (Gao et al., Proc. Natl. Acad. Sci. USA., 2003, 100(10), 6081-6086; U.S. Patent No. 2013/0045186; and International Publication No. WO 2014/124282).

For packaging an expression cassette into virions, the AAV inverted terminal repeat sequences (ITRs) are the only AAV components required in cis in the same construct as the gene expression cassette. Suitably, the coding sequences for the replication (rep) and/or capsid (cap) are removed from the AAV genome and supplied in trans or by a packaging cell line in order to generate the AAV vector. Thus, the vectors provided herein are replication-incompetent. A pseudotyped AAV may be provided which contains ITRs from a source which differs from the source of the AAV capsid. Additionally or alternatively, a chimeric AAV capsid may be utilized. Still other AAV components may be selected. Sources of such AAV sequences are described herein and may also be isolated or obtained from academic, commercial, or public sources (e.g., the American Type Culture Collection (ATCC®), Manassas, Va.). Alternatively, the AAV sequences may be obtained through synthetic or other suitable means by reference to published sequences such as are available in the literature or in databases such as, e.g., GenBank®, PubMed®, or the like.

Methods for generating and isolating AAV viral vectors suitable for delivery to a subject are known in the art. See, e.g., U.S. Pat. No. 7,790,449; U.S. Pat. No. 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, N.Y. (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

The rAAV.hUGT1A1 vector can be manufactured as follows. Briefly, cells (e.g. HEK 293 cells) are propagated in a suitable cell culture system and transfected for vector generation. The rAAV.hUGT1A1 vector can then be harvested, concentrated and purified to prepare bulk vector which is then filled and finished in a downstream process.

Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest.

The crude cell harvest may thereafter be subject method steps such as concentration of the vector harvest, diafiltration of the vector harvest, microfluidization of the vector harvest, nuclease digestion of the vector harvest, filtration of microfluidized intermediate, purification by chromatography, purification by ultracentrifugation, buffer exchange by tangential flow filtration, and formulation and filtration to prepare bulk vector.

In certain embodiments, methods similar to those described herein may be used in conjunction with other AAV producer cells. Numerous methods are known in the art for production of rAAV vectors, including transfection, stable cell line production, and infectious hybrid virus production systems which include Adenovirus-AAV hybrids, herpesvirus-AAV hybrids and baculovirus-AAV hybrids. See, e.g., G Ye, et al, Hu Gene Ther Clin Dev, 25: 212-217 (December 2014); R M Kotin, Hu Mol Genet, 2011, Vol. 20, Rev Issue 1, R2-R6; M. Mietzsch, et al, Hum Gene Therapy, 25: 212-222 (March 2014); T Virag et al, Hu Gene Therapy, 20: 807-817 (August 2009); N. Clement et al, Hum Gene Therapy, 20: 796-806 (August 2009); D L Thomas et al, Hum Gene Ther, 20: 861-870 (August 2009). rAAV production cultures for the production of rAAV virus particles all require; suitable host cells, including, for example, human-derived cell lines such as HeLa, A549, or 293 cells, or insect-derived cell lines such as SF-9, in the case of baculovirus production systems; 2) suitable helper virus function, provided by wild type or mutant adenovirus (such as temperature sensitive adenovirus), herpes virus, baculovirus, or a nucleic acid construct providing helper functions in trans or in cis; 3) functional AAV rep genes, functional cap genes and gene products; 4) a transgene (such as a therapeutic transgene) flanked by AAV ITR sequences; and 5) suitable media and media components to support rAAV production.

A variety of suitable cells and cell lines have been described for use in production of AAV. The cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, a HEK 293 cell (which express functional adenoviral E1), Saos, C2C12, L cells, HT1080, HepG2 and primary fibroblast, hepatocyte and myoblast cells derived from mammals including human, monkey, mouse, rat, rabbit, and hamster. In certain embodiments, the cells are suspension-adapted cells. The selection of the mammalian species providing the cells is not a limitation of this invention; nor is the type of mammalian cell, i.e., fibroblast, hepatocyte, tumor cell, etc.

In order to ensure that empty capsids are removed from the dose of AAV. hUGT1A1 that is administered to patients, empty capsids are separated from vector particles during the vector purification process, e.g., using cesium chloride gradient ultracentrifugation. In one embodiment, the vector particles containing packaged genomes are purified from empty capsids using the process described in International Patent Application No. PCT/US16/65976, filed Dec. 9, 2016 and its priority documents U.S. Patent Application No. 62/322,098, filed Apr. 13, 2016 and U.S. Patent Appln No.

62/266,341, filed on Dec. 11, 2015, and entitled "Scalable Purification Method for AAV8", which is incorporated by reference herein. See, also, purification methods described in International Patent Application No. PCT/US16/65974, filed Dec. 9, 2016, and its priority documents, U.S. Patent Application No. 62/322,083, filed Apr. 13, 2016 and 62/266,351, filed Dec. 11, 2015 (AAV1); International Patent Appln No. PCT/US16/66013, filed Dec. 9, 2016 and its priority documents U.S. Provisional Applications No. 62/322,055, filed Apr. 13, 2016 and 62/266,347, filed Dec. 11, 2015 (AAVrh10); and International Patent Application No. PCT/US16/65970, filed Dec. 9, 2016, and its priority applications U.S. Provisional Application Nos. 62/266,357 and 62/266,357 (AAV9), which are incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates.

In certain embodiments, the method separates recombinant AAV8 viral particles containing DNA comprising pharmacologically active genomic sequences from genome-deficient (empty) AAV8 capsid intermediates. The method involves (a) forming a loading suspension comprising: recombinant AAV8 viral particles and empty AAV8 capsid intermediates which have been purified to remove non-AAV materials from an AAV producer cell culture in which the particles and intermediates were generated; and a Buffer A comprising 20 mM Bis-Tris propane (BTP) and a pH of about 10.2; (b) loading the suspension of (a) onto a strong anion exchange resin, said resin being in a vessel having an inlet for flow of a suspension and/or solution and an outlet permitting flow of eluate from the vessel; (c) washing the loaded anion exchange resin with Buffer 1% B which comprises 10 mM NaCl and 20 mM BTP with a pH of about 10.2; (d) applying an increasing salt concentration gradient to the loaded and washed anion exchange resin, wherein the salt gradient ranges from 10 mM to about 190 mM NaCl, inclusive of the endpoints, or an equivalent; and (e) collecting the rAAV particles from eluate, said rAAV particles being purified away from intermediates.

In one embodiment, the pH used is from 10 to 10.4 (about 10.2) and the rAAV particles are at least about 50% to about 90% purified from AAV8 intermediates, or a pH of 10.2 and about 90% to about 99% purified from AAV8 intermediates. In one embodiment, this is determined by genome copies. A stock or preparation of rAAV8 particles (packaged genomes) is "substantially free" of AAV empty capsids (and other intermediates) when the rAAV8 particles in the stock are at least about 75% to about 100%, at least about 80%, at least about 85%, at least about 90%, at least about 95%, or at least 99% of the rAAV8 in the stock and "empty capsids" are less than about 1%, less than about 5%, less than about 10%, less than about 15% of the rAAV8 in the stock or preparation.

In one embodiment, the formulation is be characterized by an rAAV stock having a ratio of "empty" to "full" of 1 or less, preferably less than 0.75, more preferably, 0.5, preferably less than 0.3.

In a further embodiment, the average yield of rAAV particles is at least about 70%. This may be calculated by determining titer (genome copies) in the mixture loaded onto the column and the amount presence in the final elutions. Further, these may be determined based on q-PCR analysis and/or SDS-PAGE techniques such as those described herein or those which have been described in the art.

For example, to calculate empty and full particle content, VP3 band volumes for a selected sample (e.g., an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 µL loaded is then multiplied by 50 to give particles (pt)/mL. Pt/mL divided by GC/mL gives the ratio of particles to genome copies (pt/GC). Pt/mL–GC/mL gives empty pt/mL. Empty pt/mL divided by pt/mL and ×100 gives the percentage of empty particles.

Confirmation of the AAV8 serotype of the vector may be achieved by an assay based upon analysis of peptides of the VP3 capsid protein by mass spectrometry (MS). The method involves multi-enzyme digestion (trypsin, chymotrypsin and endoproteinase Glu-C) of the VP3 protein band excised from SDS-PAGE gels followed by characterization on a UPLC-MS/MS on a Q-Exactive Orbitrap mass spectrometer to sequence the capsid protein. A tandem mass spectra (MS) method allows for identification of certain contaminant proteins and deriving peptide sequence from mass spectra.

Generally, methods for assaying for empty capsids and AAV vector particles with packaged genomes have been known in the art. See, e.g., Grimm et al., *Gene Therapy* (1999) 6:1322-1330, Sommer et al., *Molec. Ther.* (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

The pharmaceutical compositions described herein are designed for delivery to subjects in need thereof by any suitable route or a combination of different routes. Direct delivery to the liver (optionally via intravenous, via the hepatic artery, or by transplant), oral, inhalation, intrathecal, intranasal, intratracheal, intraarterial, intraocular (e.g., intravitreal), intravenous, intramuscular, subcutaneous, intradermal, and other routes of administration.

The present invention also provides pharmaceutical compositions comprising a nucleic acid of the invention, or the vector of the invention, or the cell of the invention. Such compositions comprise a therapeutically effective amount of the UGT1A1. In certain embodiments, reaching expression levels as low as about 5% of wild-type expression levels can provide therapeutic benefit. In other embodiments, expression levels are higher than 5% of wild-type expression levels, e.g., more than 10%, more than 20%, more than 30%, or up to about 100% of wild-type expression levels.

The replication-defective viruses can be formulated with a physiologically acceptable carrier for use in gene transfer and gene therapy applications. In the case of AAV viral vectors, quantification of the genome copies ("GC") may be used as the measure of the dose contained in the formulation. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The nuclease resistant particles are then subjected to heat treatment to release the genome from the capsid. The released genomes are then quantitated by real-time PCR using primer/probe sets targeting specific region of the viral genome (usually poly A signal). Another suitable method for determining genome copies are the quantitative-PCR (qPCR), particularly the optimized qPCR or digital droplet PCR [Lock Martin, et al, Human Gene Therapy Methods. April 2014, 25(2): 115-125. doi:10.1089/hgtb.2013.131, published online ahead of editing Dec. 13, 2013].

The rAAV.UGT1A1 vector compositions can be formulated in dosage units to contain an amount of rAAV that is in the range of about $1.0 \times 10^9$ GC to about $1.0 \times 10^{14}$ GC (to treat an average adult subject of 70 kg in body weight), and preferably $1.0 \times 10^{12}$ GC to $1.0 \times 10^{14}$ GC for a human patient. In another embodiment, the dose is less than about $1 \times 10^{13}$ GC/kg. For example, the dose of AAV virus may be about $1 \times 10^9$ GC, about $5 \times 10^9$ GC, about $1 \times 10^{10}$ GC, about $5 \times 10^{10}$ GC, or about $2.5 \times 10^{12}$ GC. In another example, the variants may be delivered in an amount of about 0.001 mg to about 10 mg/kg.

The above-described recombinant vectors may be delivered to host cells according to published methods. The rAAV, preferably suspended in a physiologically acceptable carrier, may be administered to a human or non-human mammalian subject. The term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of suspensions, emulsions, sustained-release formulations and the like. Examples of suitable pharmaceutical carriers are described in "Remington's Pharmaceutical Sciences" by E. W. Martin. In one embodiment, the vector is formulated in a composition comprising phosphate-buffered saline. In another particular embodiment, the vector is formulated in a composition comprising ringer lactate and a non-ionic surfactant, such as Pluronic® F68 at a final concentration of 0.01-0.0001%, such as at a concentration of 0.001%, by weight of the total composition. Typically, compositions for intravenous administration are solutions in sterile isotonic aqueous buffer. Where necessary, the composition may also include a solubilizing agent and a local anesthetic such as lignocaine to, ease pain at the, site of the injection. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

A course of treatment may optionally involve repeat administration of the same viral vector (e.g., an AAV8 vector) or a different viral vector (e.g., an AAV8, an AAV3B, an AAVhu.37, and an AAVrh10). Still other combinations may be selected using the viral vectors described herein.

For example, treatment with an rAAV.UGT1A1 and compositions containing same may involve co-therapy with an immunosuppressive regimen. The immunosuppressive agent may be administered prior to the first vector administration, substantially simultaneously therewith, or may be administered after first vector administration. Optionally, the immunosuppressive regimen may be contained for 1 day-14 days, or shorter periods therebetween, e.g., 3 days, 7 days, 10 days, or for longer periods as needed or desired. Suitable immunosuppressive agents may be readily selected by one of skill in the art and may include, e.g., include, but are not limited to, steroids, antimetabolites, T-cell inhibitors, and alkylating agents. In certain embodiments, patients are monitored for elevated liver enzymes, and are optionally treated with transient immunosuppressant therapy (e.g., if at least about 2× baseline levels of aspartate transaminase (AST) or alanine transaminase (ALT) are observed).

Optionally, the composition described herein may be combined in a regimen involving other therapies, including, e.g., phototherapy.

Current phototherapy may involve exposure to therapeutic lamps (emission range: 400-525 nm, peak emission: 450-460 nm). Absent treatment as provided herein, patients undergo to phototherapy sessions for at least about 10 hours to about 12 hours/day, or longer. Patient's survival is dependent on the indefinite continuation of this therapy. Although initially very effective, phototherapy is inconvenient and the efficacy of this treatment is reduced with ageing due to increased thickness of skin and body surface/weight ratio; thus, patients are again at risk for kernicterus around time of puberty. To improve effectiveness of phototherapy it recommended to change lamps after about 1,000-1,500 hours of use (approximately every four to six months), keep the light source close to the body (about 15-20 centimeters, 6-8 inches), maximize skin exposure to light, use solid white sheets, and place reflective surfaces (mirrors and emergency blankets) around the bed.

In certain embodiments, a patient having Crigler-Najjar syndrome type I is treated with a combination of gene therapy and phototherapy. For example, phototherapy treatment may be initiated prior to treatment with gene therapy. Phototherapy may additionally or alternatively be administered for up to 24 hours to about 4 weeks, or points in-between (e.g., about 10 days, about 2 weeks, about three weeks) post-dosing with an AAV.UGT1A1 composition. Suitably, following about 4 weeks or less, post dosing with an AAV.UG1TA1 composition, the length of time required for phototherapy in a patient per day is reduced by at least about 30% to about 100%, or at least about 50%, at least about 75%, at least about 80%. In some embodiments, the patient may only require phototherapy on non-consecutive days. In another embodiment, phototherapy is no longer required in order to reduce bilirubin levels to acceptable levels.

In certain other embodiments, the patients are thereafter treated according to the conventional standard of care for Crigler-Najjar syndrome type II patients. In such patients, phenobarbital is used to control bilirubin levels and any CNS-related symptoms.

In certain embodiments, Crigler-Najjar syndrome type II patients may be treated with an AAV.hUGT1A1 composition as described herein. Phenobarbital or other therapy may additionally or alternatively be administered for 24 hours to about 4 weeks, or points in-between (e.g., about 10 days, about 2 weeks, about three weeks) post-dosing with an AAV.UGT1A1 composition. Suitably, following about 4 weeks or less, post dosing with an AAV.UGT1A1 composition, the dose of phenobarbital required in a patient per day is reduced by at least about 30% to about 100%, or at least about 50%, at least about 75%, at least about 80%. In another embodiment, phenobarbital is no longer required.

In certain embodiments, patients with defective UGT1A1 expression levels, Crigler-Najjar syndrome type I or II, who have been treated with AAAV.hUGT1A1 compositions as described herein, have elevated bilirubin levels such as found in patients having Gilbert's syndrome, but no further ongoing treatment is required.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

The term "regulation" or variations thereof as used herein refers to the ability of a composition to inhibit one or more components of a biological pathway.

A "subject" is a mammal, e.g., a human, mouse, rat, guinea pig, dog, cat, horse, cow, pig, or non-human primate, such as a monkey, chimpanzee, baboon or gorilla.

As used herein, "disease", "disorder" and "condition" are used interchangeably, to indicate an abnormal state in a subject.

The following examples are illustrative only and are not a limitation on the scope of the invention. A listing of abbreviations used herein is provided in Table 1, below

TABLE 1

| List of abbreviations | |
|---|---|
| AAV | Adeno-associated virus |
| ACVP | American College of Veterinary Pathologists |
| ALP | Alkaline Phosphatase |
| ALT | Alanine Aminotransferase |
| AMC | Animal Models Core |
| ANOVA | Analysis of variance |
| APTT | Activated partial prothrombin time |
| AST | Aspartate Aminotransferase |
| BRB | Biomedical Research Building |
| CBC | Complete blood count |
| cDNA | complementary Deoxyribonucleic Acid |
| CFR | Code of Federal Regulation |
| CN | Crigler-Najjar |
| CPK | Creatine phosphokinase |
| CTL | Cytotoxic T lymphocyte |
| ddPCR | Droplet digital polymerase chain reaction |
| DPBS | Dulbecco's phosphate buffered saline |
| ELISA | Enzyme-linked immunosorbent assay |
| ELISPOT | Enzyme-linked immunospot |
| FDA | Food and Drug Administration |
| FDP | Fibrin degradation products |
| GC | Genome copy |

TABLE 1-continued

List of abbreviations

| | |
|---|---|
| GGT | Gamma glutamyl transferase |
| GLP | Good Laboratory Practices |
| GMP | Good Manufacturing Practices |
| GTP | Gene Therapy Program |
| H&E | Hematoxylin and eosin stain |
| hUGT1A1 | Human UDP glucuronosyltransferase 1 family, polypeptide A1 |
| IACUC | Institutional Animal Care and Use Committee |
| ID | Identification |
| IFN-γ | Interferon-γ |
| IM | Intramuscular |
| IV | Intravenous |
| kg | Kilogram |
| LFT | Liver function test |
| MED | Minimal effective dose |
| mg | Milligram |
| ml | Milliliter |
| NAb | Neutralizing antibody |
| NBF | Neutral buffered formalin |
| NHP | Nonhuman primate |
| NPRP | Nonhuman Primate Research Program |
| OCT | Optimum cutting temperature |
| OCTGT | Office of Cellular, Tissue and Gene Therapies |
| PBMC | Peripheral blood mononuclear cell |
| PT | Prothrombin time |
| QA | Quality Assurance |
| qPCR | Quantitative PCR |
| RT-qPCR | Real time quantitative polymerase chain reaction |
| SD | Standard deviation |
| SEM | Standard error of the mean |
| SOP | Standard operating procedure |
| SFU | Spot forming unit |
| TBG | Thyroxine binding globulin |
| TRL | Translational Research Laboratories |
| UDP | Uridine phosphorylase |
| UGT1A1 | UDP glucuronosyltransferase 1 family, polypeptide A1 |
| ULAR | University Laboratory Animal Resources |

EXAMPLE 1

Vector Generation and Comparison

A series of vectors were constructed having five hUGT1A1 open reading frames (ORFs). See Table 2, below. In brief, there was no statistically significant difference in yield of the AAV8 vector lots for each of the five hUGT1A1 ORFs (Table 1).

When the HEK293 cells growing, the cells are transfected with each of three plasmids: the AAV serotype-specific packaging (trans) plasmid, the ad-helper plasmid, and vector cis plasmid containing the expression cassette for the UGT1A1 transgene flanked by AAV inverted terminal repeats (ITRs). Transfection is carried out using the calcium phosphate method. The full-length sequence of the cis plasmid carrying TBG.hUGT1A1co.WPRE.BGH is provided in SEQ ID NO: 9 (vector genome spanning from 5' to 3' ITR, nt 1-3558 of SEQ ID NO: 9). The full-length sequence of the cis plasmid carrying TBG.hUGT1A1co.BGH is provided in SEQ ID NO: 10 (vector genome spanning from 5' to 3'ITR, nt 1-3152 of SEQ ID NO: 10). To construct the other plasmids, the coding sequences of SEQ ID NO:12 (UGT1A1 U201DP), SEQ ID NO: 13 (UGT1A1 U001), SEQ ID NO: 14 (UGT1A1 U011TY), or SEQ ID NO: 18 (U3G), is substituted for nt 1092-2690 of SEQ ID NO: 10. In other embodiments, a plasmid in which the ampicillin resistance gene is replaced by a kanamycin resistance gene is used. The trans plasmid used carries an AAV8 gene encoding the AAV8 capsid VP1 protein having the sequence of SEQ ID NO: 11. These vectors were evaluated in male and female wild type C57BL/6 mice following IV injection of $3 \times 10^{12}$ GC/kg of vector via the tail vein. Blood was taken by cardiac puncture at necropsy for evaluation of AST, ALT, alkaline phosphatase, and total bilirubin. Liver was harvested, with one lobe taken for fixation and paraffin embedding and the rest snap frozen and stored at −80° C. Expression was evaluated by hUGT1A1 protein levels determined by Western blot of liver homogenates with human UGT1A1-specific antibodies used for detection. Western blot images were quantified against the same amount of protein from a positive control sample.

TABLE 2

Yield of hUGT1A1 expressing vectors.

| Vector Name | Total Yield (GC) |
|---|---|
| AAV8.TBG.hUGT1A1co.WPRE.BGH | $5.90 \times 10^{13}$ |
| AAV8.TBG.U001.BGH | $1.29 \times 10^{14}$ |
| AAV8.TBG.U011TY.BGH | $1.09 \times 10^{14}$ |
| AAV8.TBG.U201DP.BGH | $5.95 \times 10^{13}$ |
| AAV8.TBG.U3G.BGH | $1.31 \times 10^{14}$ |

Liver samples were frozen on dry ice and stored at ≤−60° C. Tissue homogenates were made and Western blots to determine hUGT1A1 expression were performed as follows. Mouse liver samples were homogenized in RIPA Lysis and Extraction Buffer (ThermoFisher Scientific, Waltham, Mass., USA) and protease inhibitor using the QIAGEN TissueLyser II (QIAGEN, Hilden, Germany), in accordance with manufacturer's instructions. Protein levels were quantified by Pierce BCA Protein Assay Kit (ThermoFisher Scientific, Waltham, Mass., USA), in accordance with manufacture's instructions. Homogenates were diluted to enable 1 μg of protein to be run on the gel. Samples were heated at 95° C. for 5 minutes, separated on a NuPAGE Novex 10% Bis-Tris Protein Gels (ThermoFisher Scientific, Waltham, Mass., USA), and transferred to Trans-Blot Turbo PDVF membrane (BioRad, Hercules, Calif., USA). Membranes were blocked for one hour at room temperature in 5% non-fat milk, tris-buffered saline, 0.1% Tween 20 (TBS-T). Membranes were washed in 0.5% non-fat milk and TBS-T and then incubated with anti-UGT1A antibody (H-300 [sc-25847], Santa Cruz Biotechnology, Dallas, Tex., USA) overnight at 4° C. at an antibody dilution of 1:200 in 0.5% non-fat milk and TBS-T. Membranes were washed three times for five minutes each with TBS-T and then incubated with goat anti-rabbit HRP-conjugated antibody (sc-2054, Santa Cruz Biotechnology, Dallas, Tex., USA) for one hour at room temperature at an antibody dilution of 1:5000 in 0.5% non-fat milk and TBS-T. Membranes were washed three times for five minutes each with TBS-T and HRP was detected using Pierce ECL Western Blotting Substrate (ThermoFisher Scientific, Waltham, Mass., USA), in accordance with manufacturer's instructions. Images of bands were quantified against the same amount of protein from a positive control sample.

When assessed for protein expression, for two of the vectors (AAV8.TBG.U011TY.BGH and AAV8.TBG.U3G.BGH), the use of different codon optimized sequences significantly reduced expression compared to the AAV8.TBG.hUGT1A1co.WPRE.BGH vector. Expression of hUGT1A1 in female mice was reduced compared to that see in male mice. There were no significant differences in AST, ALT, alkaline phosphatase, and total bilirubin levels across the groups within a sex. Comparison of clinical chemistry values and hUGT1A1 expression by Western blot was performed using a one way analysis of variance with Tukey's multiple comparisons post-test within a sex.

Expression of hUGT1A1 was not significantly different between the AAV8.TBG.hUGT1A1co.WPRE.BGH vector and two of the second generation vectors (AAV8.TBG.U001.BGH, and AAV8.TBG.U201DP.BGH) in male mice (FIG. 1). Both of these second generation vectors lack the woodchuck post-regulatory element (WPRE) which has been previously described as enhancing transgene expression. However, there have been regulatory concerns raised regarding the safety of delivering WPRE to patients with a pre-existing liver disease. Since CN1 is a liver disease, vectors lacking this element are selected to proceed with further study.

EXAMPLE 2

In Vivo Evaluation of the Efficacy of AAV8.TBG.hUGT1A1co.WPRE.bGH Following Systemic Administration in Newborn Pups A. Summary The purpose of this proof-of-concept (POC) study was to evaluate the initial vector designed for the treatment of CN, AAV8.TBG.hUGT1A1co.WPRE.BGH. This vector was administered to newborn UGT1 knockout (KO) mice to evaluate human UGT1A1 (hUGT1A1) expression and the ability of a gene therapy approach to increase survival of the UGT1 KO mouse model (an animal model of CN).

Three litters of mice (UGT1 KO: n=5; heterozygous: n=9; wild type [WT]: n=4) born following mating of heterozygous×heterozygous mice were injected intravenously (IV) with AAV8.TBG.hUGT1A1co.WPRE.BGH ($10^{11}$ genome copies [GC] per mouse) via the superficial temporal facial vein within 24 hours of birth. All mice were genotyped at weaning at day 21 post-birth. Blood samples were collected biweekly from day 28 post-birth throughout the in-life phase of the study for evaluation of serum total bilirubin levels. Mice were necropsied on day 270 post-test article administration. Liver was harvested at necropsy, fixed in 10% neutral buffered formalin, and processed for immunohistochemical staining for UGT1A1.

Neonatal gene therapy with AAV8.TBG.hUGT1A1co.WPRE.BGH protected UGT1 KO mice from lethal hyperbilirubinemia in the immediate postnatal period and significantly increased survival from 5 days in untreated UGT1 KO mice to 270 days post-test article administration (end of the study, p<0.0001 compared with untreated UGT1 KO mice). See FIG. 2. Rescued UGT1 KO mice appeared phenotypically identical to their heterozygous and WT littermates, albeit with elevated serum total bilirubin levels. Serum total bilirubin levels in the AAV-treated UGT1 KO mice were elevated by 5.7-fold compared with heterozygous and WT animals, but were reduced 15.2-fold when compared with UGT1 KO mice rescued to adulthood by phototherapy (p<0.0001 comparison by Student's t test). Dilution of the vector GCs in the liver due to proliferation of hepatocytes resulted in loss of some transgene expression and incomplete long term correction based on serum total bilirubin levels, which were elevated compared to heterozygous and WT littermates.

B. Methods

Mice were generated following heterozygous×heterozygous mating. All pups from three litters were administered with the test article within 24 hours of birth. Mice were ear tagged and genotyped at weaning, which occurred at 21 days post-birth.

The intravenous (IV) route via the superficial temporal facial vein was selected for use because it is the most efficient route used to target the liver, which in humans is the clinical site of the disease.

Efficacy of the test article was determined by total bilirubin levels in serum. In addition, immunohistochemical (IHC) analysis was performed to determine the levels of hUGT1A1 protein expression in the liver.

Changes in the serum total bilirubin levels of the animals were analyzed. Mice were anesthetized and blood collected by retro-orbital or submandibular technique during the in-life phase of the study or by cardiac puncture at necropsy. Blood was collected in labeled serum gel separator brown top tubes, allowed to clot, and then serum was isolated.

Comparison of survival curves was performed using a log-rank (Mantel-Cox) test. For serum total bilirubin data, cohort average and standard error of the mean (SEM) was calculated and reported. Student's t test was performed on the serum total bilirubin level data to determine any test article-related effects compared to mice rescued to adulthood by phototherapy.

C. Results

No mice died during the course of the study. Neonatal gene therapy with $10^{11}$ genome copies (GC)/mouse AAV8.TBG.hUGT1A1co.WPRE.BGH protected UGT1 KO mice from lethal hyperbilirubinemia in the immediate postnatal period, with a significant increase in survival from 5 days in untreated UGT1 KO mice to 270 days in vector-treated mice (FIG. 2, p<0.0001 comparison of survival curves by log-rank (Mantel-Cox) test).

Mice were weighed from day 28 post-birth throughout the initial in-life phase of the study. All animals continued to gain weight over the course of the study. Rescued UGT1 KO mice appear phenotypically identical to their WT and heterozygous littermates and with no difference in body weight.

Serum total bilirubin levels were analyzed from day 28 post-birth throughout the in-life phase of the study. Serum total bilirubin levels in the AAV-treated UGT1 KO mice were elevated by 5.7-fold compared with heterozygous and WT animals, but were significantly reduced 15.2-fold compared with UGT1 KO mice rescued to adulthood by phototherapy (p<0.0001 comparison by Student's t test). Dilution of the vector GCs in the liver due to proliferation of hepatocytes results in loss of some transgene expression and incomplete long term correction based on total bilirubin levels, which are elevated compared to heterozygous and WT littermates. Therefore, neonatal gene therapy protected UGT1 KO mice from lethal hyperbilirubinemia in the immediate postnatal period and significantly increased survival. Rescued UGT1 KO mice appear phenotypically identical to their heterozygous and WT littermates, albeit with elevated total bilirubin levels.

UGT1 KO mice administered with test article as neonates were necropsied on day 270 post-vector administration and liver collected, fixed in 10% NBF, and processed for IHC staining for UGT1A1. Staining indicates hepatocytes expressing UGT1A1, which was sustained throughout the life of the mouse.

D. Conclusions

Neonatal gene therapy with AAV8.TBG.hUGT1A1co.WPRE.BGH protected UGT1 KO mice from lethal hyperbilirubinemia in the immediate postnatal period and significantly increased survival from 5 days in untreated UGT1 KO mice to 270 days post-test article administration (p<0.0001 compared with untreated UGT1 KO mice). Rescued UGT1 KO mice appeared phenotypically identical to their heterozygous and WT littermates, albeit with elevated total bilirubin levels. Serum total bilirubin levels in the AAV-treated UGT1 KO mice were elevated by 5.7-fold compared with heterozygous and WT animals, but were reduced 15.2-fold when compared with UGT1 KO mice rescued to adulthood by phototherapy (p<0.0001 comparison by Student's t test). Dilution of the vector GCs in the liver due to proliferation of hepatocytes resulted in loss of some transgene expression and incomplete long term correction based on serum total bilirubin levels, which were elevated compared to heterozygous and WT littermates.

EXAMPLE 3

Phototherapy Study

A. Summary

The purpose of this proof-of-concept (POC) study was to evaluate the efficacy of phototherapy in UGT1 knockout (KO) mice, in an attempt to model the current treatment strategy for CN. Phototherapy has been previously reported to allow survival of UGT1 KO mice to adulthood by protecting affected mice from lethal hyperbilirubinemia in the immediate postnatal period.

Litters of mice born following heterozygous×heterozygous mating were exposed to blue florescent light ($\lambda$=450 nm; 10-30 µW/cm$^2$/nm) for 12 hours per day for up to 21 days post-birth. At the time of weaning (day 21 post-birth), all offspring were genotyped.

While this study is currently ongoing as of this writing, 63 UGT1 KO mice have been weaned following phototherapy. These animals did not require to be maintained on phototherapy post-weaning and the majority of the mice demonstrate normal duration of survival. The UGT1 KO mice rescued by phototherapy had significantly elevated total bilirubin levels compared with the UGT1 KO mice that received AAV gene therapy (p<0.0001 comparison by Student's t test).

In the UGT1 KO mouse model, phototherapy in the immediate postnatal period protects the animals from kernicterus; after 3-4 weeks phototherapy can be withdrawn and the animals survive but with persistent hyperbilirubinemia. Pretreatment with phototherapy allows gene therapy vector administration to be delayed until the liver stops proliferating, which would simulate the likely clinical scenario.

B. Materials and Methods

Mice were generated following heterozgous×heterozgous mating. All pups born were exposed to the test article from birth. At weaning (day 21 after birth), mice were eartagged, genotyped, and removed from exposure to the test article.

| Genotype | Dose (µW/cm$^2$/nm) | Necropsy Time Point | Number of Males | Number of Females |
|---|---|---|---|---|
| UGT1 KO | 10-30 | N/A | 39 | 24 |

All pups born following mating of heterozygous×heterozygous mice were exposed to blue fluorescent light ($\lambda$=450 nm; 10-30 µW/cm$^2$/nm) for 12 hours per day for up to 21 days after birth.

Efficacy of the test article was determined by survival. UGT1 KO mice die without treatment within 5 days of birth due to lethal hyperbilirubinemia in the immediate postnatal period.

Changes in the serum total bilirubin levels of the animals were analyzed by the contract facility Antech Diagnostics, Inc. Mice were anesthetized and blood collected by submandibular technique during the in-life phase of the study or by cardiac puncture at necropsy. Blood was collected in labeled serum gel separator brown top tubes, allowed to clot, and then serum was isolated.

Student's t test was performed on the serum total bilirubin level data to determine any test article-related effects compared to mice rescued to adulthood by phototherapy.

C. Results

Figure 3:
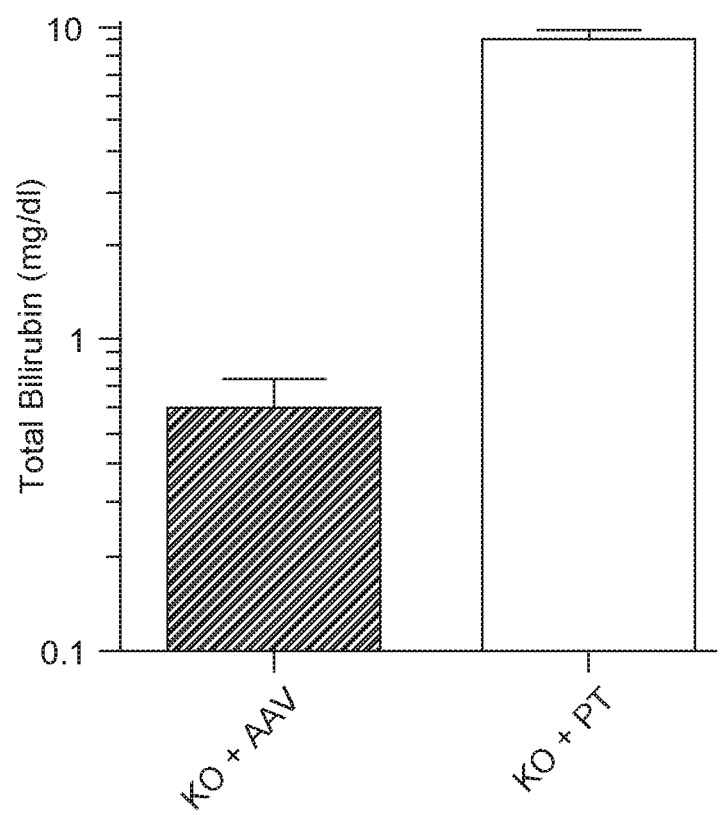
FIG. 3 shows serum total bilirubin levels in UGT1 KO following IV injection of AAV within 24 hours of birth and UGT1 KO mice following phototherapy. Total bilirubin levels in serum were measured at day 28 after birth. UGT1 KO mice were rescued to adulthood by either AAV treatment or phototherapy. AAV-treated UGT1 KO mice were injected IV with $10^{11}$ GC/mouse of AAV8.TBG.hUGT1A1co.WPRE.BGH within 24 hours of birth (n=5). Phototherapy rescued UGT1 KO mice were exposed to phototherapy immediately after birth (blue florescent light, λ=450 nm; 10-30 µW/cm²/nm) for 12 hours per day for up to 21 days after birth (n=52). All mice were genotyped at weaning FIGS. 4A-4B provide eGFP expression in C57BL/6J mice, Wistar rats, and NHP following IV injection of $10^{13}$ GC/kg of AAV8.TBG.eGFP.BGH.

See, FIG. 3. In the UGT1 KO mouse model, phototherapy in the immediate postnatal period protects the animals from kernicterus; after 3 to 4 weeks, phototherapy can be withdrawn and the animals survive but with persistent hyperbilirubinemia. Pretreatment with phototherapy before gene therapy allows vector administration to be delayed until the liver stops proliferating, which would simulate the likely clinical scenario.

EXAMPLE 4

Efficacy of hUGT1A1 Following Systemic Administration of the Vector in the UGT1 KO Mouse Model For the efficacy study, newborn pups are exposed to blue florescent light for 12 hours per day for up to 14 days post-birth. At the time of weaning, all offspring are genotyped and only UGT1−/− (knockout) animals are enrolled in the study.

Male and female UGT1 KO mice (6-12 weeks old) are administered the recombinant vector by IV injection at one of four doses increasing in full log units from $5 \times 10^{10}$ GC/kg to $5 \times 10^{13}$ GC/kg (equivalent to $10^9$ to $10^{12}$ GC/mouse). Mice are necropsied on day 28 and day 90 post-vector administration with seven male and seven female mice per cohort. Cohorts of mice receiving vehicle only (phosphate-buffered saline [PBS]) are included as a vehicle control. Therefore, a total of 140 mice are used for this study.

After vector administration, the animals are monitored daily for general observations. Regular phlebotomies are performed post-vector administration and the collected serum is evaluated for total, direct, and indirect bilirubin levels. In addition, serum albumin, ALT, and AST levels is also evaluated. At the time of sacrifice, blood is collected for complete blood counts (CBC) and clinical chemistries, in addition to total, direct, and indirect bilirubin levels. A full necropsy is performed on seven animals (if no unexpected deaths) per group per time point with a thorough and systematic examination and dissection of the animal viscera and carcass. Tissues are collected at necropsy for vector biodistribution and transcript expression levels by qPCR and RT-qPCR, respectively. DNA and RNA is extracted from mice that received the highest vector dose and mice that received the vehicle control.

EXAMPLE 5

Non-Clinical Pharmacology/Toxicology Study

The naturally occurring model of CN1, the Gunn rat, is on a Wistar background. Previous studies using AAV gene therapy in the Gunn rat would suggest that AAV8 transduces the liver less efficiently in this model, with AAV1 producing higher transduction levels (Seppen et al., Mol Ther, 13, 1085-92 (2006)). Prior to evaluation of our gene therapy product in the rat disease model, an AAV vector transduction comparison study in the wild type Wistar rat was performed. This study was also performed in wild type C57BL/6 mice as these are the background strain for the UGT1 KO mice.

In brief, for this pharmacology/toxicology study, male and female C57BL/6J mice (6-8 weeks old, weighing 20-28 g) are administered the following vector: AAV8.TGB.U201DPmod.BGH (an AAV8 capsid having packaged therein vector genome of SEQ ID NO: 15, generated using triple transfection techniques in 293 cells. This clinical candidate vector is administered by IV injection at one of three doses increasing in full or half log units from $5 \times 10^{11}$ GC/kg to $5 \times 10^{13}$ GC/kg (equivalent to $10^{10}$ to $10^{12}$ GC/mouse). Cohorts of mice receiving vehicle only (phosphate-buffered saline [PBS]) are included as a vehicle control. Mice are necropsied on days 3, 14, 90, and 180 with seven male and seven female mice per cohort. Therefore, a total of 224 mice are used for this study.

After vector administration, the animals are monitored daily for general observations. At the time of sacrifice, blood is collected for CBC and clinical chemistries. Evaluation of the presence of inflammatory cytokines by multiplex ELISA assay (Luminex) is performed on samples from mice necropsied at day 3 and compared to baseline levels. Splenocytes are isolated from mice necropsied on day 14 post-vector administration to evaluate cytotoxic T lymphocyte (CTL) responses. IFN-γ ELISPOT is performed to evaluate the presence of AAV8 capsid- and hUGT1A1-specific T cells. AAV8 neutralizing antibody (NAb) titers is determined at day 28 post-vector administration.

A full necropsy is performed on seven animals (if no unexpected deaths) per group per time point with a thorough and systematic examination and dissection of the animal viscera and carcass. Tissues are collected at necropsy for gross pathology and histopathology examinations, vector biodistribution, and transcript expression levels. DNA and RNA are extracted from mice that received the highest vector dose and mice that received the vehicle control.

A. Summary

Male and female Wistar rats and male and female C57BL/6 mice (all 6-8 weeks old) were administered with two doses of AAV1, AAV5, and AAV8 vectors expressing enhanced green fluorescent protein (eGFP) by IV injection via the tail vein ($10^{12}$ GC/kg and $10^{13}$ GC/kg). The transduction efficiency of vectors was compared by evaluation of eGFP expression in the liver on day 7 post-vector administration. Based on initial results the study was expanded to include two further groups of male and female Wistar rats. These groups received either the AAV8.TBG.eGFP vector at a higher dose of $10^{14}$ GC/kg and were necropsied on day 7 post-vector administered or received a dose of $10^{13}$ GC/kg and were necropsied on day 14 post-vector administration.

In the Wistar rats, no differences in transduction efficiency were seen across the AAV capsids following IV administration of the same dose of vector. In male C57BL/6J mice (Jackson Laboratories), AAV8 transduction efficiency in the liver was seen in 97% of hepatocytes with extremely high transgene expression at a dose of $10^{13}$ GC/kg. In contrast, at the same vector dose, transduction efficiency in the Wistar rats with AAV8 was substantially reduced. Also, the efficiency of gene transfer into the rat liver by AAV8 was substantially lower compared with that in mice. Specifically, male mice had an average of 30.6 GC of the vector per diploid genome and male Wistar rats had an average of 1.7 GC of the vector per diploid genome detected in the liver.

Therefore, due to decreased transduction and gene transfer efficiencies in the rat relative to mice, further studies in this species would lead to a gross underestimation of the minimally effective dose for CN gene therapy applications. However, as rats were still receptive to some small level of AAV8 gene therapy the CN rat disease model, the Gunn rat, can still be used to provide additional evidence that the clinical candidate is functional. Furthermore, the Gunn rat would be useful to establish the relationship between transduction and efficacy.

B. Materials and Methods

Test Articles: AAV1.TBG.eGFP.BGH

AAV5.TBG.eGFP.BGH

AAV8.TBG.eGFP.BGH

Control Article: Phosphate buffered saline (PBS)

Efficacy of the test article was determined by enhanced green fluorescent protein (eGFP) expression in the liver. eGFP expression can be both visualized and images quantified as percent area expressing eGFP. Tissues were processed as described previously to visualize eGFP expression (Wang et al., Mol Ther, 18, 126-34 (2010), Wang et al., Hum Gene Ther, 22, 1389-401 (2011). Images were taken and eGFP expression in liver was quantified as the percentage of area expressing eGFP as described previously (Wang et al., 2010, Wang et al., 2011). Tissues samples were snap frozen at the time of necropsy and DNA was extracted using the QIAamp DNA Mini Kit (Qiagen, Valencia, Calif., USA). Detection and quantification of vector GC in extracted DNA were performed by real-time PCR as described previously (Bell et al., Mol Ther, 14, 34-44 (2006). Briefly, genomic DNA was isolated and vector GCs were quantified using primers/probe designed against the BGH polyA sequence of the vector.

C. Results eGFP Expression in Liver: In the Wistar rats, no differences in transduction efficiency were seen across the AAV capsids following IV administration of the same dose in animals necropsied on day 7 post-vector administration. Vector transduction levels across the three capsids evaluated were very low with only a few eGFP hepatocytes seen per field. Increasing the dose of the AAV8 vector to $10^{14}$ genome copies (GC)/kg or increasing the duration of the study to day 14 post-vector administration did increase transduction but overall the levels remained low. In C57BL/6J mice the transduction efficiency was substantially increased compared to that seen in the Wistar rats across the three vector capsids evaluated.

Figure 4A:
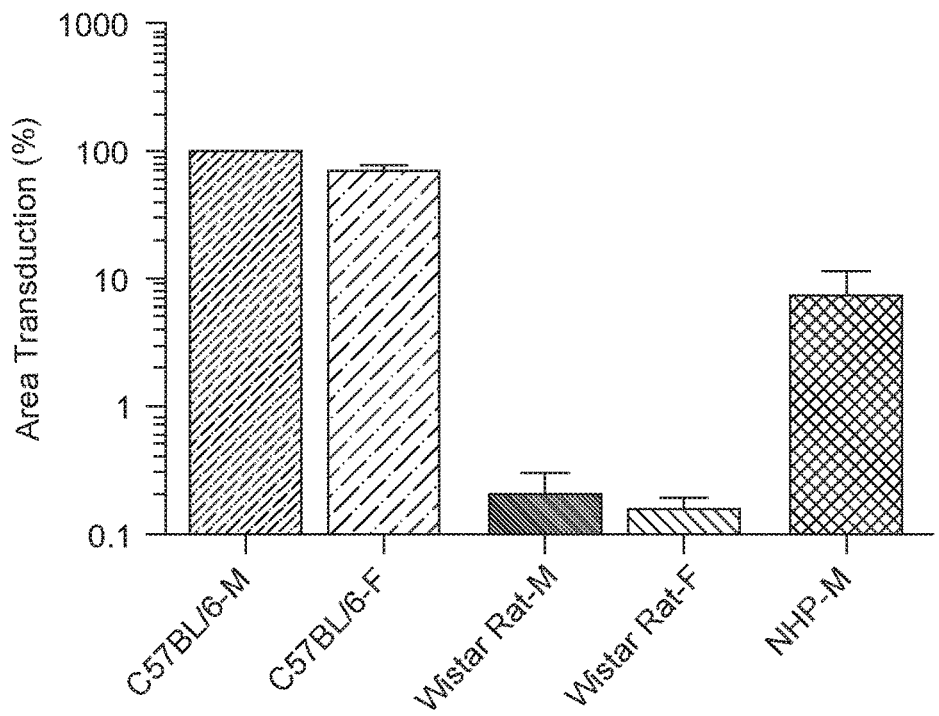
FIG. 4A. eGFP expression in the liver was quantified as percentage area transduction.
Figure 4B:
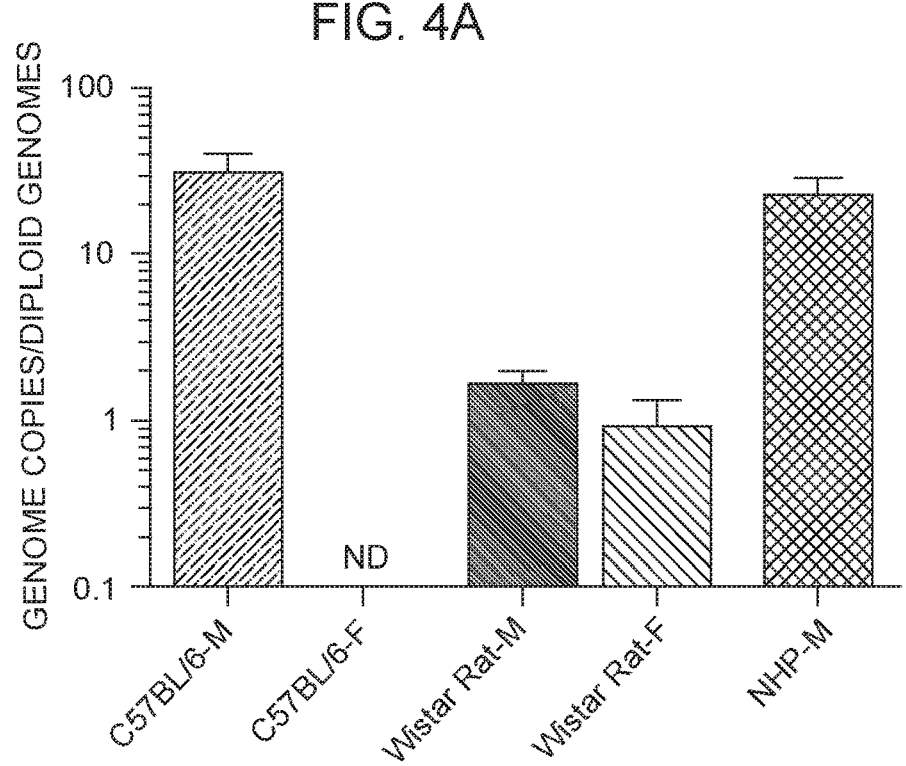
FIG. 4B. DNA was extracted for quantification of GC. Values plotted as mean±SEM. ND, not determined.

Quantification of eGFP Expression and Gene Transfer: The percentage area transduction and the vector genome copies in the liver for animals administered with AAV8 were determined (FIG. 4A-4B). In male C57BL/6J mice, AAV8 transduction efficiency in the liver was seen in 97% of hepatocytes with extremely high transgene expression at a dose of $10^{13}$ GC/kg (FIG. 4A). At the same vector dose, transduction efficiency in the Wistar rats with AAV8 was significantly reduced (FIG. 4B). For comparison, FIG. 4A also includes an image from our previously published work in rhesus macaques at 7 days post-vector administration, which showed vastly elevated transduction efficiency compared to rats (Wang et al, 2010, cited above) and determine the reason for the low transduction efficiency in rats, DNA was extracted from the harvested livers and vector GC quantified by qPCR. Interestingly gene transfer into the rat liver by AAV8 was also significantly reduced compared to mice, where male mice have an average of 30.6 GC per diploid genome and male Wistar rats have an average of only 1.7 GC per diploid genome being detected in the liver (FIG. 4B). From our previously published work in NHPs at day 7 there was an average of 23.2 GC per diploid genome present in the liver.

4. Conclusions

Due to decreased transduction and gene transfer efficiencies in the rat, it is likely that further studies in this species would lead to a gross underestimation of the minimally effective dose for CN gene therapy applications. However, as rats were still receptive to some small level of AAV8 gene therapy the CN rat disease model, the Gunn rat, can still be used to provide additional evidence that the clinical candidate is functional. Furthermore, the Gunn rat would be useful to establish the relationship between transduction and efficacy.

For comparison, our previously published work in rhesus macaques at 7 days post-vector administration showed vastly elevated transduction efficiency compared to rats, with 23.2 GC per diploid genome present in the liver.

EXAMPLE 6

Evaluation of Vector Administration in the Gunn Rat

A. Summary

The purpose of this proof-of-concept (POC) study was to evaluate the initial vector designed for the treatment of Crigler-Najjar syndrome (CN), AAV8.TBG.hUGT1A1co.WPRE.BGH. This vector was administered to Gunn rats to evaluate human UGT1A1 (hUGT1A1) expression and the ability of a gene therapy approach to decrease total bilirubin levels. The Gunn rat is a naturally occurring animal model of CN.

Male and female Gunn rats were injected intravenously (IV) with $3 \times 10^{12}$ or $3 \times 10^{13}$ genome copies (GC)/kg of AAV8.TBG.hUGT1A1co.WPRE.BGH or vehicle control (phosphate buffered saline [PBS]) at 4 weeks of age. Rats were bled routinely for evaluation of total bilirubin levels. All parameters were compared to vehicle control injected Gunn rats.

Systemic administration of $3 \times 10^{13}$ GC/kg of AAV8.TBG.hUGT1A1co.WPRE.BGH to Gunn rats reduced hyperbilirubinemia (5.4 mg/dl) to normal levels (0.1-0.3 mg/dl). Thus, the systemic administration of the first generation gene therapy vector for CN attenuated the hyperbilirubinemia characteristic to Gunn rats.

B. Materials and Methods

The purpose of this proof-of-concept (POC) study was to evaluate the first-generation vector designed for the treatment of Crigler-Najjar (CN), AAV8.TBG.hUGT1A1co.WPRE.BGH, with regards to hUGT1A1 expression and total bilirubin levels in Gunn rats. Phosphate buffered saline (PBS) was used as a control. The intravenous (IV) route via the tail vein was selected for use because it is the most efficient route used to target the liver, which in humans is the clinical site of the disease. Efficacy of the test article was determined by total bilirubin levels in serum. In addition, immunohistochemical (IHC) analysis was performed to determine the levels of hUGT1A1 protein expression in the liver. Changes in the serum total bilirubin levels of the animals were analyzed. Rats were anesthetized and blood collected by retro-orbital technique during the in-life phase of the study or by cardiac puncture at necropsy. Blood was collected in labeled serum gel separator brown top tubes, allowed to clot, and then serum was isolated. At the time of necropsy tissues were collected for transgene expression. Liver samples were fixed in 10% neutral buffered formalin (NBF) and processed for determination of transgene expression by IHC.

C. Results—Effect of Test Article on Serum Total Bilirubin Levels

Figure 5A:
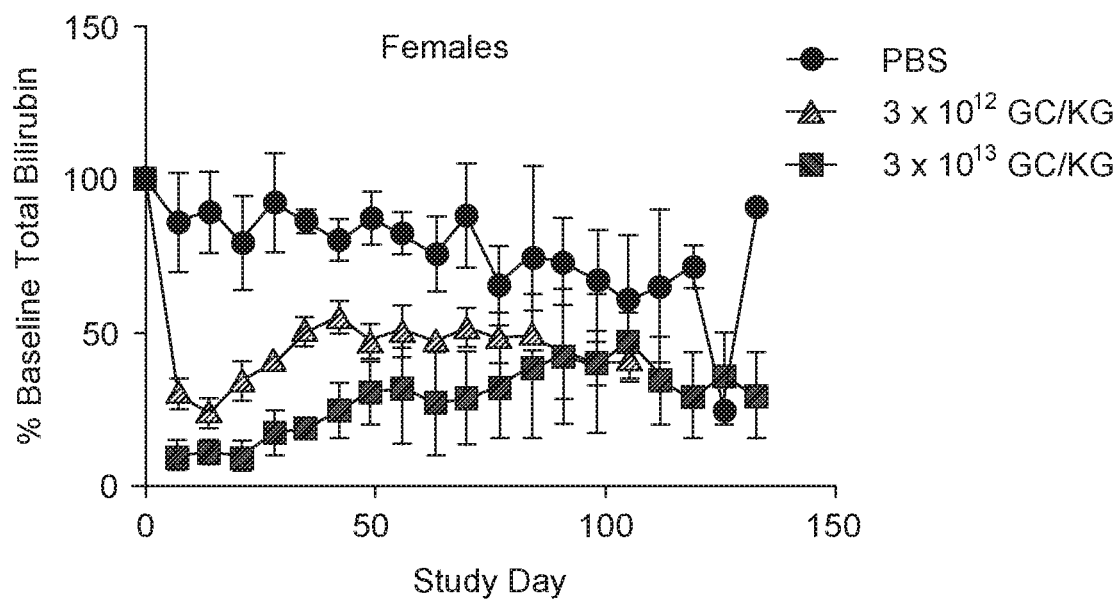
FIGS. 5A-5B are line graphs showing reduction in serum total bilirubin levels in Gunn rats following IV injection of AAV8.TBG.hUGT1A1co.WPRE.BGH. Four week old female and male Gunn rats were injected IV with 3×10¹² GC/kg (triangle) or 3×10¹³ GC/kg (square) of AAV8.TBG.hUGT1A1co.WPRE.BGH or vehicle control (phosphate buffered saline (PBS)) (circle). Total bilirubin levels were measured in serum and percentage of baseline total bilirubin values calculated. Values are presented as mean±SEM.
Figure 5B:
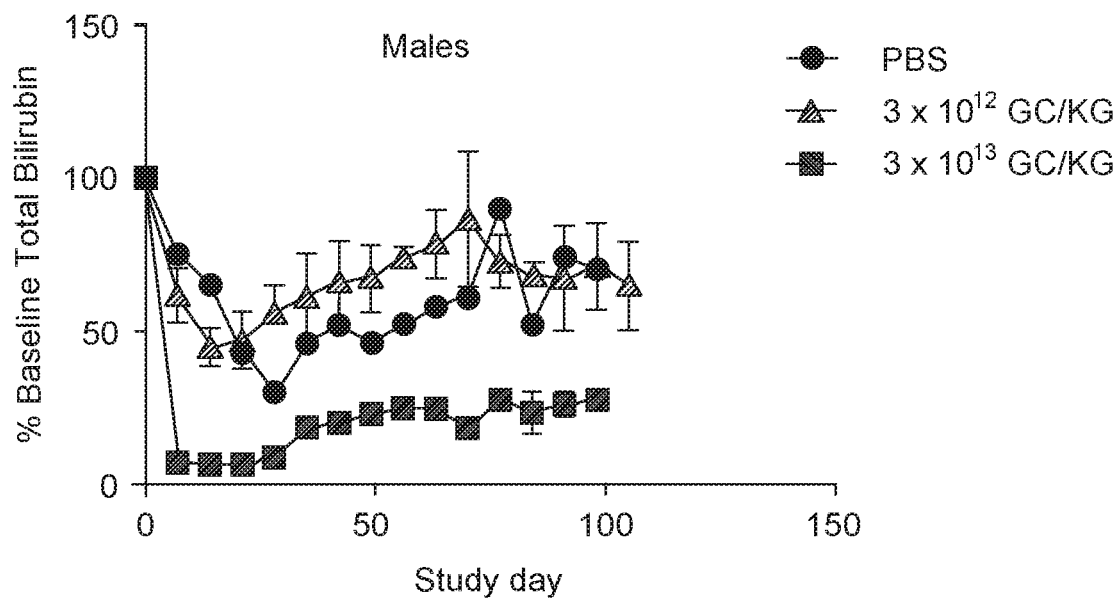

Serum total bilirubin levels were analyzed. Serum total bilirubin levels were plotted as percentage of baseline total bilirubin due to the range in baseline value. Baseline values in females ranged from 3.3-8.1 mg/dl and 3.0-7.2 mg/dl in males. Following IV administration of AAV vector, there was a dose-dependent decrease in total serum bilirubin in both female and male Gunn rats (FIGS. 5A-5B). At day 7 post-vector administration there was an average 90% reduction in total bilirubin in female Gunn rats at a dose of $3 \times 10^{13}$ GC/kg. At the lower dose of $3 \times 10^{12}$ GC/kg, there was a 70% reduction in total bilirubin in females. In male Gunn rats the effect of the high dose of vector was enhanced with a 93% reduction in total bilirubin. However, at ten-fold lower dose of the test article there was only 39% reduction in serum total bilirubin. Therefore, IV administration of $3 \times 10^{13}$ GC/kg of AAV8.TBG.hUGT1A1co.WPRE.BGH reduced the hyperbilirubinemia present in the Gunn rats to normal total bilirubin levels.

hUGT1A1 Expression by Immunohistochemistry: Gunn rats administered with the test and control articles were necropsied on days 98-133 post-vector administration and liver collected, fixed in 10% NBF, and processed for IHC staining for UGT1A1. Staining indicates hepatocytes expressing UGT1A1, which was sustained throughout the life of the rat.)

C. Conclusions

Systemic administration of $3 \times 10^{13}$ GC/kg of AAV8.TBG.hUGT1A1co.WPRE.BGH to Gunn rats reduced hyperbilirubinemia (5.4 mg/dl) to normal levels (0.1-0.3 mg/dl). Thus, the systemic administration of the first generation gene therapy vector for CN attenuated the hyperbilirubinemia characteristic to Gunn rats.

EXAMPLE 7

Non-Clinical Study Pharmacology/Toxicology Study in Non-Human Primates

A. Summary

The purpose of this study was to evaluate the potential toxicity and tolerability of AAV8.TBG.U201DPmod.BGH (termed AAV8.TBG.hUGT1A1co) following intravenous (IV) administration in rhesus macaques. For this non-clinical pharmacology/toxicology study, rhesus macaques received an infusion of one of two doses of AAV8.TBG.hUGT1A1co into a peripheral vein. The two doses used for this study were $1.0 \times 10^{13}$ and $2.5 \times 10^{13}$ genome copies (GC)/kg. A cohort of animals received infusion of a vehicle only (1× Dulbecco's phosphate buffered saline [DPBS]+0.001% Pluronic® F-68) as a vehicle control.

After vector administration, the animals were monitored daily for general observations. The nonhuman primates (NHPs) were monitored on a weekly basis for comprehensive clinical pathology (cell counts with differentials, clinical chemistries, and coagulation panel) and on a bi-weekly basis for immune reactions to the gene transfer vector (neutralizing antibodies [NAb] to AAV8 capsid, and peripheral cytotoxic T lymphocyte [CTL] responses against both the capsid and transgene assessed by IFN-γ ELISPOT assay).

On day 28 post-vector administration, a mini laparotomy procedure was performed to isolate liver tissue. Liver tissue was evaluated transgene expression by various methods, including by immunohistochemical (IHC) analysis to determine the levels of hUGT1A1 protein expression in the liver. Animals were sacrificed at day 56 post-test or control article administration. Blood was collected at necropsy for comprehensive clinical pathology and peripheral blood mononuclear cell (PBMC) isolation. Sacrificed animals were necropsied with tissues harvested for a comprehensive histopathological examination. Histopathology slides were evaluated in a blinded manner and peer reviewed. Lymphocytes were harvested from the liver, spleen, and bone marrow to examine the presence of CTLs in these organs at the time of necropsy. Samples of the liver taken at necropsy were also evaluated for transgene expression by various methods, including by IHC analysis to determine the levels of hUGT1A1 protein expression in the liver, and DNA and RNA extraction for genome copy and transgene expression analysis by qPCR and RT-PCR, respectively.

The animals tolerated the infusion of test article well without any apparent long-term or short-term clinical sequelae. Levels of vector GC in the liver were similar to those seen previously with the same capsid (AAV8) in rhesus macaques. Therefore, it was predicted that the target organ for efficacy, which is the liver, would also be the most likely source of toxicity. A detailed review of tissues harvested at necropsy on day 56 post-test or control article administration revealed some minimal to mild findings in liver. The findings in the liver included minimal to mild mononuclear cell infiltrates in the portal region, mild subcapsular fibrosis, minimal to mild bile duct hyperplasia, minimal Ito cell hyperplasia, and one minimal foreign body reaction. Other mild histopathology findings included mononuclear cell infiltrate in the myocardium, lymphoplasmacytic and mononuclear cell infiltrate in the mucosa of the colon, lymphocytic infiltrate in the rectum, lymphoplasmacytic infiltrate in the mucosa of the stomach, and mononuclear cell infiltrate in the trachea. The gastrointestinal findings occurred across the cohorts and were unrelated to dose of the test article. There was one moderate finding of mononuclear cell infiltrate in the epicardium in one animal from the low dose cohort.

Clinical pathology focused on abnormalities in transaminases. Except for one macaque in the high dose of test article group ($2.5 \times 10^{13}$ GC/kg), the elevations in ALT were <6x baseline and <4x baseline for AST (fold-change over baseline levels were determined for each macaque individually). Due to variation between animals in the dosing cohorts, the only statistically significant difference was in AST values between the high dose of test article group vs. the control group when analyzed across all time points using linear mixed-effect modelling. The elevations in ALT or AST levels did not correlate with capsid or transgene T cell responses as while the CTL response in macaques RQ9201 and RA1261 persisted to the end of the study, ALT and AST elevations were trending downwards towards baseline levels by day 56 post-test article administration. Interestingly, the observation of a highly specific T cell response to hUGT1A1 peptide pool A seen in macaque RA1846 occurred in the absence of any deviation of ALT or AST values from baseline levels. This strongly suggests that expression is not affected by the abnormalities in clinical pathology or the appearance of T cells.

As the wild type rhesus macaques used from this study do not demonstrate hyperbilirubinemia it is impossible to determine efficacy of the test article in this model. Therefore, the minimally effective dose (MED) was determined in the mouse model of CN.

Therefore, the key findings from this pharmacology/toxicology study that will inform the design of the clinical trial are:

DLTs were not observed in this toxicology study at the highest dose tested, which was $2.5 \times 10^{13}$ GC/kg in rhesus macaques. This suggests that the actual MTD is higher than this dose.

The data presented from these studies demonstrate an example of the safety of AAV8.TBG.U201DPmod.BGH for the treatment of Crigler-Najjar in rhesus macaques.

B. Materials and Methods

AAV8.TBG.U201DPmod.BGH (alternative termed AAV8.TBG.hUGT1A1co) was diluted in sterile 1× Dulbecco's phosphate buffered saline (DPBS)+0.001% Pluronic F-68. Control animals will be injected with vehicle buffer containing no test article. This will serve as the vehicle control for this study. Vehicle control (1× Dulbecco's phosphate buffered saline [DPBS]; pH 7.0-7.3; no calcium, no magnesium, no phenol red)+0.001% Pluronic® F-68) (difunctional block copolymer non-ionic surfactant terminating in primary hydroxyl groups).

Male and female rhesus macaques were used in this study. NHPs assigned to test article groups received either $1.0 \times 10^{13}$ genome copies (GC) per kilogram (kg) of body weight or $2.5 \times 10^{13}$ GC/kg of AAV8.TBG.U201DPmod.BGH in a volume of 10 ml. NHPs assigned to the control article cohort received 10 ml of vehicle control. Test and control articles were administered into a peripheral vein. The intravenous (IV) route via a peripheral vein was selected for use because it is the most efficient route used to target the liver, the clinical site of the disease.

Doses of $1.0 \times 10^{13}$ GC/kg and $2.5 \times 10^{13}$ GC/kg AAV8.TBG.U201DPmod.BGH were chosen for this study. The highest dose that we propose to administer in the clinical trial is $1.0 \times 10^{13}$ GC/kg. Therefore, for this study doses were selected that reflect a dose that is the highest dose of the clinical trial ($1.0 \times 10^{13}$ GC/kg AAV8.TBG.U201DPmod.BGH) and a dose that is 2.5-fold higher than the highest dose planned for the clinical trial ($2.5 \times 10^{13}$ GC/kg AAV8.TBG.U201DPmod.BGH).

Differences in ALT and AST levels compared to baseline levels were analyzed statistically by Wilcoxon rank sum test and overall differences in ALT and AST values across all time points using linear mixed-effect model. Comparisons between two groups were performed using unpaired Student's t-test and comparisons between multiple groups were performed using one-way analysis of variance (ANOVA, Tukey's Multiple Comparison post-test). All values expressed as mean±standard error of the mean (SEM) unless otherwise stated. Ranges of normal values for wild type rhesus macaques were generated by taking the mean of all values collected for the study animals pre-vector administration and by calculating the standard deviation (SD). The range will be presented as the mean±SD. Values outside of two SDs of the mean will be considered to be extreme values. A p value of <0.05 was considered significant.

C. Results

All rhesus macaques survived until their scheduled necropsy time point at day 56 post-test or control article administration. All rhesus macaques were visually examined each time that they were anesthetized. All changes or abnormalities were noted in the study file. There were no abnormalities noted during the course of the study. Throughout the study, the body weight of the animals was monitored at each time point listed in the study protocol. All animals either maintained their weight or continued to gradually gain weight over the course of the study.

Liver function tests (LFTs) focusing on alkaline phosphatase (ALT) and aspartate aminotransferase (AST) levels were monitored. Other parameters reflective of liver pathology, such as total bilirubin, were within normal limits throughout.

Ranges of normal values for the rhesus macaques were generated by taking the mean of all values collected for the study animals pre-vector administration and by calculating the standard deviation (SD).

| ALT (U/l) | AST (U/l) |
|---|---|
| 44 ± 27 | 29 ± 6 |

Prior to vector administration there was some variation in the baseline levels of ALT across the animals in the study, ranging from 17 U/l at day −16 for RA1260 to 110 U/l at day −7 for RA1261. ALT and AST values post-vector administration were evaluated for significant changes compared to the average baseline values (mean of days −16, −7, and 0 prior to vector administration). Differences in ALT and AST levels compared to baseline levels were analyzed statistically by Wilcoxon rank sum test. Due to the variation between animals administered with the same dose of test article, there were no significant differences between any study day post-test or control article administration. In addition, overall differences in ALT and AST values across all time points were analyzed using linear mixed-effect modelling. Again, due to the variation between animals administered with the same dose of test article, there was no significant difference in ALT values for the high dose of test article group ($2.5 \times 10^{13}$ GC/kg) vs. the control group (p value=0.142) and for the low dose of test article group ($2.5 \times 10^{13}$ GC/kg) vs. the control group (p value=0.564) or in AST values for the low dose of test article group vs. the control group (p value=0.255). There was a statistically significant difference in AST values from the high dose of test article vs. the control group (p value=0.010).

Prior to initiation of the study, all rhesus macaques were screened for neutralizing antibodies (NAbs) to AAV8 capsid by the Immunology Core at GTP. All 8 animals selected for the study were seronegative (NAb titer<1:5). Following test article administration, all animals developed an AAV8-specific NAb response. On day 8 post-vector, AAV8 NAb titers increased from <1:5 to 1:40-1:1280. There was no dose-dependent effect of test article on NAb titer as there was a similar and overlapping spread of NAb titers at day 8 following administration of either $1.0 \times 10^{13}$ GC/kg or $2.5 \times 10^{13}$ GC/kg of test article. Following day 8 post-vector administration, AAV8 NAb titers did gradually decrease at days 14 and 21 post-vector administration. Interestingly, the NAb response increased at days 28 and 35 post-vector administration and remained at similar levels until the end of the study. Control article injected animals remained seronegative or had titers of 1:5 throughout the study. Natural fluctuations in AAV8 NAb titers in non-injected animals have been described before (Calcedo et al., 2016 Hum. Gene Ther. Clin. Dev.).

Figure 6B:
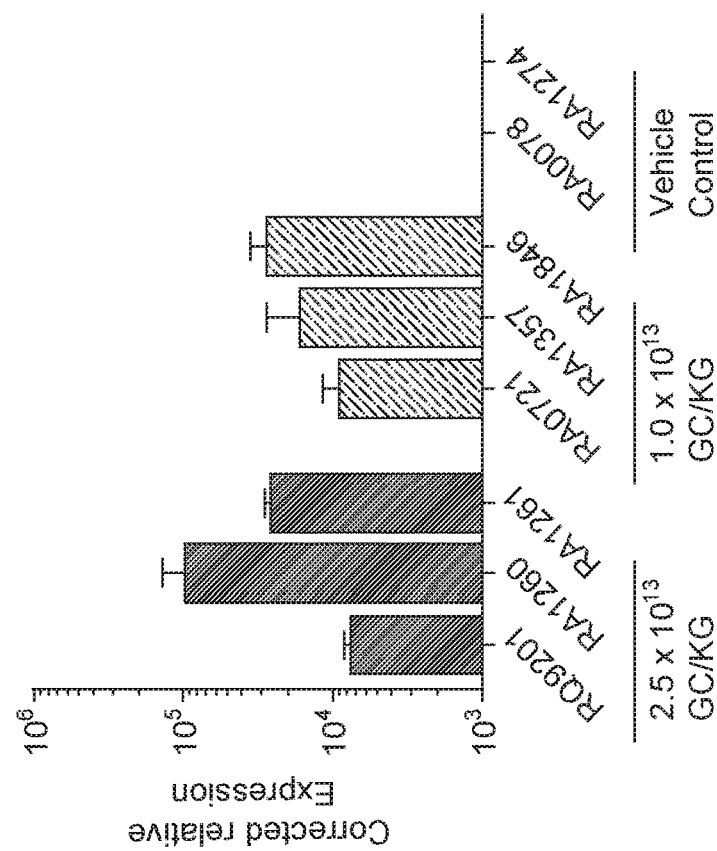
FIGS. 6A-6B are bar charts showing hUGT1A1 mRNA transcript levels in liver from test or control article injected rhesus macaques. Rhesus macaques were injected IV with 1.0×10¹³ GC/kg and 2.5×10¹³ GC/kg of AAV8.TBG.U201mod.BGH (termed AAV8.TBG.hUGT1A1co in the figure) or control article (vehicle control). At necropsy, samples from the left, middle, and right lobes of the liver were harvested and snap frozen. RNA was extracted for quantification of vector transcript levels.
Figure 6A:
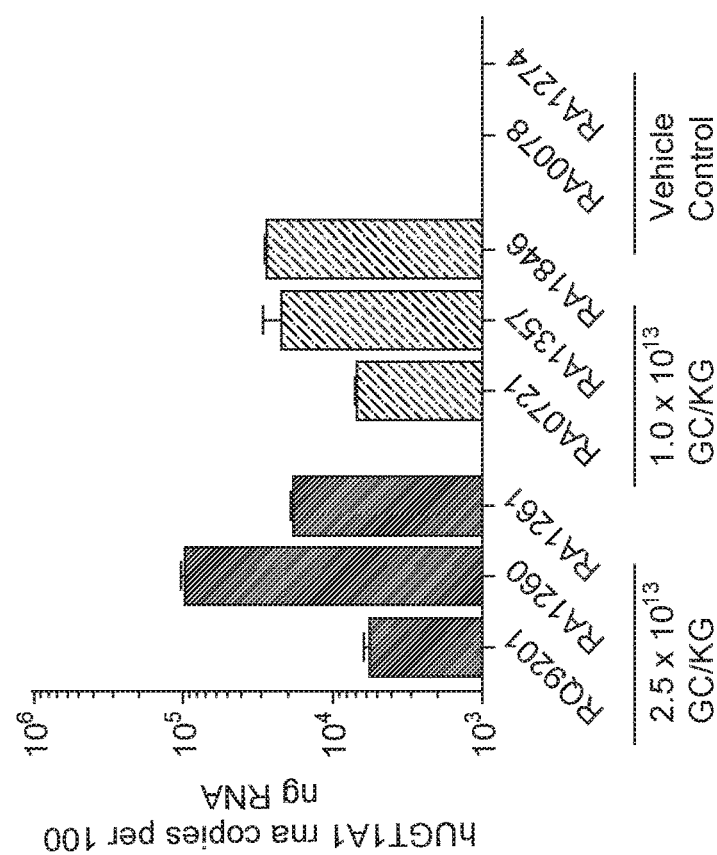

RNA was extracted from liver samples. Animals administered the high dose of test article had on average higher levels of vector GC in the liver (FIGS. 6A and 6B). Following comparison of the average corrected relative expression in the liver across the test article dose groups there was no significant difference between the test article administered groups (Student's t test, p=0.408).

D. Summary

Rhesus macaques received an infusion of one of two doses of AAV8.TBG.U201DPmod.BGH (AAV8 capsid with genome of SEQ ID NO: 15, i.e., AAV5' and 3' ITRs, two copies of alpha mic/bik enhancer, TBG promoter, hUGT1A1 of SEQ ID NO: 12, BGH polyA) into a peripheral vein. The two doses used for this study were $1.0 \times 10^{13}$ and $2.5 \times 10^{13}$ GC/kg. An additional cohort of animals received control article as a vehicle control. Blood was collected at the indicated time points for comprehensive clinical pathology. Animals were necropsied on day 56 post-test or control article administration with tissues harvested for comprehensive histopathological examination. Additional evaluations during both the in-life phase of the study and at necropsy included analysis of anti-AAV8 NAbs, AAV8 capsid-specific and hUGT1A1-specific peripheral CTL responses, CTL responses in the liver, spleen, and bone marrow, IHC for hUGT1A1 expression in liver, and determination of vector GC and transgene mRNA expression.

The animals tolerated the infusion of test article well without any apparent long-term or short-term clinical sequelae. Levels of vector GC in the liver were similar to those seen previously with the same capsid (AAV8) in rhesus macaques. Therefore, it was predicted that the target organ for efficacy, which is the liver, would also be the most likely source of toxicity. A detailed review of tissues harvested at necropsy on day 56 post-test or control article administration revealed some minimal to mild findings in liver. The findings in the liver included minimal to mild mononuclear cell infiltrates in the portal region, mild subcapsular fibrosis, minimal to mild bile duct hyperplasia, minimal Ito cell hyperplasia, and one minimal foreign body reaction. Other mild histopathology findings included mononuclear cell infiltrate in the myocardium, lymphoplasmacytic and mononuclear cell infiltrate in the mucosa of the colon, lymphocytic infiltrate in the rectum, lymphoplasmacytic infiltrate in the mucosa of the stomach, and mononuclear cell infiltrate in the trachea. The gastrointestinal findings occurred across the cohorts and were unrelated to dose of the test article. There was one moderate finding of mononuclear cell infiltrate in the epicardium in one animal from the low dose cohort.

Clinical pathology focused on abnormalities in transaminases. Except for one macaque in the high dose of test article group ($2.5 \times 10^{13}$ GC/kg), the elevations in ALT were <6× baseline and <4× baseline for AST (fold-change over baseline levels were determined for each macaque individually). Due to variation between animals in the dosing cohorts, the only statistically significant difference was in AST values between the high dose of test article group vs. the control group when analyzed across all time points using linear mixed-effect modelling. The elevations in ALT or AST levels did not correlate with capsid or transgene T cell responses as while the CTL response in macaques RQ9201 and RA1261 persisted to the end of the study, ALT and AST elevations were trending downwards towards baseline levels by day 56 post-test article administration. Interestingly, the observation of a highly specific T cell response to hUGT1A1 peptide pool A seen in macaque RA1846 occurred in the absence of any deviation of ALT or AST values from baseline levels. This strongly suggests that expression is not affected by the abnormalities in clinical pathology or the appearance of T cells.

As the wild type rhesus macaques used from this study do not demonstrate hyperbilirubinemia it is impossible to determine efficacy of the test article in this model. Therefore, the minimally effective dose (MED) was determined in the mouse model of CN.

There were no dose limiting toxicities observed, meaning that the maximally tolerated dose is equal to or greater than $2.5 \times 10^{13}$ GC/kg.

EXAMPLE 8

Non-Clinical Efficacy Study of AAV8.TBG.hUGT1A1co.BGH in the UGT1 Knockout Mouse A. Summary The purpose of this study was to determine the minimally effective dose (MED) in the CN mouse model, the UGT 1 knockout (KO) mouse. UGT1 KO mice received an intravenous (IV) injection via the tail vein of one of four doses of the vector, AAV8.TBG.U201mod.BGH (termed AAV8.TBG.hUGT1A1co in the figure and figure legend). The doses used for this study were $2.5 \times 10^{10}$, $2.5 \times 10^{11}$, $2.5 \times 10^{12}$, and $2.5 \times 10^{13}$ genome copies (GC)/kg. A cohort of animals received vehicle only (1× Dulbecco's phosphate buffered saline [DPBS]+0.001% Pluronic F-68) as a vehicle control.

Group dosing dates were staggered based on availability of UGT1 KO mice. At the initiation of the study, available mice within the dosing age range were randomly assigned to first the high dose vector group ($2.5 \times 10^{13}$ GC/kg) and the vehicle control group. Subsequently, mice were assigned to vector dose groups in the following order: $2.5 \times 10^{12}$, $2.5 \times 10^{10}$, and $2.5 \times 10^{11}$ GC/kg. After vector administration, the animals were monitored daily for general observations. Blood was collected from animals at the indicated time points to capture serum total bilirubin levels.

Animals were sacrificed on day 56 post-test or control article administration. Blood was collected at necropsy for a serum chemistry panel and hematology panel. Sacrificed animals were necropsied and tissues harvested for a comprehensive histopathological examination. Histopathology slides were evaluated in a blinded manner and peer reviewed. Where findings were observed at the highest vector dose, the same tissue at the subsequent lower vector doses was evaluated until no findings exist, or all dose groups were evaluated.

Efficacy of the test article was determined by total bilirubin levels in serum. In addition, Western blot and immunohistochemical (IHC) analysis were performed to determine the levels of hUGT1A1 protein expression in the liver.

There were no apparent clinical sequelae in any groups and abnormalities in clinical pathology were restricted to elevations in the liver transaminases ALT and AST ranged from 1-9.1× baseline for ALT and were primarily found in male mice at day 28 post-vector administration of the highest dose of the test article. The abnormalities were dose-dependent and there were essentially no findings in animals that received lower doses of the test article. While there were histopathological findings in male mice administered with the control article, the majority of the findings were in male mice administered with the highest dose of the test article ($2.5 \times 10^{13}$ GC/kg) but all findings were minimal to mild. Therefore, it was concluded that there were no dose limiting toxicities seen, meaning that the maximally tolerated dose was greater than or equal to the highest dose tested, which was $2.5 \times 10^{13}$ GC/kg. The presence of increased liver pathology (minimal to mild) at this dose, suggested it is related to the test article, indicating that the no effect dose is the next lower dose of $2.5 \times 10^{12}$ GC/kg.

The conduct of this study in the animal model of CN allowed the MED to be estimated. At doses of the test article greater than $2.5 \times 10^{10}$ GC/kg, there was a complete reversal of total bilirubin levels to baseline levels of 0.1-0.3 mg/dl. Administration of $2.5 \times 10^{10}$ GC/kg resulted in a 79% reduction in serum total bilirubin levels in male mice at day 14 post-vector administration, which gradually increased to a 57% reduction at day 28, and returned to baseline hyperbilirubinemia by day 42 and administration of the same dose in a single female UGT1 KO mouse did not result in a deviation from baseline values. While there was a sex difference with respect to expression of hUGT1A1 in UGT1 KO mice, this has not been seen to translate to nonhuman primates. Therefore, the MED is equal to $2.5 \times 10^{11}$ GC/kg.

B. Methods

AAV8.TBG.U201DPmod.BGH was diluted in sterile 1× Dulbecco's phosphate buffered saline (DPBS)+0.001% Pluronic F-68. Vehicle control (1× Dulbecco's phosphate buffered saline [DPBS]+0.001% Pluronic F-68)

Male and female UGT1 KO mice (n=50, 25 male and 25 female) 6 to 20 weeks in age were used in this study and necropsied at day 56 post-vector administration. Animals were ear tagged and assigned to one of five cohorts.

The IV route via the tail vein was selected for use because it is the most efficient route used to target the liver, which in humans is the clinical site of the disease.

Multiple dose levels of AAV8.TBG.U201DPmod.BGH were examined. The highest dose was $2.5 \times 10^{13}$ GC/kg, which is 2.5-fold higher than the highest dose of a proposed clinical trial. The doses selected differed by one log and were $2.5 \times 10^{10}$ GC/kg, $2.5 \times 10^{11}$ GC/kg, $2.5 \times 10^{12}$ GC/kg, and $2.5 \times 10^{13}$ GC/kg. Each group included 5 animals of each sex. Five animals per group is the minimal number to enable statistical analysis of study outcome.

Efficacy of the test article was determined by total bilirubin levels in serum. In addition, Western blot and immunohistochemical (IHC) analysis were performed to determine the levels of hUGT1A1 protein expression in the liver.

For body weight, food consumption, ALT, AST, total bilirubin, Western blot quantification, vector GC, and hUGT1A1 mRNA transcript data, cohort average and standard error of the mean (SEM) was calculated and reported. Differences in ALT, AST and total bilirubin levels compared to baseline levels were analyzed statistically by Wilcoxon rank sum test and overall differences in ALT, AST, and total bilirubin values across all time points using linear mixed-effect model. Comparisons between two groups were performed using unpaired Student's t-test and comparisons between multiple groups were performed using one-way analysis of variance (ANOVA, Tukey's Multiple Comparison post-test). All values expressed as mean±SEM unless otherwise stated. A p value of <0.05 was considered significant.

C. Results

During the course of the study mouse ID 5205 was euthanized on day 8 post-vector administration for clinical signs (displayed moribund condition thus requiring euthanasia for humane reasons). A full necropsy was performed and tissues were collected. Following test or control article administration, animals were monitored daily for general observations. All changes or abnormalities were noted in the study file. With the exception of mouse ID 5205 that was euthanized prior to the necropsy time point, there were observations recorded for 10 out of the 41 mice enrolled on the study that did not affect study outcome. Seven of these 10 mice required treatment with supportive care during the in-life phase of the study.

Blood chemistry results were evaluated for statistical change ($p<0.05$) compared to mice administered with the control article (100 µl of vehicle control) at each time point. Of interest were three distinct parameters; total bilirubin, ALT, and AST as there were consistent substantial differences between groups.

The abnormalities in liver function tests (LFTs) increased with the increasing dose of the test article and elevations greater than 4× baseline (colored orange and red) were restricted to the highest dose group ($2.5\times10^{13}$ GC/kg), with the exception of one male mouse in the lowest dose group ($2.5\times10^{10}$ GC/kg) at day 14 and one male mouse that received a dose of $2.5\times10^{11}$ GC/kg at day 28 post-test article administration. Elevations of AST gave a similar pattern but the elevations were limited to <4× baseline (colored green and blue), with the exception of one female mouse that received a dose of $2.5\times10^{12}$ GC/kg at day 56 post-test article administration.

Comparison of ALT and AST levels across the cohorts was performed using linear mixed effect modelling and stratified by sex. For ALT, there was a significant elevation compared to the control group observed in both male and female mice administered with the highest dose of the test article, $2.5\times10^{13}$ GC/kg ($p=0.015$ for males, $p=0.049$ for females). A significant elevation in AST was only observed in female mice administered with the highest test article dose compared to the control group ($p=0.042$).

Figure 7:
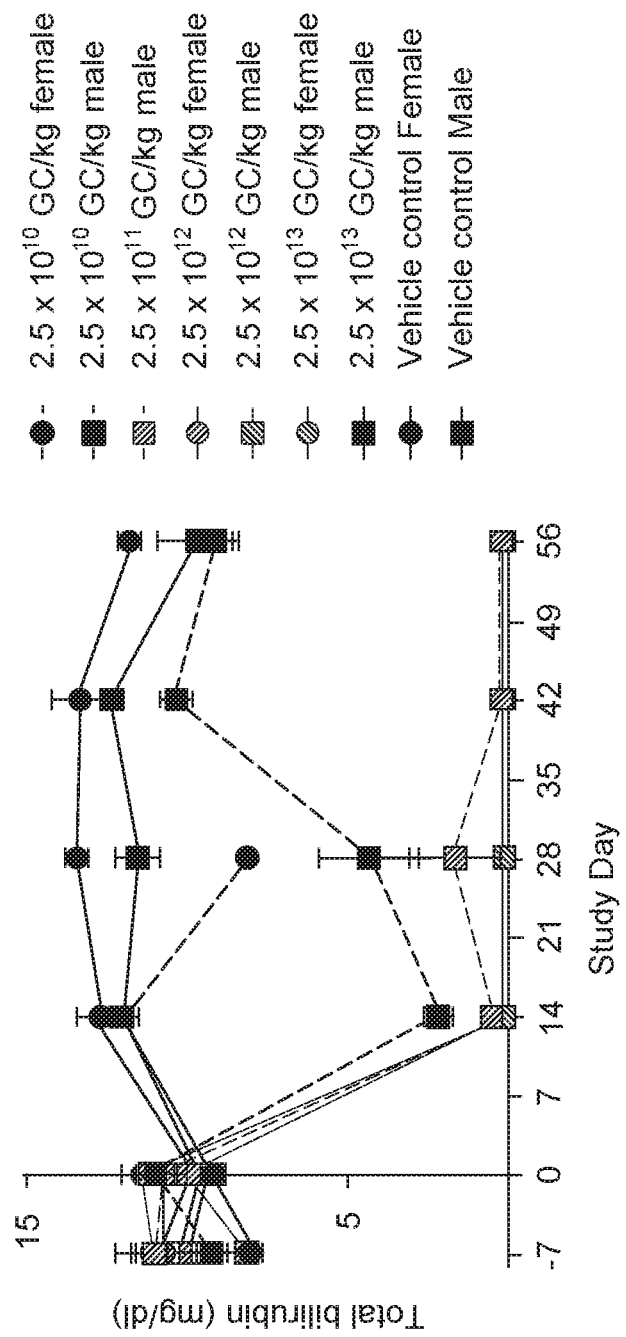
FIG. 7. Total bilirubin levels in test or control article injected UGT1 KO mice. Male and female UGT1 KO mice were injected IV with 2.5×10¹⁰ GC/kg, 2.5×10¹¹ GC/kg, 2.5×10¹² GC/kg, and 2.5×10¹³ GC/kg of AAV8.TBG.U201mod.BGH (termed AAV8.TBG.hUGT1A1co in the figure) or control article (100 µl of vehicle control). Total bilirubin levels were measured in serum samples taken. Values expressed as mean±SEM.
Figure 8:
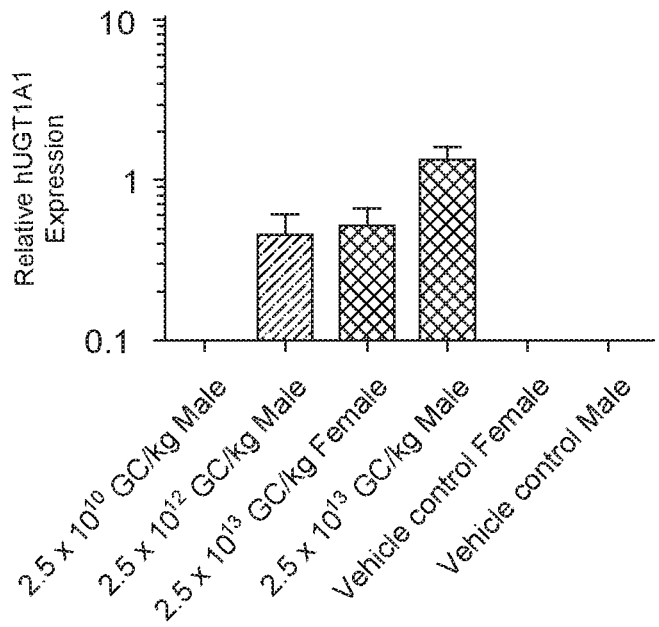
FIG. 8 is a bar chart showing quantification of Western blots for hUGT1A1 expression in liver homogenates from test or control article injected UGT1 KO mice. Male and female UGT1 KO mice were injected IV with 2.5×10¹⁰ GC/kg, 2.5×10¹¹ GC/kg, 2.5×10¹² GC/kg, and 2.5×10¹³ GC/kg of AAV8.TBG.U201mod.BGH (termed AAV8.TBG.hUGT1A1co in the figure) or control article (100 µl of vehicle control). At necropsy, livers were harvested and liver homogenates made. 1 µg of protein isolated from liver homogenate was run by Western blot with a human UGT1A1-specific antibody used for detection. Images of bands were quantified against the same amount of protein from a positive control sample. Values plotted as mean±SEM (n=5 mice/group). Bands for male mice injected with 2.5×10¹⁰ GC/kg were below the limit of detection.

Total bilirubin levels in UGT1 KO mice injected with the control article (vehicle control) were similar across all time points with no variation in levels between males and females (FIG. 6). As expected we observed a rapid and significant reduction of total bilirubin by day 14 post-vector administration in both male and female mice treated at all doses of the test article ($2.5\times10^{10}$ GC/kg, $2.5\times10^{11}$ GC/kg, $2.5\times10^{12}$ GC/kg, and $2.5\times10^{13}$ GC/kg of AAV8.TBG.U201DPmod.BGH). At doses of the test article greater than $2.5\times10^{10}$ GC/kg, there was a complete reversal of total bilirubin levels to baseline levels of 0.1-0.3 mg/dl (FIG. 7). Administration of $2.5\times10^{10}$ GC/kg resulted in a 79% reduction in serum total bilirubin levels in male mice at day 14 post-vector administration, which gradually increased to a 57% reduction at day 28, and returned to baseline hyperbilirubinemia by day 42 (FIG. 7). Administration of the same dose in a single female UGT1 KO mouse did not result in a deviation from baseline values.

Comparison of total bilirubin levels across the cohorts was performed using linear mixed effect modelling and stratified by sex. A significant reduction in total bilirubin compared to the control group was observed in males for all dose groups and for female mice dosed with $2.5\times10^{12}$ GC/kg and $2.5\times10^{13}$ GC/kg ($p<0.05$).

At the time of necropsy, liver was harvested for determination of hUGT1A1 transgene expression. Liver samples were snap frozen and stored at −80° C. prior to use. Expression was evaluated by detection of hUGT1A1 protein levels by Western blot on liver homogenates. Human UGT1A1-specific antibodies were used for detection and Western blot images were quantified against the same amount of protein from a positive control sample. Expression of hUGT1A1 in male mice increased significantly with dose of the test article from $2.5\times10^{12}$ GC/kg to $2.5\times10^{13}$ GC/kg ($p<0.05$, FIG. 8). Bands for male mice injected with $2.5\times10^{11}$ GC/kg were below the limit of detection.

Figure 9A:
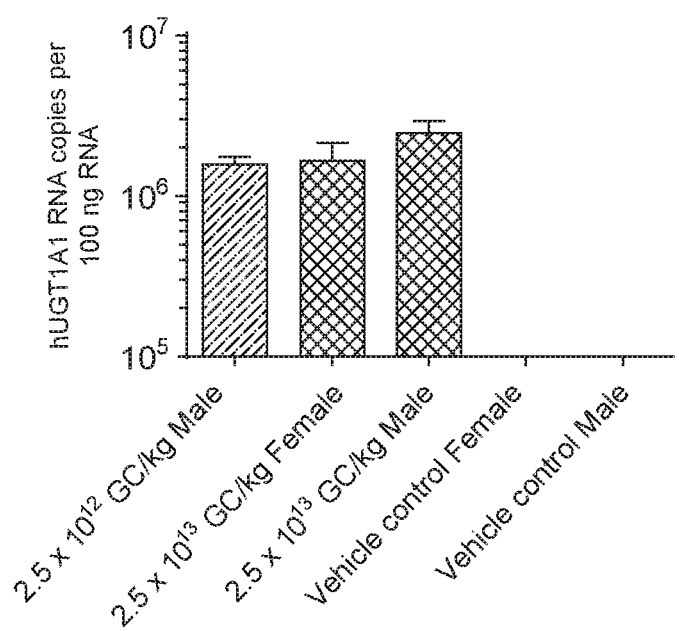
FIGS. 9A-9B are bar charts showing hUGT1A1 mRNA transcript levels in liver from test or control article injected UGT1 KO mice. Male and female UGT1 KO mice were injected IV with 2.5×10¹⁰ GC/kg, 2.5×10¹¹ GC/kg, 2.5×10¹² GC/kg, and 2.5×10¹³ GC/kg of AAV8.TBG.U201DPmod.BGH (termed AAV8.TBG.hUGT1A1co in the figures) or control article (100 µl of vehicle control). At necropsy, livers were harvested and snap frozen. RNA was extracted for quantification of vector transcript levels. (A) hUGT1A1 RNA copies presented per 100 ng of RNA. (B) Corrected relative expression of hUGT1A1 RNA levels. Values plotted as mean±SEM (n=5 mice/group).
Figure 9B:
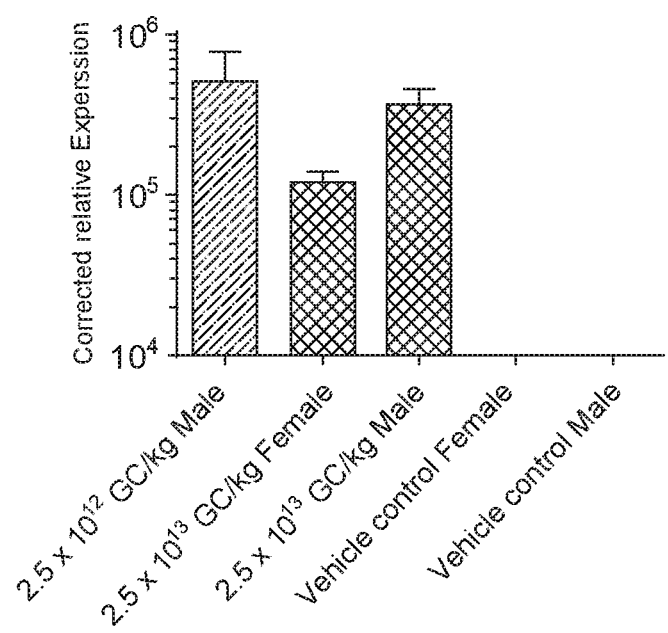
Figure 10B:
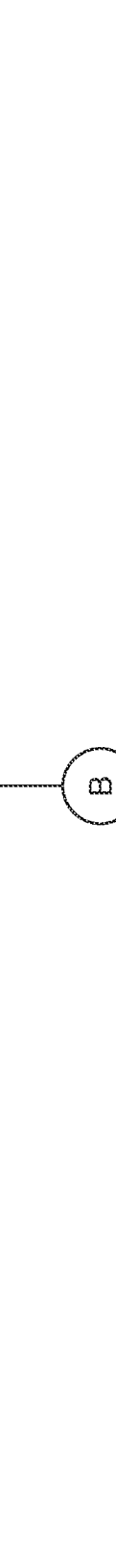
Figure 10B:
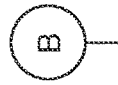
Figure 10C:
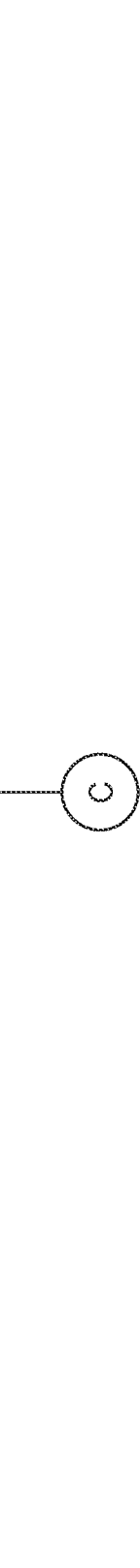
Figure 10D:
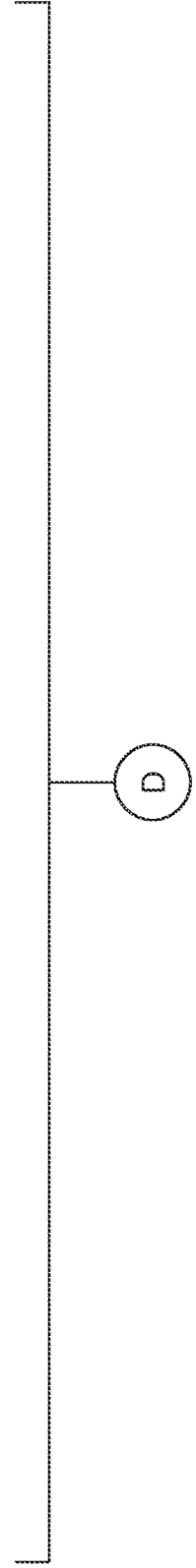

RNA was extracted from liver samples. TaqMan qPCR reactions were performed. Expression of hUGT1A1 mRNA transcript in the liver of male mice did not significantly differ with dose of the test article from $2.5\times10^{12}$ GC/kg to $2.5\times10^{13}$ GC/kg (FIGS. 9A-9B).

D. Summary of Results

Male and female UGT1 KO mice 6-20 weeks of age were administered IV with one of four doses [$2.5\times10^{10}$, $2.5\times10^{11}$, $2.5\times10^{12}$, and $2.5\times10^{13}$ GC/kg] of AAV8.TBG.U201DPmod.BGH. The doses chosen were to reflect the span of the proposed dosing regimen of the clinical trial. An additional cohort of animals received control article as a vehicle control. Blood was collected from animals at the indicated time points to capture total bilirubin levels. Animals were necropsied on day 56 post-test or control article administration with tissues harvested for comprehensive histopathological examination. Additionally, blood was collected for serum chemistry panel and hematology panel.

A number of factors were considered in the design of this study. First, we selected to conduct the experiments in UGT1 KO mice (rather than in C57BL/6J mice) for two reasons. First, using this strain of mice would allow us to evaluate efficacy in parallel with toxicity. Second, we wanted to evaluate vector-associated toxicity in the setting of any pathology associated with the defect in UGT1A1, and the associated hyperbilirubinemia and its sequelae. While we did not expect there to be liver pathology in the model, we were concerned that some level of chronic severe hyperbilirubinemia could influence the response of the host liver to vector.

The key findings are as follows:

No clinical sequelae

Efficacy

At doses of the test article greater than $2.5\times10^{10}$ GC/kg, there was a complete reversal of total bilirubin levels to baseline levels of 0.1-0.3 mg/dl.

A significant reduction in total bilirubin compared to the control group was observed in males for all four dose groups ($2.5\times10^{10}$-$2.5\times10^{13}$ GC/kg) and for female mice dosed with $2.5\times10^{12}$ GC/kg and $2.5\times10^{13}$ GC/kg ($p<0.05$).

Administration of $2.5\times10^{10}$ GC/kg resulted in a 79% reduction in serum total bilirubin levels in male mice at day 14 post-vector administration, which gradually increased to a 57% reduction at day 28, and returned to baseline hyperbilirubinemia by day 42.

Administration of the same dose in a single female UGT1 KO mouse did not result in a deviation from baseline values.

The sex difference seen in expression in mice has not been seen to translate to nonhuman primates. Therefore, the MED is equal to $2.5\times10^{11}$ GC/kg.

Clinical pathology

Transaminases: Abnormalities were limited to elevations of the liver function tests ALT and AST that ranged from 1-9.1× baseline for ALT and were primarily found in male mice at day 28 post-vector administration of the highest doses of test article. The abnormalities were dose-dependent and there were essentially no findings in animals that received lower doses of the test article. Therefore, we conclude that the no effect dose based on these criteria is $2.5\times10^{12}$ GC/kg.

Pathology: There were three gross observations, none of which involved the liver (the target organ for this gene therapy approach). Histopathology was limited to minimal or mild findings in liver as follows:

Control article administered male and female mice had no abnormalities detected, with the exception of minimal findings of centrilobular single cell hepatocellular necrosis/degeneration and intracanalicular bile stasis in one male mouse.

Overall, there were fewer findings in the liver of female mice. Only minimal findings were observed of centrilobular single cell hepatocellular necrosis/degeneration and mononuclear cell infiltration in one mouse administered with the high dose of the test article ($2.5 \times 10^{13}$ GC/kg) and one mouse administered with $2.5 \times 10^{12}$ GC/kg. In addition, the female mouse administered with $2.5 \times 10^{12}$ GC/kg also had hepatocellular mitotic figures and bile stasis.

Minimal centrilobular single cell hepatocellular necrosis/degeneration was seen in all cohorts of male UGT1 KO mice. However, in the high dose of test article cohort ($2.5 \times 10^{13}$ GC/kg) there were also two mild findings of centrilobular single cell hepatocellular necrosis/degeneration. This cohort also displayed minimal findings of mononuclear cell infiltration, hepatocellular mitotic figures and bile stasis.

Tissues other than the liver were only reviewed for the high dose test article ($2.5 \times 10^{13}$ GC/kg) and control article administered mice. The only other observations were findings in the lung (minimal and mild accumulation of acidophilic material in alveolar macrophages in male and female mice administered with the control article), uterus (minimal focal subacute inflammation in one female mouse administered with the control article), and skin of the injection site (dermal fibrosis in one female mouse administered with the high dose of the test article).

There were no dose limiting toxicities seen, meaning that the maximally tolerated dose was greater than or equal to the highest dose tested, which was $2.5 \times 10^{13}$ GC/kg Based on mild findings in liver pathology at the highest dose ($2.5 \times 10^{13}$ GC/kg), we propose the no effect dose to be next lower dose of $2.5 \times 10^{12}$ GC/kg The MED is equal to $2.5 \times 10^{11}$ GC/kg.

Sequence Listing Free Text

The following information is provided for sequences containing free text under numeric identifier <223>.

| SEQ ID NO: (containing free text) | Free text under <223> |
|---|---|
| 1 | <223> Engineered UGT1A1 sequence U001 |
| 2 | <223> Engineered UGT1A1 sequence U011TY |
| 3 | <223> Engineered UGT1A1 sequence U201DP |
| 4 | <223> Engineered UGT1A1 sequence |
| 7 | <223> optimized UGT1A1 v2.1 |
| 8 | <223> optimized UGT1A1 v3 |
| 9 | <223> pAAV.TBG.hUGT1A1co.WRPE.BGH (p3793) vector<br><220><br><221> repeat_region<br><222> (1) . . . (168)<br><223> 5' ITR<br><220><br><221> enhancer<br><222> (211) . . . (310)<br><223> alpha mic/bik<br><220><br><221> enhancer<br><222> (317) . . . (416)<br><223> alpha mic/bik<br><220><br><221> promoter<br><222> (431) . . . (907)<br><223> TBG promoter<br><220><br><221> Intron<br><222> (939) . . . (1071)<br><223> SV40 misc intron (Promega)<br><220><br><221> misc_feature<br><222> (1086) . . . (1091)<br><223> Kozak<br><220><br><221> misc_feature<br><222> (1092) . . . (2690)<br><223> UGT1A1 CDS<br><220><br><221> misc_feature<br><222> (2709) . . . (3250)<br><220><br><221> polyA_signal<br><222> (3257) . . . (3471)<br><223> BGH polyA<br><220><br><221> repeat_region<br><222> (3521) . . . (3558)<br><223> 3' ITR<br><220><br><221> misc_feature<br><222> (4451) . . . (5308)<br><223> Amp-R CDS<br><220><br><221> misc_feature<br><222> (5482) . . . (6070)<br><223> origin |
| 10 | <223> pAAV.TBG.hUGT1A1co.BGH<br><220><br><221> repeat_region<br><222> (1) . . . (168)<br><223> 5' ITR<br><220><br><221> enhancer<br><222> (211) . . . (310)<br><223> alpha mc/bik<br><220><br><221> enhancer<br><222> (317) . . . (416)<br><223> alpha mc/bik<br><220><br><221> promoter<br><222> (431) . . . (907)<br><223> TBG promoter<br><220><br><221> Intron<br><222> (939) . . . (1071)<br><223> SV40 misc intron (Promega)<br><220><br><221> misc_feature<br><222> (1086) . . . (1091)<br><223> Kozak<br><220><br><221> misc_feature<br><222> (1092) . . . (2690)<br><223> UGT1A1 coding sequence<br><220><br><221> repeat_region<br><222> (2695) . . . (3152)<br><223> 3' ITR<br><220> |

| SEQ ID NO: (containing free text) | Free text under <223> |
|---|---|
| | <221> polyA_signal |
| | <222> (2721) ... (2935) |
| | <223> BGH polyA |
| | <220> |
| | <221> misc_feature |
| | <222> (3915) ... (4772) |
| | <223> Amp-R coding sequence |
| | <220> |
| | <221> misc_feature |
| | <222> (4946) ... (4772) |
| | <223> origin |
| 11 | <223> AAV8 VP1 capsid protein |
| 12 | <223> engineered UGT1A1 U201DPmod |
| 13 | <223> engineered UGT1A1 U001mod |
| 14 | <223> engineered UGT1A1 U011TYmod |
| 15 | <223> pAAV.TGB.U201DP.BGH (p4120) |
| | <220> |
| | <221> repeat_region |
| | <222> (1) ... (168) |
| | <223> 5' ITR |
| | <220> |
| | <221> enhancer |
| | <222> (211) ... (310) |
| | <223> alpha mic/bik enhancer |
| | <220> |
| | <221> enhancer |
| | <222> (317) ... (416) |
| | <223> alpha mic/bik enhancer |
| | <220> |
| | <221> promoter |
| | <222> (431) ... (907) |
| | <223> TBG promoter |
| | <220> |
| | <221> Intron |
| | <222> (939) ... (1071) |
| | <223> SV40 misc intron (Promega) |
| | <220> |
| | <221> misc_feature |
| | <222> (1092) ... (2690) |
| | <223> U201DPmod CDS |
| | <220> |
| | <221> polyA_signal |
| | <222> (2709) ... (2923) |
| | <223> BGH polyA |
| | <220> |
| | <221> repeat_region |
| | <222> (2973) ... (3140) |
| | <223> AAV 3' ITR |
| 16 | <223> pAAV.TBG.U011TY.BGH |

| SEQ ID NO: (containing free text) | Free text under <223> |
|---|---|
| | (p4119) |
| | <220> |
| | <221> repeat_region |
| | <222> (1) ... (168) |
| | <223> AAV 5' ITR |
| | <220> |
| | <221> enhancer |
| | <222> (211) ... (310) |
| | <223> alpha mic/bik |
| | <220> |
| | <221> enhancer |
| | <222> (317) ... (416) |
| | <223> alpha mic/bik |
| | <220> |
| | <221> promoter |
| | <222> (431) ... (907) |
| | <223> TBG promoter |
| | <220> |
| | <221> Intron |
| | <222> (939) ... (1071) |
| | <223> SV40 misc intron (Promega) |
| | <220> |
| | <221> misc_feature |
| | <222> (1092) ... (2690) |
| | <223> CDS for modfied U011TY |
| | <220> |
| | <221> polyA |
| | <222> (2709) ... (2923) |
| | <223> BGH polyA |
| | <220> |
| | <221> repeat_region |
| | <222> (2973) ... (3140) |
| | <223> AAV 3'ITR |
| 17 | <223> pAAV.TBG.U001.BGH (p4118) |
| 18 | <223> engineered UG1A1 U3G |

All publications, patents, patent applications, cited in this application and the Sequence Listing referenced herein, as well as U.S. Provisional Patent Applications No. 62/348,029, filed Jun. 9, 2016, and No. 62/266,969, filed Dec. 14, 2015, are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

The invention claimed is:

1. An adeno-associated virus (AAV) vector comprising an AAV capsid and a vector genome comprising a UGT1A1 coding sequence operably linked to expression control sequences which direct transcription and/or expression of human UGT1A1, wherein the UGT1A1 coding sequence is:
   (a) SEQ ID NO: 12;
   (b) SEQ ID NO: 13;
   (c) SEQ ID NO: 14;
   (d) SEQ ID NO: 3;
   (e) SEQ ID NO: 2; or
   (f) SEQ ID NO: 1;
   or a sequence at least 99% identical to SEQ ID NO: 12, 13, 14, 3, 2, or 1 that encodes human UGT1A1.

2. The AAV vector according to claim 1, wherein the AAV capsid is an AAV8 capsid or an AAVhu.37 capsid.

3. The AAV vector according to claim 1, wherein the expression control sequences comprise a liver-specific promoter.

4. The AAV vector according to claim 1, wherein the UGT1A1 coding sequence is SEQ ID NO: 12 or SEQ ID NO: 3.

5. The AAV vector according to claim 1, wherein the expression control sequences comprise multiple enhancers.

6. The AAV vector according to claim 1, wherein the vector genome comprises: (a) nucleotides 1 to 3140 of SEQ ID NO: 15, which comprises SEQ ID NO: 12; (b) nucleotides 1 to 3140 of SEQ ID NO: 16, which comprises SEQ ID NO: 14; or (c) nucleotides 1 to 3140 of SEQ ID NO: 17, which comprises SEQ ID NO: 13.

7. The AAV vector according to claim 6, wherein the vector comprises an AAV8 capsid or an AAVhu.37 capsid.

8. A composition comprising the AAV vector according to claim 1 in a formulation buffer.

9. The composition according to claim 8, wherein the formulation buffer comprises phosphate buffered saline and a surfactant.

10. A method for treating a patient having Crigler-Najjar syndrome type I or II, or Gilbert syndrome, comprising administering an effective amount of the composition according to claim 8.

11. The method according to claim 10, wherein the patient is co-treated with an immunosuppressive and/or phototherapy.

12. A plasmid comprising a UGT1A1 coding sequence comprising:
   (a) SEQ ID NO: 12;
   (b) SEQ ID NO: 13;
   (c) SEQ ID NO: 14;
   (d) SEQ ID NO: 3;
   (e) SEQ ID NO: 2;
   (f) SEQ ID NO: 1; or
   a sequence at least 99% identical to SEQ ID NO: 12, 13, 14, 3, 2, or 1 that encodes human UGT1A1.

13. A composition comprising the plasmid according to claim 12 and a pharmaceutically acceptable carrier, diluent, and/or excipient.

14. A method for treatment of Crigler-Najjar syndrome type I or II, or Gilbert syndrome comprising administering an effective amount of the composition according to claim 13.

15. An adeno-associated virus (AAV) vector comprising an AAV capsid and a vector genome comprising
   (a) a 5' AAV inverted terminal repeat (ITR);
   (b) a thyroxin-binding globulin (TBG) promoter;
   (c) a UGT1A1 coding sequence operably linked to expression control sequences which direct transcription and/or expression of human UGT1A1, wherein the UGT1A1 coding sequence is SEQ ID NO: 12, or a sequence at least 99% identical to SEQ ID NO: 12 that encodes UGT1A; and
   (d) a 3' AAV ITR.

16. The AAV vector according to claim 15, wherein the AAV capsid is an AAV8 capsid or an AAVhu.37 capsid.

17. The AAV vector according to claim 15, wherein the UGT1A1 coding sequence is SEQ ID NO: 12 or the UGT1A coding sequence at least 99% identical to SEQ ID NO: 12 is SEQ ID NO: 3.

18. The AAV vector according to claim 15, wherein the vector genome further comprises one or more elements selected from the group consisting of an alpha microglobulin/bikunin enhancer, an intron, and a bovine growth hormone polyA.

19. The AAV vector according to claim 15, wherein the vector genome is SEQ ID NO: 15, which comprises SEQ ID NO: 12.

20. A composition comprising the AAV vector according to claim 15 and a pharmaceutically acceptable carrier, diluent, and/or excipient.

21. The plasmid according to claim 12, wherein the UGT1A1 coding sequence is flanked by a 5' AAV ITR and a 3' AAV ITR.

22. The plasmid of claim 21 comprising:
   (a) nucleotides 1 to 3140 of SEQ ID NO: 15, which comprises SEQ ID NO: 12;
   (b) nucleotides 1 to 3140 of SEQ ID NO: 16, which comprises SEQ ID NO: 14; or
   (c) nucleotides 1 to 3140 of SEQ ID NO: 17, which comprises SEQ ID NO: 13.

* * * * *

SEQUENCE LISTING

<160> NUMBER OF SEQ ID NOS: 18

<210> SEQ ID NO 1
<211> LENGTH: 1599
<212> TYPE: DNA
<213> ORGANISM: Artificial Sequence
<220> FEATURE:
<223> OTHER INFORMATION: Engineered UGT1A1 sequence U001

<400> SEQUENCE: 1

```
atggccgtgg agagccaggg ggggcggccc ctggtgctgg ggctgctgct gtgcgtgctg      60
gggcccgtgg tgagccacgc cgggaagatc ctgctgatcc ccgtggacgg gagccactgg     120
ctgagcatgc tgggggccat ccagcagctg cagcagcggg ggcacgagat cgtggtgctg     180
```

| | |
|---|---:|
| gcccccgacg ccagcctgta catccgggac ggggccttct acaccctgaa gacctacccc | 240 |
| gtgcccttcc agcgggagga cgtgaaggag agcttcgtga gcctgggca caacgtgttc | 300 |
| gagaacgaca gcttcctgca gcgggtgatc aagacctaca gaagatcaa gaaggacagc | 360 |
| gccatgctgc tgagcgggtg cagccacctg ctgcacaaca aggagctgat ggccagcctg | 420 |
| gccgagagca gcttcgacgt gatgctgacc gaccccttcc tgccctgcag ccccatcgtg | 480 |
| gcccagtacc tgagcctgcc caccgtgttc ttcctgcacg ccctgccctg cagcctggag | 540 |
| ttcgaggcca cccagtgccc caaccccttc agctacgtgc cccggcccct gagcagccac | 600 |
| agcgaccaca tgaccttcct gcagcgggtg aagaacatgc tgatcgcctt cagccagaac | 660 |
| ttcctgtgcg acgtggtgta cagcccctac gccaccctgg ccagcgagtt cctgcagcgg | 720 |
| gaggtgaccg tgcaggacct gctgagcagc gccagcgtgt ggctgttccg gagcgacttc | 780 |
| gtgaaggact accccggcc catcatgccc aacatggtgt tcgtggggg gatcaactgc | 840 |
| ctgcaccaga ccccctgag ccaggagttc gaggcctaca tcaacgccag cggggagcac | 900 |
| gggatcgtgg tgttcagcct ggggagcatg gtgagcgaga tccccgagaa gaaggccatg | 960 |
| gccatcgccg acgccctggg aagatcccc cagaccgtgc tgtggcggta caccgggacc | 1020 |
| cggcccagca acctggccaa caacaccatc ctggtgaagt ggctgcccca gaacgacctg | 1080 |
| ctggggcacc ccatgacccg ggccttcatc acccacgccg ggagccacgg ggtgtacgag | 1140 |
| agcatctgca cggggtgcc catggtgatg atgcccctgt cggggaccga gatggacaac | 1200 |
| gccaagcgga tggagaccaa gggggccggg gtgaccctga acgtgctgga gatgaccagc | 1260 |
| gaggacctgg agaacgccct gaaggccgtg atcaacgaca gagctacaa ggagaacatc | 1320 |
| atgcggctga gcagcctgca caaggaccgg cccgtggagc ccctggacct ggccgtgttc | 1380 |
| tgggtggagt cgtgatgcg gcacaagggg gccccccacc tgcggcccgc cgcccacgac | 1440 |
| ctgacctggt accagtacca cagcctggac gtgatcgggt tcctgctggc cgtggtgctg | 1500 |
| accgtggcct tcatcacctt caagtgctgc gcctacgggt accggaagtg cctggggaag | 1560 |
| aagggggcgg tgaagaaggc ccacaagagc aagacccac | 1599 |

<210> SEQ ID NO 2
<211> LENGTH: 1599
<212> TYPE: DNA
<213> ORGANISM: Artificial Sequence
<220> FEATURE:
<223> OTHER INFORMATION: Engineered UGT1A1 sequence U011TY

<400> SEQUENCE: 2

| | |
|---|---:|
| atggctgtgg aaagccaggg cggccggccc ctggtgctgg gcctgctgct gtgtgtgctg | 60 |
| ggccccgtgg tgagccacgc tggcaagatt ctgctgattc ccgtggacgg cagccactgg | 120 |
| ctgagcatgc tgggcgctat tcagcagctg cagcagcggg ccacgaaat tgtggtgctg | 180 |
| gctcccgacg ctagcctgta cattcgggac ggcgcttttt acaccctgaa gacctacccc | 240 |
| gtgcccttc agcgggaaga cgtgaaggaa agctttgtga gcctgggcca caacgtgttt | 300 |
| gaaaacgaca gctttctgca gcgggtgatt aagacctaca gaagattaa gaaggacagc | 360 |
| gctatgctgc tgagcggctg tagccacctg ctgcacaaca aggaactgat ggctagcctg | 420 |
| gctgaaagca gctttgacgt gatgctgacc gaccccttc tgccctgtag ccccattgtg | 480 |
| gctcagtacc tgagcctgcc caccgtgttt tttctgcacg ctctgccctg tagcctggaa | 540 |
| tttgaagcta cccagtgtcc caaccccttt agctacgtgc cccggcccct gagcagccac | 600 |
| agcgaccaca tgaccttctt gcagcgggtg aagaacatgc tgattgcttt tagccagaac | 660 |

```
tttctgtgtg acgtggtgta cagcccctac gctaccctgg ctagcgaatt tctgcagcgg    720
gaagtgaccg tgcaggacct gctgagcagc gctagcgtgt ggctgtttcg gagcgacttt    780
gtgaaggact accccggcc cattatgccc aacatggtgt tgtgggcgg cattaactgt      840 ctgcaccaga accccctgag ccaggaattt gaagcttaca ttaacgctag cggcgaacac    900
ggcattgtgg tgtttagcct gggcagcatg gtgagcgaaa ttcccgaaaa aaggctatg    960 gctattgctg acgctctggg caagattccc cagaccgtgc tgtggcggta caccggcacc   1020
cggcccagca acctggctaa caacaccatt ctggtgaagt ggctgcccca aacgacctg    1080 ctgggccacc ccatgacccg ggcttttatt acccacgctg cagccacgg cgtgtacgaa    1140 agcatttgta acggcgtgcc catggtgatg atgcccctgt tggcgacca atggacaac     1200 gctaagcgga tggaaaccaa gggcgctggc gtgaccctga acgtgctgga atgaccagc    1260 gaagacctgg aaaacgctct gaaggctgtg attaacgaca agagctacaa ggaaaacatt   1320
atgcggctga gcagcctgca aaggaccgg cccgtggaac ccctggacct ggctgtgttt    1380
tgggtggaat ttgtgatgcg gcacaagggc gctcccacc tgcggcccgc tgctcacgac    1440
ctgacctggt accagtacca cagcctggac gtgattggct ttctgctggc tgtggtgctg    1500
accgtggctt ttattacctt taagtgttgt gcttacggct accggaagtg tctgggcaag    1560
aagggccggg tgaagaaggc tcacaagagc aagacccac                         1599

<210> SEQ ID NO 3
<211> LENGTH: 1599
<212> TYPE: DNA
<213> ORGANISM: Artificial Sequence
<220> FEATURE:
<223> OTHER INFORMATION: Engineered UGT1A1 sequence U201DP

<400> SEQUENCE: 3
atggccgtgg agagccaggg aggacggcct ctggtgctgg actgctgct gtgcgtgctg       60 ggacctgtgg tgagccacgc cggaaagatc ctgctgatcc ctgtggacgg aagccactgg    120
ctgagcatgc tgggagccat ccagcagctg cagcagcggg gacacgagat cgtggtgctg    180
gcccctgacg ccagcctgta catccgggac ggagccttct acaccctgaa gacctaccct    240
gtgcctttcc agcgggagga cgtgaaggag agcttcgtga gcctgggaca gacgtgttc    300 gagaacgaca gcttcctgca gcgggtgatc aagacctaca agaagatcaa gaaggacagc    360
gccatgctgc tgagcggctg cagccacctg ctgcacaaca aggagctgat ggccagcctg    420
gccgagagca gcttcgacgt gatgctgacc gacccttttc cgccttgcag ccctatcgtg    480
gcccagtacc tgagcctgcc taccgtgttc ttcctgcacg ccctgccttg cagcctggag    540
ttcgaggcca cccagtgccc taaccctttc agctacgtgc tcggcctct gagcagccac    600 agcgaccaca tgaccttcct gcagcgggtg aagaacatgc tgatcgcctt cagccagaac    660
ttcctgtgcg acgtggtgta cagcccttac gccaccctgg ccagcgagtt cctgcagcgg    720
gaggtgaccg tgcaggacct gctgagcagc gccagcgtgt ggctgttccg gagcgacttc    780
gtgaaggact accctcggcc tatcatgcct aacatggtgt tcgtgggagg aatcaactgc    840
ctgcaccaga ccctctgag ccaggagttc gaggcctaca tcaacgccag cggagagcac    900
ggaatcgtgg tgttcagcct gggaagcatg gtgagcgaga tccctgagaa aaggccatg    960 gccatcgccg acgccctggg aaagatccct cagaccgtgc tgtggcggta caccggaacc   1020
cggcctagca acctggccaa caacaccatc ctggtgaagt ggctgcctca aacgacctg    1080
```

| | |
|---|---|
| ctgggacacc ctatgacccg ggccttcatc acccacgccg gaagccacgg agtgtacgag | 1140 |
| agcatctgca acggagtgcc tatggtgatg atgcctctgt tcggagacca gatggacaac | 1200 |
| gccaagcgga tggagaccaa gggagccgga gtgaccctga acgtgctgga gatgaccagc | 1260 |
| gaggacctgg agaacgccct gaaggccgtg atcaacgaca gagctacaa ggagaacatc | 1320 |
| atgcggctga gcagcctgca aggaccgg cctgtggagc tctggacct ggccgtgttc | 1380 |
| tgggtggagt tcgtgatgcg gcacaaggga ccccctcacc tgcggcctgc cgcccacgac | 1440 |
| ctgacctggt accagtacca cagcctggac gtgatcggat tcctgctggc cgtggtgctg | 1500 |
| accgtggcct tcatcacctt caagtgctgc gcctacggat accggaagtg cctgggaaag | 1560 |
| aagggacggg tgaagaaggc ccacaagagc aagacccac | 1599 |

<210> SEQ ID NO 4
<211> LENGTH: 1599
<212> TYPE: DNA
<213> ORGANISM: Artificial Sequence
<220> FEATURE:
<223> OTHER INFORMATION: Engineered UGT1A1 sequence

<400> SEQUENCE: 4

| | |
|---|---|
| atggccgtgg aatctcaggg cggcagacct ctggtgctgg gcctgctgct gtgtgtgctg | 60 |
| ggacctgtgg tgtctcacgc cggcaagatc ctgctgatcc cgtggacgg cagccactgg | 120 |
| ctgtctatgc tgggcgccat tcagcagctg cagcagaggg gccacgagat cgtggtgctg | 180 |
| gcccctgacg ccagcctgta catcagagat ggcgccttct acaccctgaa aacctacccc | 240 |
| gtgcccttcc agcgcgagga cgtgaaagaa agcttcgtgt ccctgggcca caacgtgttc | 300 |
| gagaacgaca gcttcctgca gagagtgatc aagacctaca gaagatcaa gaaagacagc | 360 |
| gccatgctgc tgagcggctg ctcccatctg ctgcacaaca agaactgat ggcctccctg | 420 |
| gccgagagca gcttcgacgt gatgctgacc gacccattcc tgccctgcag ccctatcgtg | 480 |
| gcccagtacc tgagcctgcc taccgtgttc ttcctgcacg ccctgccttg ctccctggaa | 540 |
| ttcgaggcca cccagtgccc caaccccttc agctacgtgc ccagaccact gagcagccac | 600 |
| agcgaccaca tgacctttct gcagcgcgtg aagaacatgc tgatcgcctt cagccagaac | 660 |
| ttcctgtgcg acgtggtgta cagcccctac gctaccctgg ccagcgaatt cctgcagcgg | 720 |
| gaagtgaccg tgcaggacct gctgtctagc gccagcgtgt ggctgttccg cagcgacttc | 780 |
| gtgaaggact accccagacc catcatgccc aacatggtgt tcgtgggcgg catcaactgc | 840 |
| ctgcaccaga ccccctgag ccaggaattt gaggcctaca tcaacgccag cggcgagcac | 900 |
| ggcatcgtgg tgtttagcct gggcagcatg gtgtccgaga tccccgagaa aaaggccatg | 960 |
| gctatcgccg acgccctggg aaagatcccc cagacagtgc tgtggcgta caccggcacc | 1020 |
| agacccagca acctggccaa caacaccatc ctcgtgaaat ggctgcccca aacgacctg | 1080 |
| ctgggccacc ctatgacccg gcctttatc acacacgccg gctcccacgg cgtgtacgag | 1140 |
| agcatctgca acggcgtgcc catggtcatg atgccctgt cggcgacca gatggacaac | 1200 |
| gccaagcgga tggaaacaaa gggcgctggc gtgaccctga acgtgctgga aatgaccagc | 1260 |
| gaggacctgg aaaacgccct gaaggccgtg atcaacgaca gagctacaa agaaaacatc | 1320 |
| atgcggctgt ccagcctgca aggacagga cccgtggaac ccctggacct ggccgtgttc | 1380 |
| tgggtggaat tcgtgatgcg gcacaagggc gctccccatc tgaggcctgc agctcacgac | 1440 |
| ctgacctggt atcagtacca cagcctggac gtgatcggct tcctgctggc agtggtgctg | 1500 |
| accgtggcct tcatcacctt caagtgctgc gcctacggct accggaagtg cctgggcaag | 1560 |

```
aaaggcagag tgaagaaggc ccacaagagc aagacccac                        1599
```

<210> SEQ ID NO 5
<211> LENGTH: 1602
<212> TYPE: DNA
<213> ORGANISM: Homo sapiens
<220> FEATURE:
<221> NAME/KEY: CDS
<222> LOCATION: (1)..(1602)

<400> SEQUENCE: 5

```
atg gct gtg gag tcc cag ggc gga cgc cca ctt gtc ctg ggc ctg ctg    48
Met Ala Val Glu Ser Gln Gly Gly Arg Pro Leu Val Leu Gly Leu Leu
1               5                   10                  15 ctg tgt gtg ctg ggc cca gtg gtg tcc cat gct ggg aag ata ctg ttg    96
Leu Cys Val Leu Gly Pro Val Val Ser His Ala Gly Lys Ile Leu Leu
                20                  25                  30 atc cca gtg gat ggc agc cac tgg ctg agc atg ctt ggg gcc atc cag   144
Ile Pro Val Asp Gly Ser His Trp Leu Ser Met Leu Gly Ala Ile Gln
            35                  40                  45 cag ctg cag cag agg gga cat gaa ata gtt gtc cta gca cct gac gcc   192
Gln Leu Gln Gln Arg Gly His Glu Ile Val Val Leu Ala Pro Asp Ala
        50                  55                  60 tcg ttg tac atc aga gac gga gca ttt tac acc ttg aag acg tac cct   240
Ser Leu Tyr Ile Arg Asp Gly Ala Phe Tyr Thr Leu Lys Thr Tyr Pro
65                  70                  75                  80 gtg cca ttc caa agg gag gat gtg aaa gag tct ttt gtt agt ctc ggg   288
Val Pro Phe Gln Arg Glu Asp Val Lys Glu Ser Phe Val Ser Leu Gly
                85                  90                  95 cat aat gtt ttt gag aat gat tct ttc ctg cag cgt gtg atc aaa aca   336
His Asn Val Phe Glu Asn Asp Ser Phe Leu Gln Arg Val Ile Lys Thr
                100                 105                 110 tac aag aaa ata aaa aag gac tct gct atg ctt ttg tct ggc tgt tcc   384
Tyr Lys Lys Ile Lys Lys Asp Ser Ala Met Leu Leu Ser Gly Cys Ser
            115                 120                 125 cac tta ctg cac aac aag gag ctc atg gcc tcc ctg gca gaa agc agc   432
His Leu Leu His Asn Lys Glu Leu Met Ala Ser Leu Ala Glu Ser Ser
        130                 135                 140 ttt gat gtc atg ctg acg gac cct ttc ctt cct tgc agc ccc atc gtg   480
Phe Asp Val Met Leu Thr Asp Pro Phe Leu Pro Cys Ser Pro Ile Val
145                 150                 155                 160 gcc cag tac ctg tct ctg ccc act gta ttc ttc ttg cat gca ctg cca   528
Ala Gln Tyr Leu Ser Leu Pro Thr Val Phe Phe Leu His Ala Leu Pro
                165                 170                 175 tgc agc ctg gaa ttt gag gct acc cag tgc ccc aac cca ttc tcc tac   576
Cys Ser Leu Glu Phe Glu Ala Thr Gln Cys Pro Asn Pro Phe Ser Tyr
                180                 185                 190 gtg ccc agg cct ctc tcc tct cat tca gat cac atg acc ttc ctg cag   624
Val Pro Arg Pro Leu Ser Ser His Ser Asp His Met Thr Phe Leu Gln
            195                 200                 205 cgg gtg aag aac atg ctc att gcc ttt tca cag aac ttt ctg tgc gac   672
Arg Val Lys Asn Met Leu Ile Ala Phe Ser Gln Asn Phe Leu Cys Asp
        210                 215                 220 gtg gtt tat tcc ccg tat gca acc ctt gcc tca gaa ttc ctt cag aga   720
Val Val Tyr Ser Pro Tyr Ala Thr Leu Ala Ser Glu Phe Leu Gln Arg
225                 230                 235                 240 gag gtg act gtc cag gac cta ttg agc tct gca tct gtc tgg ctg ttt   768
Glu Val Thr Val Gln Asp Leu Leu Ser Ser Ala Ser Val Trp Leu Phe
                245                 250                 255 aga agt gac ttt gtg aag gat tac cct agg ccc atc atg ccc aat atg   816
Arg Ser Asp Phe Val Lys Asp Tyr Pro Arg Pro Ile Met Pro Asn Met
```

```
          Arg Ser Asp Phe Val Lys Asp Tyr Pro Arg Pro Ile Met Pro Asn Met
                      260                 265                 270 gtt ttt gtt ggt gga atc aac tgc ctt cac caa aat cca cta tcc cag         864
Val Phe Val Gly Gly Ile Asn Cys Leu His Gln Asn Pro Leu Ser Gln
            275                 280                 285 gaa ttt gaa gcc tac att aat gct tct gga gaa cat gga att gtg gtt         912
Glu Phe Glu Ala Tyr Ile Asn Ala Ser Gly Glu His Gly Ile Val Val
        290                 295                 300 ttc tct ttg gga tca atg gtc tca gaa att cca gag aag aaa gct atg         960
Phe Ser Leu Gly Ser Met Val Ser Glu Ile Pro Glu Lys Lys Ala Met
305                 310                 315                 320 gca att gct gat gct ttg ggc aaa atc cct cag aca gtc ctg tgg cgg        1008
Ala Ile Ala Asp Ala Leu Gly Lys Ile Pro Gln Thr Val Leu Trp Arg
                325                 330                 335 tac act gga acc cga cca tcg aat ctt gcg aac aac acg ata ctt gtt        1056
Tyr Thr Gly Thr Arg Pro Ser Asn Leu Ala Asn Asn Thr Ile Leu Val
            340                 345                 350 aag tgg cta ccc caa aac gat ctg ctt ggt cac ccg atg acc cgt gcc        1104
Lys Trp Leu Pro Gln Asn Asp Leu Leu Gly His Pro Met Thr Arg Ala
        355                 360                 365 ttt atc acc cat gct ggt tcc cat ggt gtt tat gaa agc ata tgc aat        1152
Phe Ile Thr His Ala Gly Ser His Gly Val Tyr Glu Ser Ile Cys Asn
370                 375                 380 ggc gtt ccc atg gtg atg atg ccc ttg ttt ggt gat cag atg gac aat        1200
Gly Val Pro Met Val Met Met Pro Leu Phe Gly Asp Gln Met Asp Asn
385                 390                 395                 400 gca aag cgc atg gag act aag gga gct gga gtg acc ctg aat gtt ctg        1248
Ala Lys Arg Met Glu Thr Lys Gly Ala Gly Val Thr Leu Asn Val Leu
                405                 410                 415 gaa atg act tct gaa gat tta gaa aat gct cta aaa gca gtc atc aat        1296
Glu Met Thr Ser Glu Asp Leu Glu Asn Ala Leu Lys Ala Val Ile Asn
            420                 425                 430 gac aaa agt tac aag gag aac atc atg cgc ctc tcc agc ctt cac aag        1344
Asp Lys Ser Tyr Lys Glu Asn Ile Met Arg Leu Ser Ser Leu His Lys
        435                 440                 445 gac cgc ccg gtg gag ccg ctg gac ctg gcc gtg ttc tgg gtg gag ttt        1392
Asp Arg Pro Val Glu Pro Leu Asp Leu Ala Val Phe Trp Val Glu Phe
450                 455                 460 gtg atg agg cac aag ggc gcg cca cac ctg cgc ccc gca gcc cac gac        1440
Val Met Arg His Lys Gly Ala Pro His Leu Arg Pro Ala Ala His Asp
465                 470                 475                 480 ctc acc tgg tac cag tac cat tcc ttg gac gtg att ggt ttc ctc ttg        1488
Leu Thr Trp Tyr Gln Tyr His Ser Leu Asp Val Ile Gly Phe Leu Leu
                485                 490                 495 gcc gtc gtg ctg aca gtg gcc ttc atc acc ttt aaa tgt tgt gct tat        1536
Ala Val Val Leu Thr Val Ala Phe Ile Thr Phe Lys Cys Cys Ala Tyr
            500                 505                 510 ggc tac cgg aaa tgc ttg ggg aaa aaa ggg cga gtt aag aaa gcc cac        1584
Gly Tyr Arg Lys Cys Leu Gly Lys Lys Gly Arg Val Lys Lys Ala His
        515                 520                 525 aaa tcc aag acc cat tga                                                 1602
Lys Ser Lys Thr His
    530

<210> SEQ ID NO 6
<211> LENGTH: 533
<212> TYPE: PRT
<213> ORGANISM: Homo sapiens

<400> SEQUENCE: 6
```

```
Met Ala Val Glu Ser Gln Gly Gly Arg Pro Leu Val Leu Gly Leu Leu
 1               5                  10                  15

Leu Cys Val Leu Gly Pro Val Val Ser His Ala Gly Lys Ile Leu Leu
             20                  25                  30

Ile Pro Val Asp Gly Ser His Trp Leu Ser Met Leu Gly Ala Ile Gln
             35                  40                  45

Gln Leu Gln Gln Arg Gly His Glu Ile Val Val Leu Ala Pro Asp Ala
     50                  55                  60

Ser Leu Tyr Ile Arg Asp Gly Ala Phe Tyr Thr Leu Lys Thr Tyr Pro
65                  70                  75                  80

Val Pro Phe Gln Arg Glu Asp Val Lys Glu Ser Phe Val Ser Leu Gly
             85                  90                  95

His Asn Val Phe Glu Asn Asp Ser Phe Leu Gln Arg Val Ile Lys Thr
             100                 105                 110

Tyr Lys Lys Ile Lys Lys Asp Ser Ala Met Leu Leu Ser Gly Cys Ser
             115                 120                 125

His Leu Leu His Asn Lys Glu Leu Met Ala Ser Leu Ala Glu Ser Ser
     130                 135                 140

Phe Asp Val Met Leu Thr Asp Pro Phe Leu Pro Cys Ser Pro Ile Val
145                 150                 155                 160

Ala Gln Tyr Leu Ser Leu Pro Thr Val Phe Phe Leu His Ala Leu Pro
             165                 170                 175

Cys Ser Leu Glu Phe Glu Ala Thr Gln Cys Pro Asn Pro Phe Ser Tyr
             180                 185                 190

Val Pro Arg Pro Leu Ser Ser His Ser Asp His Met Thr Phe Leu Gln
             195                 200                 205

Arg Val Lys Asn Met Leu Ile Ala Phe Ser Gln Asn Phe Leu Cys Asp
     210                 215                 220

Val Val Tyr Ser Pro Tyr Ala Thr Leu Ala Ser Glu Phe Leu Gln Arg
225                 230                 235                 240

Glu Val Thr Val Gln Asp Leu Leu Ser Ser Ala Ser Val Trp Leu Phe
             245                 250                 255

Arg Ser Asp Phe Val Lys Asp Tyr Pro Arg Pro Ile Met Pro Asn Met
             260                 265                 270

Val Phe Val Gly Gly Ile Asn Cys Leu His Gln Asn Pro Leu Ser Gln
             275                 280                 285

Glu Phe Glu Ala Tyr Ile Asn Ala Ser Gly Glu His Gly Ile Val Val
             290                 295                 300

Phe Ser Leu Gly Ser Met Val Ser Glu Ile Pro Glu Lys Lys Ala Met
305                 310                 315                 320

Ala Ile Ala Asp Ala Leu Gly Lys Ile Pro Gln Thr Val Leu Trp Arg
             325                 330                 335

Tyr Thr Gly Thr Arg Pro Ser Asn Leu Ala Asn Asn Thr Ile Leu Val
             340                 345                 350

Lys Trp Leu Pro Gln Asn Asp Leu Leu Gly His Pro Met Thr Arg Ala
             355                 360                 365

Phe Ile Thr His Ala Gly Ser His Gly Val Tyr Glu Ser Ile Cys Asn
     370                 375                 380

Gly Val Pro Met Val Met Met Pro Leu Phe Gly Asp Gln Met Asp Asn
385                 390                 395                 400

Ala Lys Arg Met Glu Thr Lys Gly Ala Gly Val Thr Leu Asn Val Leu
             405                 410                 415

Glu Met Thr Ser Glu Asp Leu Glu Asn Ala Leu Lys Ala Val Ile Asn
```

```
                420             425             430
Asp Lys Ser Tyr Lys Glu Asn Ile Met Arg Leu Ser Ser Leu His Lys
            435                 440                 445

Asp Arg Pro Val Glu Pro Leu Asp Leu Ala Val Phe Trp Val Glu Phe
        450                 455                 460

Val Met Arg His Lys Gly Ala Pro His Leu Arg Pro Ala Ala His Asp
465                 470                 475                 480

Leu Thr Trp Tyr Gln Tyr His Ser Leu Asp Val Ile Gly Phe Leu Leu
                485                 490                 495

Ala Val Val Leu Thr Val Ala Phe Ile Thr Phe Lys Cys Cys Ala Tyr
            500                 505                 510

Gly Tyr Arg Lys Cys Leu Gly Lys Lys Gly Arg Val Lys Lys Ala His
        515                 520                 525

Lys Ser Lys Thr His
    530

<210> SEQ ID NO 7
<211> LENGTH: 1602
<212> TYPE: DNA
<213> ORGANISM: Artificial Sequence
<220> FEATURE:
<223> OTHER INFORMATION: optimized UGT1A1 v2.1

<400> SEQUENCE: 7
atggctgtgg aatcacaagg aggtagacca ctggttctcg acttttgct  ttgcgtgctg      60 gggcccgtgg tgtcgcatgc cggaaagatc ctgctgatcc cggtggatgg atcacactgg     120
ctgtccatgc tgggtgccat ccaacagctc cagcagcggg ccacgaaat  tgtggtcctg     180 gccccggacg cttccctgta tattcgggac ggagcgttct acactctcaa gacctaccct     240
gtccccttcc aaagggagga cgtgaaggaa agctttgtgt cgctggggca taatgtgttc     300
gagaacgaca gcttcctcca aagggttatt aaaacctaca agaagatcaa aaaggattcg     360
gccatgctcc tttccggatg ttcacacctg ttgcataaca aggaattgat ggccagcctg     420
gcagaatcca gctttgacgt catgcttact gacccgttct tgccttgctc ccgattgtg      480 gcccaatacc tgtcgctccc aaccgtgttc ttcctgcacg ccttgccttg ttcgctggaa     540
ttcgaagcga ctcagtgtcc caatccgttc tcctacgtcc cgcgccccgct ttcaagccat     600 tcggatcaca tgactttcct ccagcgcgtc aagaacatgc tcattgcgtt cagccagaac     660
tttctgtgcg acgtggttta ctcaccttac gctaccttgg cttctgagtt cctgcagaga     720
gaagtgactg tgcaagatct gctgtcctca gcgtccgttt ggttgttccg gtctgacttc     780
gtcaaggact acccgcgccc gatcatgccg aatatggtct tgtgggcgg  tatcaactgc     840 ctgcatcaaa acccactgag ccaggagttt gaggcgtaca tcaacgcctc gggagagcat     900
ggaatcgtgg tgttctccct cggttccatg gtgtccgaga tcccggaaaa gaaggcaatg     960
gccatcgcag atgccctggg caaaatcccg cagaccgtgc tctggcgcta cacgggtact    1020
cggcctagca atttggcaaa caacaccatc ctggtgaaat ggctgccgca gaacgacctc    1080
ctgggccacc caatgactcg cgctttcatt acccatgcgg gctcgcacgg agtctacgaa    1140
tccatctgca atggagtccc gatggtgatg atgccacttt tcggagatca gatggataat    1200
gcaaaaagaa tggaaaccaa gggggccgga gtgacgctga acgtgcttga aatgaccctg    1260
gaagatctgg agaacgctct caaagcggtg atcaacgaca gtcctacaa  ggaaaacatc    1320 atgcgcctga gctccctcca aaggaccga ccagtggaac cgctggacct cgcggtcttt    1380
```

| tgggtggagt tcgtgatgag gcacaagggc gccccccacc tcagacccgc agctcatgac | 1440 |
| ctcacttggt accagtacca ttcgctggat gtcatcggct ttctcctggc ggtcgtgctc | 1500 |
| accgtggcgt tcatcacctt caagtgctgc gcctacggat atcgcaaatg cttggggaag | 1560 |
| aaaggacggg tgaagaaggc acacaagtca agacgcact ga | 1602 |

<210> SEQ ID NO 8
<211> LENGTH: 1602
<212> TYPE: DNA
<213> ORGANISM: Artificial Sequence
<220> FEATURE:
<223> OTHER INFORMATION: optimized UGT1A1 v3

<400> SEQUENCE: 8

| atggccgtgg aatctcaggg cggcagacct ctggtgctgg gcctgctgct gtgtgtgctg | 60 |
| ggacctgtgg tgtctcacgc cggcaagatc ctgctgatcc ccgtggatgg cagccactgg | 120 |
| ctgtctatgc tgggcgccat tcagcagctg cagcagaggg gccacgagat cgtggtgctg | 180 |
| gcccctgatg ccagcctgta catcagagat ggcgccttct acaccctgaa aacctacccc | 240 |
| gtgcccttcc agcgcgagga cgtgaaagaa agcttcgtgt ccctgggcca caacgtgttc | 300 |
| gagaacgaca gcttcctgca gagagtgatc aagacctaca gaagatcaa gaagacagc | 360 |
| gccatgctgc tgagcggctg ctcccatctg ctgcacaaca agaactgat ggcctccctg | 420 |
| gccgagagca gcttcgacgt gatgctgacc gacccattcc tgccctgcag ccctatcgtg | 480 |
| gcccagtacc tgagcctgcc taccgtgttc ttcctgcacg ccctgccttg ctccctggaa | 540 |
| ttcgaggcca cccagtgccc caaccccttc agctacgtgc ccagaccact gagcagccac | 600 |
| agcgaccaca tgaccttcct gcagcgcgtg aagaacatgc tgatcgcctt cagccagaac | 660 |
| ttcctgtgcg acgtggtgta cagcccctac gctaccctgg ccagcgaatt cctgcagcgg | 720 |
| gaagtgaccg tgcaggacct gctgtctagc gccagcgtgt ggctgttccg cagcgacttc | 780 |
| gtgaaggact accccagacc catcatgccc aacatggtgt tcgtgggcgg catcaactgc | 840 |
| ctgcaccaga cccctgag ccaggaattt gaggcctaca tcaacgccag cggcgagcac | 900 |
| ggcatcgtgg tgtttagcct gggcagcatg gtgtccgaga tccccgagaa aaaggccatg | 960 |
| gctatcgccg acgccctggg aaagatcccc cagacagtgc tgtggcggta caccggcacc | 1020 |
| agacccagca acctggccaa caacaccatc ctcgtgaaat ggctgcccca gaacgacctg | 1080 |
| ctgggccacc ctatgacccg gcctttatc acacacgccg gctcccatgg cgtgtacgag | 1140 |
| agcatctgca cggcgtgcc catggtcatg atgcccctgt ccgcgacca gatggacaac | 1200 |
| gccaagcgga tggaaacaaa gggcgctggc gtgaccctga acgtgctgga aatgaccagc | 1260 |
| gaggacctgg aaaacgccct gaaggccgtg atcaacgaca gagctacaa agaaaacatc | 1320 |
| atgcggctgt ccagcctgca aaggacaga cccgtggaac ccctggacct ggccgtgttc | 1380 |
| tgggtggaat cgtgatgcg gcacaagggc gctccccatc tgaggcctgc agctcacgac | 1440 |
| ctgacctggt atcagtacca cagcctggac gtgatcggct tcctgctggc agtggtgctg | 1500 |
| accgtggcct tcatcacctt caagtgctgc gcctacggct accggaagtg cctgggcaag | 1560 |
| aaaggcagag tgaagaaggc ccacaagagc aagacccact ga | 1602 |

<210> SEQ ID NO 9
<211> LENGTH: 6498
<212> TYPE: DNA
<213> ORGANISM: Artificial Sequence
<220> FEATURE:
<223> OTHER INFORMATION: pAAV.TBG.hUGT1A1co.WRPE.BGH (p3793) vector

```
<220> FEATURE:
<221> NAME/KEY: repeat_region
<222> LOCATION: (1)..(168)
<223> OTHER INFORMATION: 5' ITR
<220> FEATURE:
<221> NAME/KEY: enhancer
<222> LOCATION: (211)..(310)
<223> OTHER INFORMATION: alpha mic/bik
<220> FEATURE:
<221> NAME/KEY: enhancer
<222> LOCATION: (317)..(416)
<223> OTHER INFORMATION: alpha mic/bik
<220> FEATURE:
<221> NAME/KEY: promoter
<222> LOCATION: (431)..(907)
<223> OTHER INFORMATION: TBG promoter
<220> FEATURE:
<221> NAME/KEY: Intron
<222> LOCATION: (939)..(1071)
<223> OTHER INFORMATION: SV40 misc intron (Promega)
<220> FEATURE:
<221> NAME/KEY: misc_feature
<222> LOCATION: (1086)..(1091)
<223> OTHER INFORMATION: Kozak
<220> FEATURE:
<221> NAME/KEY: misc_feature
<222> LOCATION: (1092)..(2690)
<223> OTHER INFORMATION: UGT1A1 CDS
<220> FEATURE:
<221> NAME/KEY: misc_feature
<222> LOCATION: (2709)..(3250)
<220> FEATURE:
<221> NAME/KEY: polyA_signal
<222> LOCATION: (3257)..(3471)
<223> OTHER INFORMATION: BGH polyA
<220> FEATURE:
<221> NAME/KEY: repeat_region
<222> LOCATION: (3521)..(3558)
<223> OTHER INFORMATION: 3' ITR
<220> FEATURE:
<221> NAME/KEY: misc_feature
<222> LOCATION: (4451)..(5308)
<223> OTHER INFORMATION: Amp-R CDS
<220> FEATURE:
<221> NAME/KEY: misc_feature
<222> LOCATION: (5482)..(6070)
<223> OTHER INFORMATION: origin

<400> SEQUENCE: 9
ctgcgcgctc gctcgctcac tgaggccgcc cgggcaaagc ccgggcgtcg ggcgaccttt     60
ggtcgcccgg cctcagtgag cgagcgagcg cgcagagagg gagtgccaa ctccatcact    120 agggggttcct tgtagttaat gattaacccg ccatgctact tatctacgta gccatgctct   180
aggaagatcg gaattcgccc ttaagctagc aggttaattt ttaaaaagca gtcaaaagtc    240
caagtggccc ttggcagcat ttactctctc tgtttgctct ggttaataat ctcaggagca    300
caaacattcc agatccaggt taattttaa aaagcagtca aaagtccaag tggcccttgg    360
cagcatttac tctctctgtt tgctctggtt aataatctca ggagcacaaa cattccagat    420
ccggcgcgcc agggctggaa gctacctttg acatcatttc ctctgcgaat gcatgtataa    480
tttctacaga acctattaga aaggatcacc cagcctctgc ttttgtacaa ctttccctta    540
aaaaactgcc aattccactg ctgtttggcc caatagtgag aactttttcc tgctgcctct    600
tggtgctttt gcctatggcc cctattctgc ctgctgaaga cactcttgcc agcatggact    660 taaaccccctc cagctctgac aatcctcttt ctcttttgtt ttacatgaag ggtctggcag    720
ccaaagcaat cactcaaagt tcaaaccctta tcattttttg ctttgttcct cttggccttg    780
gttttgtaca tcagctttga aaataccatc ccagggttaa tgctgggggtt aatttataac    840 taagagtgct ctagttttgc aatacaggac atgctataaa aatggaaaga tgttgctttc    900
```

```
tgagagactg cagaagttgg tcgtgaggca ctgggcaggt aagtatcaag gttacaagac    960
aggtttaagg agaccaatag aaactgggct tgtcgagaca gagaagactc ttgcgtttct   1020
gataggcacc tattggtctt actgacatcc actttgcctt tctctccaca ggtgtccagg   1080
cggccgccac catggccgtg aatctcagg gcggcagacc tctggtgctg ggcctgctgc    1140
tgtgtgtgct gggacctgtg gtgtctcacg ccggcaagat cctgctgatc cccgtggacg   1200
gcagccactg gctgtctatg ctgggcgcca ttcagcagct gcagcagagg ggccacgaga   1260
tcgtggtgct ggcccctgac gccagcctgt acatcagaga tggcgccttc tacaccctga   1320
aaacctaccc cgtgcccttc cagcgcgagg acgtgaaaga agcttcgtg tccctgggcc    1380
acaacgtgtt cgagaacgac agcttcctgc agagagtgat caagacctac aagaagatca   1440
agaaagacag cgccatgctg ctgagcggct gctcccatct gctgcacaac aaagaactga   1500
tggcctccct ggccgagagc agcttcgacg tgatgctgac cgacccattc ctgccctgca   1560
gccctatcgt ggcccagtac ctgagcctgc ctaccgtgtt cttcctgcac gccctgcctt   1620
gctccctgga attcgaggcc acccagtgcc ccaaccccct cagctacgtg cccagaccac   1680
tgagcagcca cagcgaccac atgaccttc tgcagcgcgt gaagaacatg ctgatcgcct    1740
tcagccagaa cttcctgtgc gacgtggtgt acagcccta cgctaccctg ccagcgaat    1800
tcctgcagcg ggaagtgacc gtgcaggacc tgctgtctag cgccagcgtg tggctgttcc   1860
gcagcgactt cgtgaaggac taccccagac ccatcatgcc caacatggtg ttcgtgggcg   1920
gcatcaactg cctgcaccag aaccccctga gccaggaatt tgaggcctac atcaacgcca   1980
gcggcgagca cggcatcgtg gtgtttagcc tgggcagcat ggtgtccgag atccccgaga   2040
aaaaggccat ggctatcgcc gacgccctgg gaaagatccc ccagacagtg ctgtggcggt   2100
acaccggcac cagacccagc aacctggcca acaacaccat cctcgtgaaa tggctgcccc   2160
agaacgacct gctgggccac cctatgaccc gggcctttat cacacacgcc ggctcccacg   2220
gcgtgtacga gagcatctgc aacggcgtgc ccatggtcat gatgccctg ttcggcgacc    2280
agatggacaa cgccaagcgg atggaaacaa agggcgctgg cgtgacctg aacgtgctgg    2340
aaatgaccag cgaggacctg aaaacgccc tgaaggccgt gatcaacgac aagagctaca    2400
agaaaacat catgcggctg tccagcctgc acaaggacag acccgtggaa cccctggacc    2460
tggccgtgtt ctgggtggaa ttcgtgatgc ggcacaaggg cgctccccat ctgaggcctg   2520
cagctcacga cctgacctgg tatcagtacc acagcctgga cgtgatcggc ttcctgctgg   2580
cagtggtgct gaccgtggcc ttcatcacct tcaagtgctg cgcctacggc taccggaagt   2640
gcctgggcaa gaaaggcaga gtgaagaagg cccacaagag caagacccac tgataagcat   2700
gcggatccaa tcaacctctg gattacaaaa tttgtgaaag attgactggt attcttaact   2760
atgttgctcc ttttacgcta tgtggatacg ctgctttaat gcctttgtat catgctattg   2820
cttcccgtat ggctttcatt ttctcctcct tgtataaatc ctggttgctg tctctttatg   2880
aggagttgtg gcccgttgtc aggcaacgtg gcgtggtgtg cactgtgttt gctgacgcaa   2940
cccccactgg ttggggcatt gccaccacct gtcagctcct ttccgggact ttcgctttcc   3000
ccctccctat tgccacggcg gaactcatcg ccgcctgcct tgcccgctgc tggacagggg   3060
ctcggctgtt gggcactgac aattccgtgg tgttgtcggg gaagctgacg tccttccat   3120
ggctgctcgc ctgtgttgcc acctggattc tgcgcgggac gtccttctgc tacgtccctt   3180
cggccctcaa tccagcggac cttccttccc gcggcctgct gccggctctg cggcctcttc   3240
```

```
cgcgtcttcg agatctgcct cgactgtgcc ttctagttgc cagccatctg ttgtttgccc    3300
ctcccccgtg ccttccttga ccctggaagg tgccactccc actgtccttt cctaataaaa    3360
tgaggaaatt gcatcgcatt gtctgagtag gtgtcattct attctggggg gtgggtggg     3420
gcaggacagc aaggggggagg attgggaaga caatagcagg catgctgggg actcgagtta   3480
agggcgaatt cccgattagg atcttcctag agcatggcta cgtagataag tagcatggcg    3540
ggttaatcat taactacaag gaaccccctag tgatggagtt ggccactccc tctctgcgcg   3600
ctcgctcgct cactgaggcc gggcgaccaa aggtcgcccg acgcccgggc tttgcccggg    3660
cggcctcagt gagcgagcga gcgcgcagcc ttaattaacc taattcactg gccgtcgttt    3720
tacaacgtcg tgactgggaa aaccctggcg ttacccaact taatcgcctt gcagcacatc    3780
ccccttttcgc cagctggcgt aatagcgaag aggcccgcac cgatcgccct tcccaacagt   3840
tgcgcagcct gaatggcgaa tgggacgcgc cctgtagcgg cgcattaagc gcggcgggtg    3900
tggtggttac gcgcagcgtg accgctacac ttgccagcgc cctagcgccc gctcctttcg    3960
ctttcttccc ttcctttctc gccacgttcg ccggcttttcc ccgtcaagct ctaaatcggg   4020
ggctcccttt agggttccga tttagtgctt tacggcacct cgaccccaaa aaacttgatt    4080
agggtgatgg ttcacgtagt gggccatcgc cctgatagac ggttttttcgc cctttgacgt   4140
tggagtccac gttctttaat agtggactct tgttccaaac tggaacaaca ctcaaccctca   4200
tctcggtcta ttcttttgat ttataaggga ttttgccgat ttcggcctat tggttaaaaa    4260
atgagctgat ttaacaaaaa tttaacgcga attttaacaa aatattaacg cttacaattt    4320
aggtggcact tttcggggaa atgtgcgcgg aaccccctatt tgtttatttt tctaaataca    4380
ttcaaatatg tatccgctca tgagacaata accctgataa atgcttcaat aatattgaaa    4440
aaggaagagt atgagtattc aacatttccg tgtcgccctt attcccctttt ttgcggcatt    4500
ttgccttcct gttttttgctc acccagaaac gctggtgaaa gtaaaagatg ctgaagatca    4560
gttgggtgca cgagtgggtt acatcgaact ggatctcaac agcggtaaga tccttgagag    4620
ttttcgcccc gaagaacgtt ttccaatgat gagcactttt aaagttctgc tatgtggcgc     4680
ggtattatcc cgtattgacg ccgggcaaga gcaactcggt cgccgcatac actattctca    4740
gaatgacttg gttgagtact caccagtcac agaaaagcat cttacggatg gcatgacagt    4800
aagagaatta tgcagtgctg ccataaccat gagtgataac actgcggcca acttacttct    4860
gacaacgatc ggaggaccga aggagctaac cgcttttttg cacaacatgg gggatcatgt    4920
aactcgcctt gatcgttggg aaccggagct gaatgaagcc ataccaaacg acgagcgtga    4980
caccacgatg cctgtagcaa tggcaacaac gttgcgcaaa ctattaactg gcgaactact    5040
tactctagct tcccggcaac aattaataga ctggatggag gcggataaag ttgcaggacc    5100
acttctgcgc tcggcccttc cggctggctg gtttattgct gataaatctg gagccggtga    5160
gcgtgggtct cgcggtatca ttgcagcact ggggccagat ggtaagccct cccgtatcgt    5220
agttatctac acgacgggga gtcaggcaac tatggatgaa cgaaatagac agatcgctga    5280
gataggtgcc tcactgatta agcattggta actgtcagac caagtttact catatatact    5340
ttagattgat ttaaaacttc attttttaatt taaaaggatc taggtgaaga tcctttttga    5400
taatctcatg accaaaatcc cttaacgtga gttttcgttc cactgagcgt cagaccccgt    5460
agaaaagatc aaaggatctt cttgagatcc tttttttctg cgcgtaatct gctgcttgca    5520
aacaaaaaaa ccaccgctac cagcggtggt ttgtttgccg gatcaagagc taccaactct    5580
ttttccgaag gtaactggct tcagcagagc gcagatacca aatactgttc ttctagtgta    5640
```

```
gccgtagtta ggccaccact tcaagaactc tgtagcaccg cctacatacc tcgctctgct    5700
aatcctgtta ccagtggctg ctgccagtgg cgataagtcg tgtcttaccg ggttggactc    5760
aagacgatag ttaccggata aggcgcagcg gtcgggctga acgggggggtt cgtgcacaca    5820 gcccagcttg gagcgaacga cctacaccga actgagatac ctacagcgtg agctatgaga    5880
aagcgccacg cttcccgaag ggagaaaggc ggacaggtat ccggtaagcg gcagggtcgg    5940
aacaggagag cgcacgaggg agcttccagg gggaaacgcc tggtatcttt atagtcctgt    6000
cgggtttcgc cacctctgac ttgagcgtcg atttttgtga tgctcgtcag gggggcggag    6060
cctatggaaa aacgccagca acgcggcctt tttacggttc ctggccttt gctggccttt    6120 tgctcacatg ttctttcctg cgttatcccc tgattctgtg gataaccgta ttaccgcctt    6180
tgagtgagct gataccgctc gccgcagccg aacgaccgag cgcagcgagt cagtgagcga    6240
ggaagcggaa gagcgcccaa tacgcaaacc gcctctcccc gcgcgttggc cgattcatta    6300
atgcagctgg cacgacaggt ttcccgactg gaaagcgggc agtgagcgca acgcaattaa    6360
tgtgagttag ctcactcatt aggcacccca ggctttacac tttatgcttc cggctcgtat    6420
gttgtgtgga attgtgagcg gataacaatt tcacacagga aacagctatg accatgatta    6480
cgccagattt aattaagg                                                  6498
```

```
<210> SEQ ID NO 10
<211> LENGTH: 5962
<212> TYPE: DNA
<213> ORGANISM: Artificial Sequence
<220> FEATURE:
<223> OTHER INFORMATION: pAAV.TBG.hUGT1A1co.BGH
<220> FEATURE:
<221> NAME/KEY: repeat_region
<222> LOCATION: (1)..(168)
<223> OTHER INFORMATION: 5' ITR
<220> FEATURE:
<221> NAME/KEY: enhancer
<222> LOCATION: (211)..(310)
<223> OTHER INFORMATION: alpha mc/bik
<220> FEATURE:
<221> NAME/KEY: enhancer
<222> LOCATION: (317)..(416)
<223> OTHER INFORMATION: alpha mc/bik
<220> FEATURE:
<221> NAME/KEY: promoter
<222> LOCATION: (431)..(907)
<223> OTHER INFORMATION: TBG promoter
<220> FEATURE:
<221> NAME/KEY: Intron
<222> LOCATION: (939)..(1071)
<223> OTHER INFORMATION: SV40 misc intron (Promega)
<220> FEATURE:
<221> NAME/KEY: misc_feature
<222> LOCATION: (1086)..(1091)
<223> OTHER INFORMATION: Kozak
<220> FEATURE:
<221> NAME/KEY: misc_feature
<222> LOCATION: (1092)..(2690)
<223> OTHER INFORMATION: UGT1A1 coding sequence
<220> FEATURE:
<221> NAME/KEY: repeat_region
<222> LOCATION: (2695)..(3152)
<223> OTHER INFORMATION: 3' ITR
<220> FEATURE:
<221> NAME/KEY: polyA_signal
<222> LOCATION: (2721)..(2935)
<223> OTHER INFORMATION: BGH polyA
<220> FEATURE:
<221> NAME/KEY: misc_feature
<222> LOCATION: (3915)..(4772)
<223> OTHER INFORMATION: Amp-R coding sequence
<220> FEATURE:
```

```
<221> NAME/KEY: misc_feature
<222> LOCATION: (4946)..(4772)
<223> OTHER INFORMATION: origin

<400> SEQUENCE: 10
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
aggaagatcg gaattcgccc ttaagctagc aggttaattt ttaaaaagca gtcaaaagtc     240
caagtggccc ttggcagcat ttactctctc tgtttgctct ggttaataat ctcaggagca     300
caaacattcc agatccaggt taattttaa aaagcagtca aaagtccaag tggcccttgg      360
cagcatttac tctctctgtt tgctctggtt aataatctca ggagcacaaa cattccagat     420
ccggcgcgcc agggctggaa gctacctttg acatcatttc ctctgcgaat gcatgtataa     480
tttctacaga acctattaga aaggatcacc cagcctctgc ttttgtacaa ctttcccttg     540
aaaaactgcc aattccactg ctgtttggcc caatagtgag aacttttcc tgctgcctct      600 tggtgctttt gcctatggcc cctattctgc ctgctgaaga cactcttgcc agcatggact     660
taaacccctc cagctctgac aatcctcttt ctcttttgtt ttacatgaag ggtctggcag     720
ccaaagcaat cactcaaagt tcaaaccta tcatttttg cttgttcct cttggccttg        780 gttttgtaca tcagctttga aaataccatc ccagggttaa tgctggggtt aatttataac     840
taagagtgct ctagttttgc aatacaggac atgctataaa aatggaaaga tgttgctttc     900
tgagagactg cagaagttgg tcgtgaggca ctgggcaggt aagtatcaag gttacaagac     960
aggtttaagg agaccaatag aaactgggct tgtcgagaca gagaagactc ttgcgtttct    1020
gataggcacc tattggtctt actgacatcc actttgcctt tctctccaca ggtgtccagg    1080
cggccgccac catggccgtg aatctcagg gcggcagacc tctggtgctg gcctgctgc      1140 tgtgtgtgct gggacctgtg gtgtctcacg ccggcaagat cctgctgatc cccgtggatg    1200
gcagccactg gctgtctatg ctgggcgcca ttcagcagct gcagcagagg ggccacgaga    1260
tcgtggtgct ggcccctgat gccagccgt acatcagaga tggcgccttc tacaccctga    1320
aaacctaccc cgtgcccttc cagcgcgagg acgtgaaaga aagcttcgtg tccctgggcc    1380
acaacgtgtt cgagaacgac agcttcctgc agagagtgat caagacctac aagaagatca    1440
agaaagacag cgccatgctg ctgagcggct gctcccatct gctgcacaac aaagaactga    1500
tggcctccct ggccgagagc agcttcgacg tgatgctgac cgacccattc ctgcctgca    1560 gccctatcgt ggcccagtac ctgagcctgc ctaccgtgtt cttcctgcac gccctgcctt    1620
gctcccctgg attcgaggcc acccagtgcc caacccctt cagctacgtg cccagaccac    1680
tgagcagcca cagcgaccac atgaccttc tgcagcgcgt gaagaacatg ctgatcgcct    1740
tcagccagaa cttcctgtgc gacgtggtgt acagccccta cgctaccctg gccagcgaat    1800
tcctgcagcg ggaagtgacc gtgcaggacc tgctgtctag cgccagcgtg tggctgttcc    1860
gcagcgactt cgtgaaggac taccccagac ccatcatgcc aacatggtg ttcgtgggcg    1920 gcatcaactg cctgcaccag aaccccctga gccaggaatt tgaggcctac atcaacgcca    1980
gcggcgagca cggcatcgtg gtgtttagcc tgggcagcat ggtgtccgag atccccgaga    2040
aaaaggccat ggctatcgcc gacgccctgg gaaagatccc ccagacagtg ctgtggcggt    2100
acaccggcac cagacccagc aacctggcca acaacaccat cctcgtgaaa tggctgccc     2160 agaacgacct gctgggccac cctatgaccc gggcctttat cacacacgcc ggctcccatg    2220
```

```
gcgtgtacga gagcatctgc aacggcgtgc ccatggtcat gatgcccctg ttcggcgacc    2280
agatggacaa cgccaagcgg atggaaacaa agggcgctgg cgtgaccctg aacgtgctgg    2340
aaatgaccag cgaggacctg gaaaacgccc tgaaggccgt gatcaacgac aagagctaca    2400
aagaaaacat catgcggctg tccagcctgc acaaggacag acccgtggaa ccctggacc     2460 tggccgtgtt ctgggtggaa ttcgtgatgc ggcacaaggg cgctccccat ctgaggcctg    2520
cagctcacga cctgacctgg tatcagtacc acagcctgga cgtgatcggc ttcctgctgg    2580
cagtggtgct gaccgtggcc ttcatcacct tcaagtgctg cgcctacggc taccggaagt    2640
gcctgggcaa gaaaggcaga gtgaagaagg cccacaagag caagacccac tgataagcat    2700
gcgtcgacgg atccagatct gcctcgactg tgccttctag ttgccagcca tctgttgttt    2760
gcccctcccc cgtgccttcc ttgacccctg aaggtgccac tcccactgtc ctttcctaat    2820
aaaatgagga aattgcatcg cattgtctga gtaggtgtca ttctattctg gggggtgggg    2880
tggggcagga cagcaagggg gaggattggg aagacaatag caggcatgct ggggactcga    2940
gttaagggcg aattcccgat taggatcttc ctagagcatg gctacgtaga taagtagcat    3000
ggcgggttaa tcattaacta caaggaaccc ctagtgatgg agttggccac tccctctctg    3060
cgcgctcgct cgctcactga ggccgggcga ccaaaggtcg cccgacgccc gggctttgcc    3120
cgggcggcct cagtgagcga gcgagcgcgc agccttaatt aacctaattc actggccgtc    3180
gttttacaac gtcgtgactg ggaaaaccct ggcgttaccc aacttaatcg ccttgcagca    3240
catccccctt tcgccagctg gcgtaatagc gaagaggccc gcaccgatcg cccttcccaa    3300
cagttgcgca gcctgaatgg cgaatgggac gcgccctgta gcggcgcatt aagcgcggcg    3360
ggtgtggtgg ttacgcgcag cgtgaccgct acacttgcca gcgccctagc gcccgctcct    3420
ttcgctttct tcccttcctt tctcgccacg ttcgccggct ttccccgtca gctctaaat    3480 cggggggctcc ctttagggtt ccgatttagt gctttacggc acctcgaccc caaaaaactt    3540
gattagggtg atggttcacg tagtgggcca tcgccctgat agacggtttt tcgccctttg    3600
acgttggagt ccacgttctt taatagtgga ctcttgttcc aaactggaac aacactcaac    3660
cctatctcgg tctattcttt tgatttataa gggattttgc cgatttcggc ctattggtta    3720
aaaaatgagc tgatttaaca aaaatttaac gcgaatttta acaaaatatt aacgcttaca    3780
atttaggtgg cacttttcgg ggaaatgtgc gcggaacccc tatttgttta ttttttctaaa    3840 tacattcaaa tatgtatccg ctcatgagac aataaccctg ataaatgctt caataatatt    3900
gaaaaaggaa gagtatgagt attcaacatt tccgtgtcgc ccttattccc ttttttgcgg    3960
cattttgcct tcctgttttt gctcacccag aaacgctggt gaaagtaaaa gatgctgaag    4020
atcagttggg tgcacgagtg ggttacatcg aactggatct caacagcggt aagatccttg    4080
agagttttcg ccccgaagaa cgttttccaa tgatgagcac ttttaaagtt ctgctatgtg    4140
gcgcggtatt atcccgtatt gacgccgggc aagagcaact cggtcgccgc atacactatt    4200
ctcagaatga cttggttgag tactcaccag tcacagaaaa gcatcttacg gatggcatga    4260
cagtaagaga attatgcagt gctgccataa ccatgagtga taacactgcg gccaacttac    4320
ttctgacaac gatcggagga ccgaaggagc taaccgcttt tttgcacaac atggggatc     4380 atgtaactcg ccttgatcgt tgggaaccgg agctgaatga agccatacca aacgacgagc    4440
gtgacaccac gatgcctgta gcaatggcaa caacgttgcg caaactatta actggcgaac    4500
tacttactct agcttcccgg caacaattaa tagactggat ggaggcggat aaagttgcag    4560
```

```
gaccacttct gcgctcggcc cttccggctg gctggtttat tgctgataaa tctggagccg    4620
gtgagcgtgg gtctcgcggt atcattgcag cactggggcc agatggtaag ccctcccgta    4680
tcgtagttat ctacacgacg gggagtcagg caactatgga tgaacgaaat agacagatcg    4740
ctgagatagg tgcctcactg attaagcatt ggtaactgtc agaccaagtt tactcatata    4800
tactttagat tgatttaaaa cttcattttt aatttaaaag gatctaggtg aagatccttt    4860
ttgataatct catgaccaaa atcccttaac gtgagttttc gttccactga gcgtcagacc    4920
ccgtagaaaa gatcaaagga tcttcttgag atccttttttt tctgcgcgta atctgctgct    4980
tgcaaacaaa aaaaccaccg ctaccagcgg tggtttgttt gccggatcaa gagctaccaa    5040 ctcttttttcc gaaggtaact ggcttcagca gagcgcagat accaaatact gttcttctag    5100
tgtagccgta gttaggccac cacttcaaga actctgtagc accgcctaca tacctcgctc    5160
tgctaatcct gttaccagtg gctgctgcca gtggcgataa gtcgtgtctt accgggttgg    5220
actcaagacg atagttaccg gataaggcgc agcggtcggg ctgaacgggg ggttcgtgca    5280
cacagcccag cttggagcga acgacctaca ccgaactgag atacctacag cgtgagctat    5340
gagaaagcgc cacgcttccc gaagggagaa aggcggacag gtatccggta agcggcaggg    5400
tcggaacagg agagcgcacg agggagcttc caggggggaaa cgcctggtat ctttatagtc    5460
ctgtcgggtt tcgccacctc tgacttgagc gtcgattttt gtgatgctcg tcagggggggc    5520 ggagcctatg gaaaaacgcc agcaacgcgg cctttttacg gttcctggcc ttttgctggc    5580
cttttgctca catgttcttt cctgcgttat cccctgattc tgtggataac cgtattaccg    5640
cctttgagtg agctgatacc gctcgccgca gccgaacgac cgagcgcagc gagtcagtga    5700
gcgaggaagc ggaagagcgc ccaatacgca aaccgcctct ccccgcgcgt tggccgattc    5760
attaatgcag ctggcacgac aggtttcccg actggaaagc gggcagtgag cgcaacgcaa    5820
ttaatgtgag ttagctcact cattaggcac cccaggcttt acactttatg cttccggctc    5880
gtatgttgtg tggaattgtg agcggataac aatttcacac aggaaacagc tatgaccatg    5940
attacgccag atttaattaa gg                                             5962
```

```
<210> SEQ ID NO 11
<211> LENGTH: 738
<212> TYPE: PRT
<213> ORGANISM: Artificial Sequence
<220> FEATURE:
<223> OTHER INFORMATION: AAV8 VP1 capsid protein

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

-continued

Asn Leu Gly Arg Ala Val Phe Gln Ala Lys Lys Arg Val Leu Glu Pro
115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile

```
                  530                 535                 540
Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Asn Thr Ala
                580                 585                 590

Pro Gln Ile Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 12
<211> LENGTH: 1599
<212> TYPE: DNA
<213> ORGANISM: Artificial Sequence
<220> FEATURE:
<223> OTHER INFORMATION: engineered UGT1A1 U201DPmod

<400> SEQUENCE: 12
atggccgtgg agagccaggg aggacggcct ctggtgctgg actgctgct gtgcgtgctg      60 ggacctgtgg tgagccacgc cggaaagatc ctgctgatcc tgtgtgacgg aagccactgg    120
ctgagcatgc tgggagccat ccagcagctg cagcagcggg acacgagat cgtggtgctg     180 gcccctgacg ccagcctgta catccgggac ggagccttct acaccctgaa gacctaccct    240
gtgcctttcc agcgggagga cgtgaaggag agcttcgtga gcctgggaca caacgtgttc    300
gagaacgata gcttcctgca gcgggtgatc aagacctaca agaagatcaa gaaggacagc    360
gccatgctgc tgagcggctg cagccacctg ctgcacaaca aggagctgat ggccagcctg    420
gccgagagca gcttcgacgt gatgctgacc gacccttttcc tgccttgcag ccctatcgtg    480
gcccagtacc tgagcctgcc taccgtgttc ttcctgcacg ccctgccttg cagcctggag    540
ttcgaggcca cccagtgccc taacccttttc agctacgtgc tcggcctct gagcagccac    600 agcgaccaca tgaccttcct gcagcgggtg aagaacatgc tgatcgcctt cagccagaac    660
ttcctgtgcg acgtggtgta cagcccttac gccaccctgg ccagcgagtt cctgcagcgg    720
gaggtgaccg tgcaggacct gctgagcagc gccagcgtgt ggctgttccg gagcgacttc    780
gtgaaggact accctcggcc tatcatgcct aacatggtgt cgtgggagg aatcaactgc    840 ctgcaccaga accctctgag ccaggagttc gaggcctaca tcaacgccag cggagagcac    900
```

```
ggaatcgtgg tgttcagcct gggaagcatg gtgagcgaga tccctgagaa gaaggccatg      960
gccatcgccg acgccctggg aaagatccct cagaccgtgc tgtggcggta caccggaacc     1020
cggcctagca acctggccaa caacaccatc ctggtgaagt ggctgcctca gaacgatctg     1080
ctgggacacc ctatgacccg ggccttcatc acccacgccg aagccacgg agtgtacgag      1140 agcatctgca acggagtgcc tatggtgatg atgcctctgt cggagacca gatggacaac      1200 gccaagcgga tggagaccaa gggagccgga gtgccctga acgtgctgga gatgaccagc      1260
gaggacctgg agaacgccct gaaggccgtg atcaacgata gagctacaa ggagaacatc      1320 atgcggctga gcagcctgca aggaccgg cctgtggagc tctggaccct ggccgtgttc       1380
tgggtggagt tcgtgatgcg gcacaaggga gcccctcacc tgcggcctgc cgcccacgac     1440
ctgacctggt accagtacca cagcctggac gtgatcggat tcctgctggc cgtggtgctg    1500
accgtggcct tcatcacctt caagtgctgc gcctacggat accggaagtg cctgggaaag   1560
aagggacggg tgaagaaggc ccacaagagc aagacccac                            1599

<210> SEQ ID NO 13
<211> LENGTH: 1599
<212> TYPE: DNA
<213> ORGANISM: Artificial sequence
<220> FEATURE:
<223> OTHER INFORMATION: engineered UGT1A1 U001mod

<400> SEQUENCE: 13
atggccgtgg agagccaggg ggggcggccc ctggtgctgg ggctgctgct gtgcgtgctg       60
gggcccgtgg tgagccacgc cgggaagatc ctgctgatcc ccgtggacgg gagccactgg     120
ctgagcatgc tgggggccat ccagcagctg cagcagcggg ggcacgagat cgtggtgctg     180 gccccccgacg ccagcctgta catccgggac ggggccttct acaccctgaa gacctacccc     240
gtgcccttcc agcgggagga cgtgaaggag agcttcgtga gcctggggca acgtgttc      300 gagaacgata gcttcctgca gcgggtgatc aagacctaca gaagatcaa gaaggacagc      360 gccatgctgc tgagcgggtg cagccacctg ctgcacaaca aggagctgat ggccagcctg     420
gccgagagca gcttcgacgt gatgctgacc gacccctttcc tgccctgcag ccccatcgtg    480
gcccagtacc tgagcctgcc caccgtgttc ttcctgcacg ccctgccctg cagcctggag    540
ttcgaggcca cccagtgccc caaccccttc agctacgtgc ccggcccct gagcagccac      600 agcgaccaca tgaccttcct gcagcgggtg aagaacatgc tgatcgcctt cagccagaac    660
ttcctgtgcg acgtggtgta cagccccac gccaccctgg ccagcgagtt cctgcagcgg     720
gaggtgaccg tgcaggacct gctgagcagc gccagcgtgt ggctgttccg gagcgacttc    780
gtgaaggact accccggcc catcatgccc aacatggtgt tcgtgggggg gatcaactgc      840
ctgcaccaga acccctgag ccaggagttc gaggcctaca tcaacgccag cggggagcac     900
gggatcgtgg tgttcagcct gggagcatg gtgagcgaga tccccgagaa gaaggccatg     960
gccatcgccg acgccctggg gaagatcccc cagaccgtgc tgtggcggta caccgggacc    1020
cggcccagca acctggccaa caacaccatc ctggtgaagt ggctgcccca gaacgatctg    1080
ctggggcacc ccatgacccg ggccttcatc acccacgccg ggagccacgg ggtgtacgag   1140
agcatctgca acggggtgcc catggtgatg atgcccctgt cggggaccag atggacaac    1200 gccaagcgga tggagaccaa ggggggccggg gtgccctga acgtgctgga gatgaccagc   1260
gaggacctgg agaacgccct gaaggccgtg atcaacgata gagctacaa ggagaacatc   1320
```

| | |
|---|---|
| atgcggctga gcagcctgca caaggaccgg cccgtggagc ccctggacct ggccgtgttc | 1380 |
| tgggtggagt tcgtgatgcg gcacaagggg cccccccacc tgcggcccgc cgcccacgac | 1440 |
| ctgacctggt accagtacca cagcctggac gtgatcgggt tcctgctggc cgtggtgctg | 1500 |
| accgtggcct tcatcacctt caagtgctgc gcctacgggt accggaagtg cctggggaag | 1560 |
| aagggcgggt gaagaaggc ccacaagagc aagacccac | 1599 |

<210> SEQ ID NO 14
<211> LENGTH: 1599
<212> TYPE: DNA
<213> ORGANISM: Artificial sequence
<220> FEATURE:
<223> OTHER INFORMATION: engineered UGT1A1 U011TYmod

<400> SEQUENCE: 14

| | |
|---|---|
| atggctgtgg aaagccaggg cggccggccc ctggtgctgg gcctgctgct gtgtgtgctg | 60 |
| gcccccgtgg tgagccacgc tggcaagatt ctgctgattc ccgtggacgg cagccactgg | 120 |
| ctgagcatgc tgggcgctat tcagcagctg cagcagcggg ccacgaaat tgtggtgctg | 180 |
| gctcccgacg ctagcctgta cattcgggac ggcgcttttt acaccctgaa gacctacccc | 240 |
| gtgcccttc agcgggaaga cgtgaaggaa agctttgtga gctgggcca acgtgtttt | 300 |
| gaaaacgata gctttctgca gcgggtgatt aagacctaca agaagattaa gaaggacagc | 360 |
| gctatgctgc tgagcggctg tagccacctg ctgcacaaca aggaactgat ggctagcctg | 420 |
| gctgaaagca gctttgacgt gatgctgacc gaccccttc tgccctgtag ccccattgtg | 480 |
| gctcagtacc tgagcctgcc caccgtgttt tttctgcacg ctctgccctg tagcctggaa | 540 |
| tttgaagcta cccagtgtcc caacccctt agctacgtgc ccggcccct gagcagccac | 600 |
| agcgaccaca tgacctttct gcagcgggtg aagaacatgc tgattgcttt tagccagaac | 660 |
| tttctgtgtg acgtggtgta cagcccctac gctaccctgg ctagcgaatt tctgcagcgg | 720 |
| gaagtgaccg tgcaggacct gctgagcagc gctagcgtgt ggctgttcg gagcgacttt | 780 |
| gtgaaggact ccccccggcc cattatgccc aacatggtgt tgtgggcgg cattaactgt | 840 |
| ctgcaccaga ccccctgag ccaggaattt gaagcttaca ttaacgctag cggcgaacac | 900 |
| ggcattgtgg tgtttagcct gggcagcatg gtgagcgaaa ttcccgaaaa gaaggctatg | 960 |
| gctattgctg acgctctggg caagattccc cagaccgtgc tgtggcggta caccggcacc | 1020 |
| cggcccagca acctggctaa caacaccatt ctggtgaagt ggctgcccca gaacgatctg | 1080 |
| ctgggccacc ccatgacccg ggcttttatt ccccacgctg gcagccacgg cgtgtacgaa | 1140 |
| agcatttgta acggcgtgcc catggtgatg atgcccctgt ttggcgacca gatggacaac | 1200 |
| gctaagcgga tggaaaccaa gggcgctggc gtgaccctga acgtgctgga atgaccagc | 1260 |
| gaagacctgg aaaacgctct gaaggctgtg attaacgata gagctacaa ggaaaacatt | 1320 |
| atgcggctga gcagcctgca caaggaccgg cccgtggaac ccctggacct ggctgtgttt | 1380 |
| tgggtggaat ttgtgatgcg gcacaagggc gctccccacc tgcggcccgc tgctcacgac | 1440 |
| ctgacctggt accagtacca cagcctggac gtgattggct ttctgctggc tgtggtgctg | 1500 |
| accgtggctt ttattacctt taagtgttgt gcttacggct accggaagtg tctgggcaag | 1560 |
| aagggccggg tgaagaaggc tcacaagagc aagacccac | 1599 |

<210> SEQ ID NO 15
<211> LENGTH: 3140
<212> TYPE: DNA
<213> ORGANISM: Artificial sequence

```
<220> FEATURE:
<223> OTHER INFORMATION: pAAV.TGB.U201DP.BGH (p4120)
<220> FEATURE:
<221> NAME/KEY: repeat_region
<222> LOCATION: (1)..(168)
<223> OTHER INFORMATION: 5' ITR
<220> FEATURE:
<221> NAME/KEY: enhancer
<222> LOCATION: (211)..(310)
<223> OTHER INFORMATION: alpha mic/bik enhancer
<220> FEATURE:
<221> NAME/KEY: enhancer
<222> LOCATION: (317)..(416)
<223> OTHER INFORMATION: alpha mic/bik enhancer
<220> FEATURE:
<221> NAME/KEY: promoter
<222> LOCATION: (431)..(907)
<223> OTHER INFORMATION: TBG promoter
<220> FEATURE:
<221> NAME/KEY: Intron
<222> LOCATION: (939)..(1071)
<223> OTHER INFORMATION: SV40 misc intron (Promega)
<220> FEATURE:
<221> NAME/KEY: misc_feature
<222> LOCATION: (1092)..(2690)
<223> OTHER INFORMATION: U201DPmod CDS
<220> FEATURE:
<221> NAME/KEY: polyA_signal
<222> LOCATION: (2709)..(2923)
<223> OTHER INFORMATION: BGH polyA
<220> FEATURE:
<221> NAME/KEY: repeat_region
<222> LOCATION: (2973)..(3140)
<223> OTHER INFORMATION: AAV 3' ITR

<400> SEQUENCE: 15
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
aggaagatcg gaattcgccc ttaagctagc aggttaattt ttaaaaagca gtcaaaagtc     240
caagtggccc ttggcagcat ttactctctc tgtttgctct ggttaataat ctcaggagca     300
caaacattcc agatccaggt taattttta aaagcagtca aaagtccaag tggcccttgg     360
cagcatttac tctctctgtt tgctctggtt aataatctca ggagcacaaa cattccagat     420
ccggcgcgcc agggctggaa gctacctttg acatcatttc ctctgcgaat gcatgtataa     480
tttctacaga acctattaga aaggatcacc cagcctctgc ttttgtacaa ctttcccttg     540
aaaaactgcc aattccactg ctgtttggcc caatagtgag aacttttttcc tgctgcctct     600 tggtgctttt gcctatggcc cctattctgc ctgctgaaga cactcttgcc agcatggact     660
taaacccctc cagctctgac aatcctcttt ctcttttgtt ttacatgaag ggtctggcag     720
ccaaagcaat cactcaaagt tcaaacctta tcatttttg ctttgttcct cttggccttg     780
gttttgtaca tcagctttga aaataccatc ccagggttaa tgctggggtt aatttataac     840
taagagtgct ctagttttgc aatacaggac atgctataaa aatggaaaga tgttgctttc     900
tgagagactg cagaagttgg tcgtgaggca ctgggcaggt aagtatcaag gttacaagac     960
aggtttaagg agaccaatag aaactgggct tgtcgagaca gagaagactc ttgcgtttct    1020
gataggcacc tattggtctt actgacatcc actttgcctt tctctccaca ggtgtccagg    1080
cggccgccac catggccgtg gagagccagg aggacggcc tctggtgctg gactgctgc     1140 tgtgcgtgct gggacctgtg gtgagccacg ccggaaagat cctgctgatc cctgtggacg    1200
gaagccactg gctgagcatg ctgggagcca tccagcagct gcagcagcgg ggacacgaga    1260
```

```
tcgtggtgct ggcccctgac gccagcctgt acatccggga cggagccttc tacaccctga    1320
agacctaccc tgtgcctttc cagcgggagg acgtgaagga gagcttcgtg agcctgggac    1380
acaacgtgtt cgagaacgat agcttcctgc agcgggtgat caagacctac aagaagatca    1440
agaaggacag cgccatgctg ctgagcggct gcagccacct gctgcacaac aaggagctga    1500
tggccagcct ggccgagagc agcttcgacg tgatgctgac cgacccttc ctgccttgca    1560
gccctatcgt ggcccagtac ctgagcctgc ctaccgtgtt cttcctgcac gccctgcctt    1620
gcagcctgga gttcgaggcc acccagtgcc ctaacccttt cagctacgtg cctcggcctc    1680
tgagcagcca cagcgaccac atgaccttcc tgcagcgggt gaagaacatg ctgatcgcct    1740
tcagccagaa cttcctgtgc gacgtggtgt acagcccta cgccaccctg ccagcgagt    1800
tcctgcagcg ggaggtgacc gtgcaggacc tgctgagcag cgccagcgtg tggctgttcc    1860
ggagcgactt cgtgaaggac taccctcggc ctatcatgcc taacatggtg ttcgtgggag    1920
gaatcaactg cctgcaccag aaccctctga ccaggagtt cgaggcctac atcaacgcca    1980
gcggagagca cggaatcgtg gtgttcagcc tgggaagcat ggtgagcgag atccctgaga    2040
agaaggccat ggccatcgcc gacgccctgg gaaagatccc tcagaccgtg ctgtggcggt    2100
acaccggaac ccggcctagc aacctggcca acaacaccc cctggtgaag tggctgcctc    2160
agaacgatct gctgggacac cctatgaccc gggccttcat cacccacgcc ggaagccacg    2220
gagtgtacga gagcatctgc aacggagtgc ctatggtgat gatgcctctg ttcggagacc    2280
agatggacaa cgccaagcgg atggagacca agggagccgg agtgaccctg aacgtgctgg    2340
agatgaccag cgaggacctg gagaacgccc tgaaggccgt gatcaacgat aagagctaca    2400
aggagaacat catgcggctg agcagcctgc acaaggaccg gcctgtggag cctctggacc    2460
tggccgtgtt ctgggtggag ttcgtgatgc ggcacaaggg agcccctcac ctgcggcctg    2520
ccgcccacga cctgacctgg taccagtacc acagcctgga cgtgatcgga ttcctgctgg    2580
ccgtggtgct gaccgtggcc ttcatcaccct tcaagtgctg cgcctacgga taccggaagt    2640
gcctgggaaa gaagggacgg gtgaagaagg cccacaagag caagacccac tgataaggat    2700
ccagatctgc ctcgactgtg ccttctagtt gccagccatc tgttgtttgc ccctcccccg    2760
tgccttcctt gaccctggaa ggtgccactc ccactgtcct ttcctaataa aatgaggaaa    2820
ttgcatcgca ttgtctgagt aggtgtcatt ctattctggg gggtggggtg ggcaggaca     2880
gcaagggga ggattgggaa gacaatagca ggcatgctgg ggactcgagt taagggcgaa     2940
ttcccgatta ggatcttcct agagcatggc tacgtagata gtagcatgg cgggttaatc     3000
attaactaca aggaacccct agtgatggag ttggccactc cctctctgcg cgctcgctcg    3060
ctcactgagg ccgggcgacc aaaggtcgcc cgacgcccgg gctttgcccg ggcggcctca    3120
gtgagcgagc gagcgcgcag                                                3140

<210> SEQ ID NO 16
<211> LENGTH: 3140
<212> TYPE: DNA
<213> ORGANISM: Artificial sequence
<220> FEATURE:
<223> OTHER INFORMATION: pAAV.TBG.U011TY.BGH (p4119)
<220> FEATURE:
<221> NAME/KEY: repeat_region
<222> LOCATION: (1)..(168)
<223> OTHER INFORMATION: AAV 5' ITR
<220> FEATURE:
<221> NAME/KEY: enhancer
<222> LOCATION: (211)..(310)
<223> OTHER INFORMATION: alpha mic/bik
```

```
<220> FEATURE:
<221> NAME/KEY: enhancer
<222> LOCATION: (317)..(416)
<223> OTHER INFORMATION: alpha mic/bik
<220> FEATURE:
<221> NAME/KEY: promoter
<222> LOCATION: (431)..(907)
<223> OTHER INFORMATION: TBG promoter
<220> FEATURE:
<221> NAME/KEY: Intron
<222> LOCATION: (939)..(1071)
<223> OTHER INFORMATION: SV40 misc intron (Promega)
<220> FEATURE:
<221> NAME/KEY: misc_feature
<222> LOCATION: (1092)..(2690)
<223> OTHER INFORMATION: CDS for modfied U011TY
<220> FEATURE:
<221> NAME/KEY: polyA
<222> LOCATION: (2709)..(2923)
<223> OTHER INFORMATION: BGH polyA
<220> FEATURE:
<221> NAME/KEY: repeat_region
<222> LOCATION: (2973)..(3140)
<223> OTHER INFORMATION: AAV 3'ITR

<400> SEQUENCE: 16
```

| | | | | | |
|---|---|---|---|---|---|
| ctgcgcgctc | gctcgctcac | tgaggccgcc | cgggcaaagc | ccgggcgtcg | ggcgaccttt        60 |
| ggtcgcccgg | cctcagtgag | cgagcgagcg | cgcagagagg | gagtggccaa | ctccatcact       120 |
| aggggttcct | tgtagttaat | gattaacccg | ccatgctact | tatctacgta | gccatgctct       180 |
| aggaagatcg | gaattcgccc | ttaagctagc | aggttaattt | ttaaaaagca | gtcaaaagtc       240 |
| caagtggccc | ttggcagcat | ttactctctc | tgtttgctct | ggttaataat | ctcaggagca       300 |
| caaacattcc | agatccaggt | taattttaa  | aaagcagtca | aaagtccaag | tggcccttgg       360 |
| cagcatttac | tctctctgtt | tgctctggtt | aataatctca | ggagcacaaa | cattccagat       420 |
| ccggcgcgcc | agggctggaa | gctacctttg | acatcatttc | ctctgcgaat | gcatgtataa       480 |
| tttctacaga | acctattaga | aaggatcacc | cagcctctgc | ttttgtacaa | ctttcccttta     540 |
| aaaaactgcc | aattccactg | ctgtttggcc | caatagtgag | aactttttcc | tgctgcctct       600 |
| tggtgctttt | gcctatggcc | cctattctgc | ctgctgaaga | cactcttgcc | agcatggact       660 |
| taaacccctc | cagctctgac | aatcctcttt | ctcttttgtt | ttacatgaag | ggtctggcag       720 |
| ccaaagcaat | cactcaaagt | tcaaaccttta | tcattttttg | ctttgttcct | cttggccttg       780 |
| gttttgtaca | tcagctttga | aaataccatc | ccagggttaa | tgctggggtt | aatttataac       840 |
| taagagtgct | ctagttttgc | aatacaggac | atgctataaa | aatggaaaga | tgttgctttc       900 |
| tgagagactc | cagaagttgg | tcgtgaggca | ctgggcaggt | aagtatcaag | gttacaagac       960 |
| aggtttaagg | agaccaatag | aaactgggct | tgtcgagaca | gagaagactc | ttgcgtttct      1020 |
| gataggcacc | tattggtctt | actgacatcc | actttgcctt | tctctccaca | ggtgtccagg      1080 |
| cggccgccac | catggctgtg | gaaagccagg | gcggccggcc | cctggtgctg | ggcctgctgc      1140 |
| tgtgtgtgct | gggccccgtg | gtgagccacg | ctggcaagat | tctgctgatt | cccgtggacg      1200 |
| gcagccactg | gctgagcatg | ctgggcgcta | ttcagcagct | gcagcagcgg | ggccacgaaa      1260 |
| ttgtggtgct | ggctcccgac | gctagcctgt | acattcggga | cggcgctttt | tacaccctga      1320 |
| agacctaccc | cgtgcccttt | cagcgggaag | acgtgaagga | aagctttgtg | agcctgggcc      1380 |
| acaacgtgtt | tgaaaacgat | agctttctgc | agcgggtgat | taagacctac | aagaagatta      1440 |
| agaaggacag | cgctatgctg | ctgagcggct | gtagccacct | gctgcacaac | aaggaactga      1500 |
| tggctagcct | ggctgaaagc | agctttgacg | tgatgctgac | cgaccccttt | ctgccctgta      1560 |

-continued

```
gccccattgt ggctcagtac ctgagcctgc ccaccgtgtt ttttctgcac gctctgccct    1620
gtagcctgga atttgaagct acccagtgtc ccaacccctt tagctacgtg ccccggcccc    1680
tgagcagcca cagcgaccac atgacctttc tgcagcgggt gaagaacatg ctgattgctt    1740
ttagccagaa ctttctgtgt gacgtggtgt acagccccta cgctacccct gctagcgaat    1800
ttctgcagcg ggaagtgacc gtgcaggacc tgctgagcag cgctagcgtg tggctgtttc    1860
ggagcgactt tgtgaaggac tacccccggc ccattatgcc caacatggtg tttgtgggcg    1920
gcattaactg tctgcaccag aaccccctga gccaggaatt tgaagcttac attaacgcta    1980
gcggcgaaca cggcattgtg gtgtttagcc tgggcagcat ggtgagcgaa attcccgaaa    2040
agaaggctat ggctattgct gacgctctgg gcaagattcc ccagaccgtg ctgtggcggt    2100
acaccggcac ccggcccagc aacctggcta caacaccat tctggtgaag tggctgcccc    2160
agaacgatct gctgggccac cccatgaccc gggcttttat tacccacgct ggcagccacg    2220
gcgtgtacga aagcatttgt aacggcgtgc ccatggtgat gatgcccctg tttggcgacc    2280
agatggacaa cgctaagcgg atggaaacca agggcgctgg cgtgaccctg aacgtgctgg    2340
aaatgaccag cgaagacctg aaaacgctc tgaaggctgt gattaacgat aagagctaca    2400
aggaaaacat tatgcggctg agcagcctgc acaaggaccg gcccgtggaa cccctggacc    2460
tggctgtgtt tgggtggaa tttgtgatgc ggcacaaggg cgctccccac ctgcggcccg    2520
ctgctcacga cctgacctgg taccagtacc acagcctgga cgtgattggc tttctgctgg    2580
ctgtggtgct gaccgtggct tttattacct ttaagtgttg tgcttacggc taccggaagt    2640
gtctgggcaa gaagggccgg gtgaagaagg ctcacaagag caagacccac tgataaggat    2700
ccagatctgc ctcgactgtg ccttctagtt gccagccatc tgttgtttgc ccctcccccg    2760
tgccttcctt gaccctggaa ggtgccactc ccactgtcct ttcctaataa aatgaggaaa    2820
ttgcatcgca ttgtctgagt aggtgtcatt ctattctggg gggtggggtg gggcaggaca    2880
gcaagggga ggattgggaa gacaatagca ggcatgctgg ggactcgagt taagggcgaa    2940
ttccccgatta ggatcttcct agagcatggc tacgtagata gtagcatgg cgggttaatc    3000
attaactaca aggaacccct agtgatggag ttggccactc cctctctgcg cgctcgctcg    3060
ctcactgagg ccgggcgacc aaaggtcgcc cgacgcccgg gctttgcccg gcggcctca    3120
gtgagcgagc gagcgcgcag                                                3140
```

<210> SEQ ID NO 17
<211> LENGTH: 3140
<212> TYPE: DNA
<213> ORGANISM: Artificial sequence
<220> FEATURE:
<223> OTHER INFORMATION: pAAV.TBG.U001.BGH (p4118)

<400> SEQUENCE: 17

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagctagc aggttaattt ttaaaaagca gtcaaaagtc    240
caagtggccc ttggcagcat ttactctctc tgtttgctct ggttaataat ctcaggagca    300
caaacattcc agatccaggt taatttttaa aaagcagtca aaagtccaag tggcccttgg    360
cagcatttac tctctctgtt tgctctggtt aataatctca ggagcacaaa cattccagat    420
ccggcgcgcc agggctggaa gctacctttg acatcatttc ctctgcgaat gcatgtataa    480
```

```
tttctacaga acctattaga aaggatcacc cagcctctgc ttttgtacaa ctttccctta      540
aaaaactgcc aattccactg ctgtttggcc caatagtgag aacttttcc tgctgcctct       600 tggtgctttt gcctatggcc cctattctgc ctgctgaaga cactcttgcc agcatggact      660 taaaccctc cagctctgac aatcctcttt ctcttttgtt ttacatgaag ggtctggcag       720
ccaaagcaat cactcaaagt tcaaacctta tcatttttg ctttgttcct cttggccttg       780
gttttgtaca tcagctttga aaataccatc ccagggttaa tgctggggtt aatttataac     840
taagagtgct ctagttttgc aatacaggac atgctataaa aatggaaaga tgttgctttc     900
tgagagactg cagaagttgg tcgtgaggca ctgggcaggt aagtatcaag gttacaagac     960
aggtttaagg agaccaatag aaactgggct tgtcgagaca gagaagactc ttgcgtttct    1020
gataggcacc tattggtctt actgacatcc actttgcctt tctctccaca ggtgtccagg    1080
cggccgccac catggccgtg gagagccagg gggggcggcc cctggtgctg ggctgctgc     1140 tgtgcgtgct ggggccgtg gtgagccacg ccgggaagat cctgctgatc cccgtggacg     1200
ggagccactg gctgagcatg ctgggggcca tccagcagct gcagcagcgg gggcacgaga    1260
tcgtggtgct ggcccccgac gccagcctgt acatccggga cggggccttc tacaccctga    1320
agacctaccc cgtgcccttc cagcgggagg acgtgaagga gcttcgtg agcctggggc      1380 acaacgtgtt cgagaacgat agcttcctgc agcgggtgat caagacctac aagaagatca    1440
agaaggacag cgccatgctg ctgagcgggt gcagccacct gctgcacaac aaggagctga    1500
tggccagcct ggccgagagc agcttcgacg tgatgctgac cgacccttc ctgccctgca     1560 gccccatcgt ggcccagtac ctgagcctgc ccaccgtgtt cttcctgcac gccctgccct    1620
gcagcctgga gttcgaggcc acccagtgcc ccaaccccctt cagctacgtg ccccggcccc    1680
tgagcagcca cagcgaccac atgaccttcc tgcagcgggt gaagaacatg ctgatcgcct    1740
tcagccagaa cttcctgtgc gacgtggtgt acagccccta cgccaccctg ccagcgagt     1800 tcctgcagcg ggaggtgacc gtgcaggacc tgctgagcag cgccagcgtg tggctgttcc    1860
ggagcgactt cgtgaaggac tacccccggc ccatcatgcc caacatggtg ttcgtggggg    1920
ggatcaactg cctgcaccag aacccctga gccaggagtt cgaggcctac atcaacgcca     1980
gcggggagca cgggatcgtg gtgttcagcc tggggagcat ggtgagcgag atccccgaga    2040
agaaggccat ggccatcgcc gacgcccggg ggaagatccc ccagaccgtg ctgtggcggt    2100
acaccgggac ccggcccagc aacctggcca caacaccat cctggtgaag tggctgcccc     2160
agaacgatct gctggggcac cccatgaccc gggccttcat cacccacgcc gggagccacg    2220
gggtgtacga gagcatctgc aacggggtgc ccatggtgat gatgcccctg ttcgggacc     2280 agatggacaa cgccaagcgg atggagacca aggggccgg ggtgaccctg aacgtgctgg    2340
agatgaccag cgaggacctg gagaacgccc tgaaggccgt gatcaacgat aagagctaca    2400
aggagaacat catgcgctg agcagcctgc acaaggaccg gccgtggag cccctggacc      2460 tggccgtgtt ctgggtggag ttcgtgatgc ggcacaaggg ggccccccac ctgcggccgc    2520
ccgcccacga cctgacctgg taccagtacc acagcctgga cgtgatcggg ttcctgctgg    2580
ccgtggtgct gaccgtggcc ttcatcacct tcaagtgctg cgcctacggg taccggaagt    2640
gcctggggaa gaaggggcgg gtgaagaagg cccacaagag caagacccac tgataaggat    2700
ccagatctgc ctcgactgtg ccttctagtt gccagccatc tgttgtttgc ccctcccccg    2760
tgccttcctt gaccctggaa ggtgccactc ccactgtcct ttcctaataa aatgaggaaa    2820
```

| | |
|---|---|
| ttgcatcgca ttgtctgagt aggtgtcatt ctattctggg gggtggggtg gggcaggaca | 2880 |
| gcaaggggga ggattgggaa gacaatagca ggcatgctgg ggactcgagt taagggcgaa | 2940 |
| ttcccgatta ggatcttcct agagcatggc tacgtagata agtagcatgg cgggttaatc | 3000 |
| attaactaca aggaacccct agtgatggag ttggccactc cctctctgcg cgctcgctcg | 3060 |
| ctcactgagg ccgggcgacc aaaggtcgcc cgacgcccgg gctttgcccg ggcggcctca | 3120 |
| gtgagcgagc gagcgcgcag | 3140 |

<210> SEQ ID NO 18
<211> LENGTH: 1599
<212> TYPE: DNA
<213> ORGANISM: Artificial Sequence
<220> FEATURE:
<223> OTHER INFORMATION: engineered UG1A1 U3G

<400> SEQUENCE: 18

| | |
|---|---|
| atggctgtgg agagccaggg gggcaggccc ctggtgctgg gcctgctgct gtgtgtgctg | 60 |
| ggccctgtgg tgagccatgc tggcaagatc ctgctgatcc ctgtggatgg cagccactgg | 120 |
| ctgagcatgc tgggggccat ccagcagctg cagcagaggg ccatgagat tgtggtgctg | 180 |
| gcccctgatg ccagcctgta catcagggat ggggccttct acaccctgaa gacctaccct | 240 |
| gtgcccttcc agagggagga tgtgaaggag agctttgtga gctgggcca caatgtgttt | 300 |
| gagaatgaca gcttcctgca gagggtgatc aagacctaca agaagatcaa gaaggactct | 360 |
| gccatgctgc tgtctggctg cagccacctg ctgcacaaca aggagctgat ggccagcctg | 420 |
| gctgagagca gctttgatgt gatgctgact gaccccttcc tgcctgcag ccccattgtg | 480 |
| gcccagtacc tgagcctgcc cactgtgttc ttcctgcatg ccctgccctg cagcctggag | 540 |
| tttgaggcca cccagtgccc caaccccttc agctatgtgc ccaggcccct gagcagccac | 600 |
| tctgaccaca tgaccttcct gcagagggtg aagaacatgc tgattgcctt cagccagaac | 660 |
| ttcctgtgtg atgtggtgta cagccccat gccaccctgg cctctgagtt cctgcagagg | 720 |
| gaggtgactg tgcaggacct gctgagctct gcctctgtgt ggctgttcag gtctgacttt | 780 |
| gtgaaggact accccaggcc catcatgccc aacatggtgt tgtgggggg catcaactgc | 840 |
| ctgcaccaga ccccctgag ccaggagttt gaggcctaca tcaatgcctc tgggagcat | 900 |
| ggcatagtgg tgttcagcct gggcagcatg gtgtctgaga tccctgagaa gaaggccatg | 960 |
| gccattgctg atgccctagg caagatcccc cagactgtgc tgtggaggta cactggcacc | 1020 |
| aggcccagca acctggccaa caacaccatc ctggtgaagt ggctgccca gaatgacctg | 1080 |
| ctgggccacc ccatgaccag ggccttcatc acccatgctg gcagccatgg ggtgtatgag | 1140 |
| agcatctgca atgggtgcc catggtgatg atgcccctgt tggggaccca gatggacaat | 1200 |
| gccaagagga tggaaaccaa gggggctggg gtgaccctga atgtgctgga gatgacctct | 1260 |
| gaggacctgg agaatgccct gaaggctgtg atcaatgaca gagctacaa ggagaacatc | 1320 |
| atgaggctga gcagcctgca caaggacagg cctgtggagc ccctggacct ggctgtgttc | 1380 |
| tgggtggagt ttgtgatgag gcataagggg gcccccacc tgaggcctgc tgcccatgac | 1440 |
| ctgacctggt accagtacca cagcctagat gtgattggc tcctgctggc tgtggtgctg | 1500 |
| actgtggcct tcatcacctt taagtgctgt gcctatggct acaggaagtg cctgggcaag | 1560 |
| aagggcaggg tgaagaaggc ccacaagagc aagacccac | 1599 |